US012613188B2

(12) United States Patent
Im et al.

(10) Patent No.: US 12,613,188 B2
(45) Date of Patent: Apr. 28, 2026

(54) METHODS AND SYSTEMS OF ENHANCING ELECTROMAGNETIC RADIATION SIGNALS FROM EXTRACELLULAR VESICLES

(71) Applicant: The General Hospital Corporation, Boston, MA (US)

(72) Inventors: Hyungsoon Im, Peabody, MA (US); Ralph Weissleder, Peabody, MA (US)

(73) Assignee: The General Hospital Corporation, Boston, MA (US)

( * ) Notice: Subject to any disclaimer, the term of this patent is extended or adjusted under 35 U.S.C. 154(b) by 194 days.

(21) Appl. No.: 17/966,621

(22) Filed: Oct. 14, 2022

(65) Prior Publication Data

US 2023/0123746 A1      Apr. 20, 2023

Related U.S. Application Data

(63) Continuation-in-part of application No. PCT/US2021/027350, filed on Apr. 14, 2021.

(Continued)

(51) Int. Cl.
| | |
|---|---|
| *G01N 21/55* | (2014.01) |
| *G01N 15/0227* | (2024.01) |

(Continued)

(52) U.S. Cl.
CPC ....... *G01N 21/554* (2013.01); *G01N 15/0227* (2013.01); *G01N 15/1433* (2024.01);

(Continued)

(58) Field of Classification Search
CPC .......... G01N 15/0227; G01N 15/1434; G01N 2015/0038; G01N 21/554; G01N 21/6458;

(Continued)

(56) References Cited

U.S. PATENT DOCUMENTS

| | | | |
|---|---|---|---|
| 9,939,443 B2 | 4/2018 | Spetzler et al. |
| 10,557,847 B2 | 2/2020 | Weissleder et al. |

(Continued)

FOREIGN PATENT DOCUMENTS

| | | | | |
|---|---|---|---|---|
| CN | 110234600 A | * | 9/2019 | ............ B82Y 15/00 |
| WO | WO 2021/211756 | | 10/2021 | |

OTHER PUBLICATIONS

Chin et al., "Plasmonic Sensors for Extracellular Vesicle Analysis: From Scientific Development to Translational Research," ACS Nano, Nov. 2020, 14(11):14528-14548, 21 pages.

(Continued)

*Primary Examiner* — Tri T Ton
(74) *Attorney, Agent, or Firm* — Fish & Richardson P.C.

(57) ABSTRACT

Systems, methods, and devices are described herein for detecting and/or monitoring target extracellular vesicles ("EVs"), e.g., to detect and/or monitor cancer treatment, such as breast cancer, in a subject. The methods can include obtaining a nano-plasmonic array including nanostructures configured to amplify one or more specific wavelengths of electromagnetic radiation, flowing a liquid sample over the nano-plasmonic array, optionally labeling target EVs captured on the nano-plasmonic array with one or more reporter groups, projecting electromagnetic radiation onto the labeled target EVs captured on the nano-plasmonic array, and capturing an image of the target EVs by receiving electromagnetic radiation emitted, scattered, or reflected by the labeled target EVs or by reporter groups on the labeled target EVs.

17 Claims, 24 Drawing Sheets
(16 of 24 Drawing Sheet(s) Filed in Color)

Related U.S. Application Data

(60) Provisional application No. 63/391,999, filed on Jul. 25, 2022, provisional application No. 63/009,495, filed on Apr. 14, 2020.

(51) Int. Cl.

| | |
|---|---|
| *G01N 15/1433* | (2024.01) |
| *G01N 15/1434* | (2024.01) |
| *G01N 21/552* | (2014.01) |
| *G01N 21/64* | (2006.01) |
| *G01N 33/50* | (2006.01) |
| *G01N 15/00* | (2006.01) |
| *G01N 15/01* | (2024.01) |
| *G01N 15/10* | (2006.01) |
| *G01N 15/14* | (2006.01) |

(52) U.S. Cl.
CPC ..... *G01N 15/1434* (2013.01); *G01N 21/6458* (2013.01); *G01N 21/648* (2013.01); *G01N 33/5076* (2013.01); *G01N 2015/0038* (2013.01); *G01N 15/01* (2024.01); *G01N 2015/1006* (2013.01); *G01N 2015/1486* (2013.01)

(58) Field of Classification Search
CPC .. G01N 21/648; G01N 33/5076; G01N 15/01; G01N 15/1433; G01N 2015/1006; G01N 2015/1486; G01N 2021/6439; G01N 2021/6441; G01N 21/658; G01N 33/54373; G01N 33/57415; G06F 16/906; G06F 40/284; G06F 40/30; G06Q 30/0201; G06Q 30/0609; G06V 10/75; G10L 15/26
USPC ......................................................... 356/301
See application file for complete search history.

(56) References Cited

U.S. PATENT DOCUMENTS

| | | | |
|---|---|---|---|
| 10,712,343 | B2 | 7/2020 | Weissleder et al. |
| 2012/0184451 | A1 | 7/2012 | Singamaneni et al. |
| 2015/0024960 | A1 | 1/2015 | Lee et al. |
| 2015/0160246 | A1 | 6/2015 | Idelevich et al. |
| 2016/0334398 | A1* | 11/2016 | Weissleder .......... G01N 33/553 |
| 2017/0122951 | A1 | 5/2017 | Weissleder et al. |
| 2018/0372730 | A1 | 12/2018 | Braeckmans et al. |
| 2019/0003968 | A1* | 1/2019 | Osawa .......... G01N 21/6428 |
| 2019/0310172 | A1 | 10/2019 | Zhong et al. |
| 2019/0331605 | A1 | 10/2019 | Park et al. |
| 2020/0096516 | A1 | 3/2020 | Hu et al. |
| 2020/0141871 | A1 | 5/2020 | Chang et al. |
| 2020/0392219 | A1* | 12/2020 | Hoffman .......... C07K 14/70517 |
| 2021/0017607 | A1 | 1/2021 | Patnaik et al. |
| 2021/0172948 | A1 | 6/2021 | Duquenoy et al. |
| 2023/0160809 | A1 | 5/2023 | Im et al. |

OTHER PUBLICATIONS

Hong et al., "Poster: Plasmon-enhanced biosensing of tumor-derived extracellular vesicles in breast cancer," Poster, Presented at Proceedings of the Gordon Research Conference: Understanding Extracellular Vesicle Biogenesis and Composition for Detection and Treatment of Diseases, Newry, ME, Jul. 24-29, 2022, 1 page.
Im et al., "Nano-plasmonic exosome diagnostics," Expert Rev Mol Diagn., Jun. 2015, 15(6):725-733, 19 pages.
International Preliminary Report on Patentability in International Appln. No. PCT/US2021/027350, mailed Oct. 27, 2022, 7 pages.
International Search Report and Written Opinion in International Appln. No. PCT/US2021/027350, mailed Jul. 20, 2021, 9 pages.

Min et al., "Plasmon-Enhanced Biosensing for Multiplexed Profiling of Extracellular Vesicles," Advanced Biosystems, Dec. 2020, 4(12):e200003, 8 pages.
Ohannesian et al., "Commercial and emerging technologies for cancer diagnosis and prognosis based on exosomal biomarkers," Journal of Physics Photonics, Apr. 2020, 2(3): 16 pages.
Park et al., "Self-Assembly of Nanoparticle-Spiked Pillar Arrays for Plasmonic Biosensing," Advanced Functional Materials, 2019, 29(43):1904257, 23 pages (with Supporting Information).
Raghu et al., "Nanoplasmonic pillars engineered for single exosome detection," PLoS One, Aug. 2018, 13(8):e0202773, 13 pages.
Rojalin et al., "Nanoplasmonic Approaches for Sensitive Detection and Molecular Characterization of Extracellular Vesicles," Front. Chem., May 2019, 7(279): 24 pages.
Son et al., "Poster: Nano-plasmonic technology for high-throughput single extracellular vesicle analyses," Poster, Presented at Proceedings of the 21st Annual Innovative Molecular Analysis Technologies Principal Investigators Meeting, Virtual, Dec. 2-4, 2020, 1 page.
Van Deun et al., "Integrated Dual-Mode Chromatography to Enrich Extracellular Vesicles from Plasma," Adv Biosyst., Dec. 2020, 4(12):e1900310, 6 pages.
Wittenberg et al., "Facile Assembly of Micro- and Nanoarrays for Sensing with Natural Cell Membranes," ACS Nano, Aug. 2011, 5(9):7555-7564.
Wittenberg et al., "High-Affinity Binding of Remyelinating Natural Autoantibodies to Myelin-Mimicking Lipid Bilayers Revealed by Nanohole Surface Plasmon Resonance," Anal. Chem., Jun. 2012, 84(14):6031-6039.
Extended European Search Report in European Appln. No. 21789561.4, dated Aug. 16, 2023, 13 pages.
Im et al., "Label-free detection and molecular profiling of exosomes with a nano-plasmonic sensor," Nat Biotechnol., May 2014, 32(5):490-5, 9 pages.
Lv et al., "Label-Free Exosome Detection Based on a Low-Cost Plasmonic Biosensor Array Integrated with Microfluidics," Langmuir, Jul. 2019, 35(30):9816-9824.
Park et al., "Analyses of Intravesicular Exosomal Proteins Using a Nano-Plasmonic System," ACS Photonics, Feb. 2018, 5(2):487-494.
Im et al., "Novel nanosensing technologies for exosome detection and profiling," HHS Public Access Author Manuscript, doi: 10.1039/c71c00247e, published online Aug. 22, 2018; published in final edited form as: Lab Chip, Aug. 2017, 17(17):2892-2898, 13 pages.
Lane et al., "Extracellular vesicles as circulating cancer biomarkers: opportunities and challenges," Clin Transl Med., May 2018, 7:14, 11 pages.
Raimondo et al., "Role of Extracellular Vesicles in Hematological Malignancies," Biomed Res Int., 2015, 2015:821613, 9 pages.
Ricklefs et al., "Extracellular Vesicles from High-Grade Glioma Exchange Diverse Pro-oncogenic Signals That Maintain Intratumoral Heterogeneity," Cancer Res., May 2016, 76(10):2876-81.
Shao et al., "New Technologies for Analysis of Extracellular Vesicles," HHS Public Access Author Manuscript, doi: 10.1021/acs.chemrev. 7b00534, published online Aug. 28, 2018; published in final edited form as: Chem Rev., Feb. 2018, 118(4):1917-1950, 83 pages.
Zhang et al., "Multiplexed immunophenotyping of circulating exosomes on nano- engineered ExoProfile chip towards early diagnosis of cancer," Chem Sci., Apr. 2019, 10(21):5495-5504.
International Search Report and Written Opinion in International Appln. No. PCT/US2023/070948, mailed Dec. 26, 2023, 19 pages.
International Preliminary Report on Patentability in International Appln. No. PCT/US2023/070948, mailed on Feb. 6, 2025, 16 pages.
International Search Report and Written Opinion in International Appln. No. PCT/US2024/061166, mailed on Feb. 19, 2025, 10 pages.
Office Action in Japanese Appln. No. 2022-562591, mailed on Feb. 25, 2025, 15 pages (with English translation).
Office Action in European Appln. No. 21789561.4, mailed on Aug. 12, 2025, 9 pages.
Daaboul et al., "Digital detection of exosomes by interferometric imaging," Scientific Reports, Nov. 2016, 6(1):37246, 10 pages.

(56)  References Cited

OTHER PUBLICATIONS

Im et al., "Label-free detection and molecular profiling of exosomes with a nano- plasmonic sensor," Nature Biotechnology, May 2014, 32(5):490-5 (Author Manuscript Only).

Liang et al., "Nanoplasmonic quantification of tumour-derived extracellular vesicles in plasma microsamples for diagnosis and treatment monitoring, " Nature Biomedical Engineering, Feb. 2017, 1(4):0021, 24 pages (Author Manuscript Only).

Yang et al., "Multiparametric plasma EV profiling facilitates diagnosis of pancreatic malignancy," Science Translational Medicine, May 2017, 9(391): eaal3226, 23 pages (Author Manuscript Only).

* cited by examiner

| EV capture | EV immunolabeling | Fluorescent EV imaging | Image analysis |

EV capture — Biotinylated EV, Avidin β, SH-Biotin-PEG, Au nanoholes

EV immunolabeling — Antibody

Fluorescent EV imaging — Target 1, Target 2, Target 3

$|E/E_0|^2$  0 — 100

Water

Au $z\ (\mu m)$  0.2, 0

$|E/E_0|^2$  0 — 400

Glass    nPLEX-FL

[100, 500]    [250, 2500]

Distribution (%)

Glass
nPLEX-FL

Intensity (a.u.)    $10^1$    $10^2$    $10^3$    $10^4$

Intensity ($\times 10^3$, a.u.)

Glass    nPLEX-FL

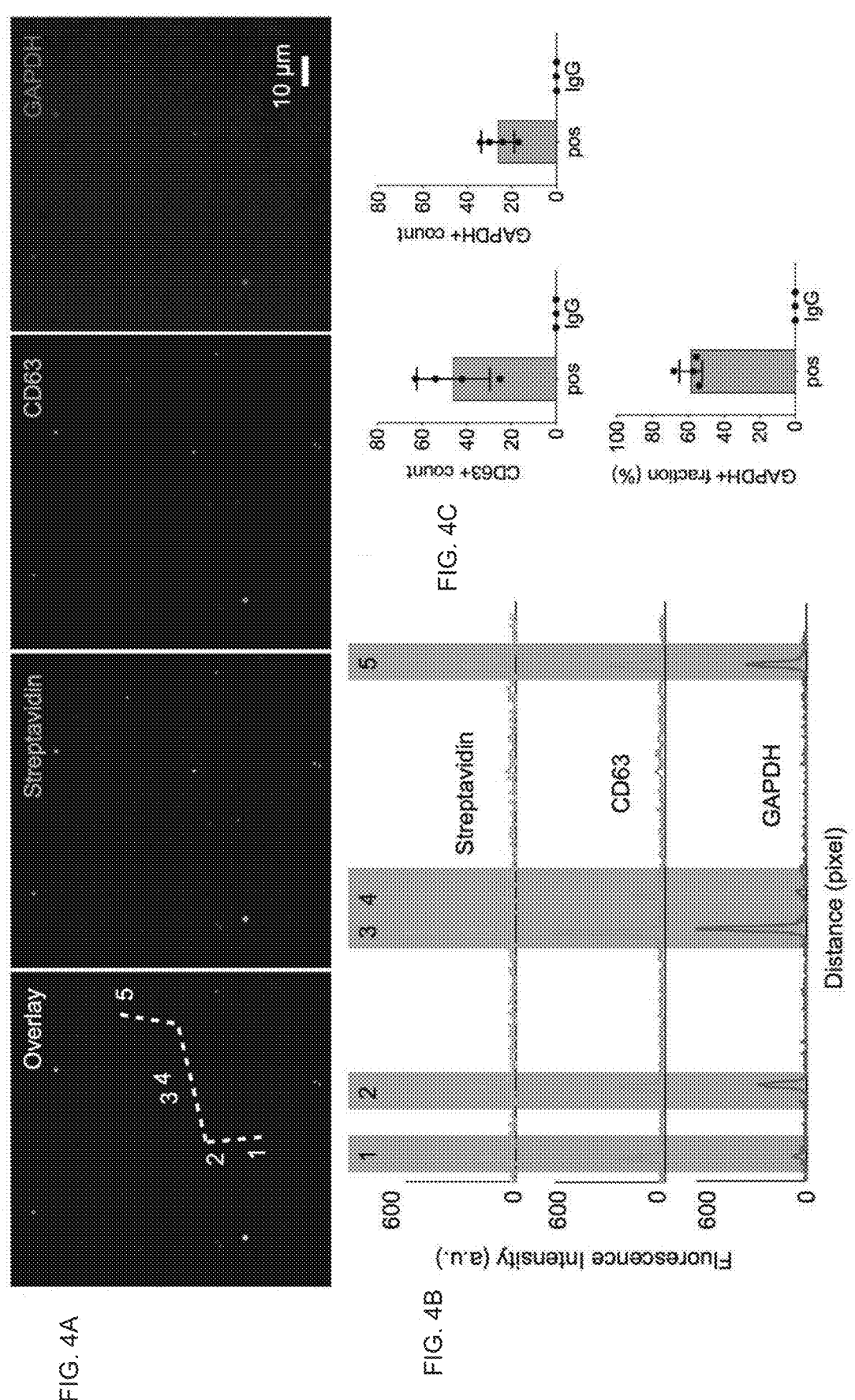

Gli36-WT
(EGFR+)

Ili36-EGFRvIII
(EGFR+)

Gli36-WT
(EGFRvIII-)

Gli36-EGFRvIII
(EGFRvIII+)

EGFR (175 kDa)

GAPDH (37 kDa)

Gli36-WT

Gli36-EGFRvIII

MCF-7

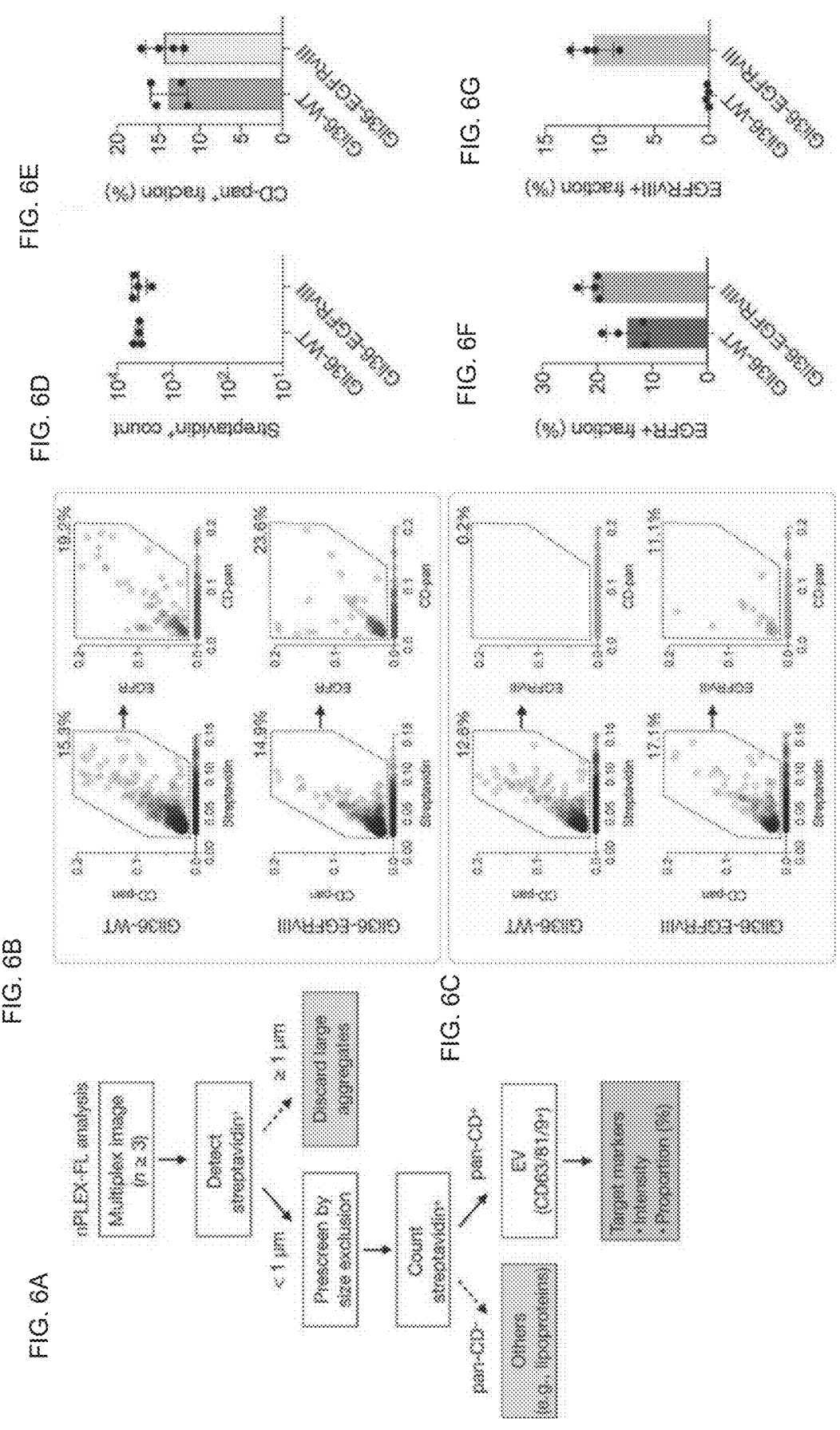

Si mold

1. Imprint

Resist

Glass

2. Patterning

Gold nanorod

3. Au deposition and lift-off

EV

4. EV detection

FIG. 11A
FIG. 11B
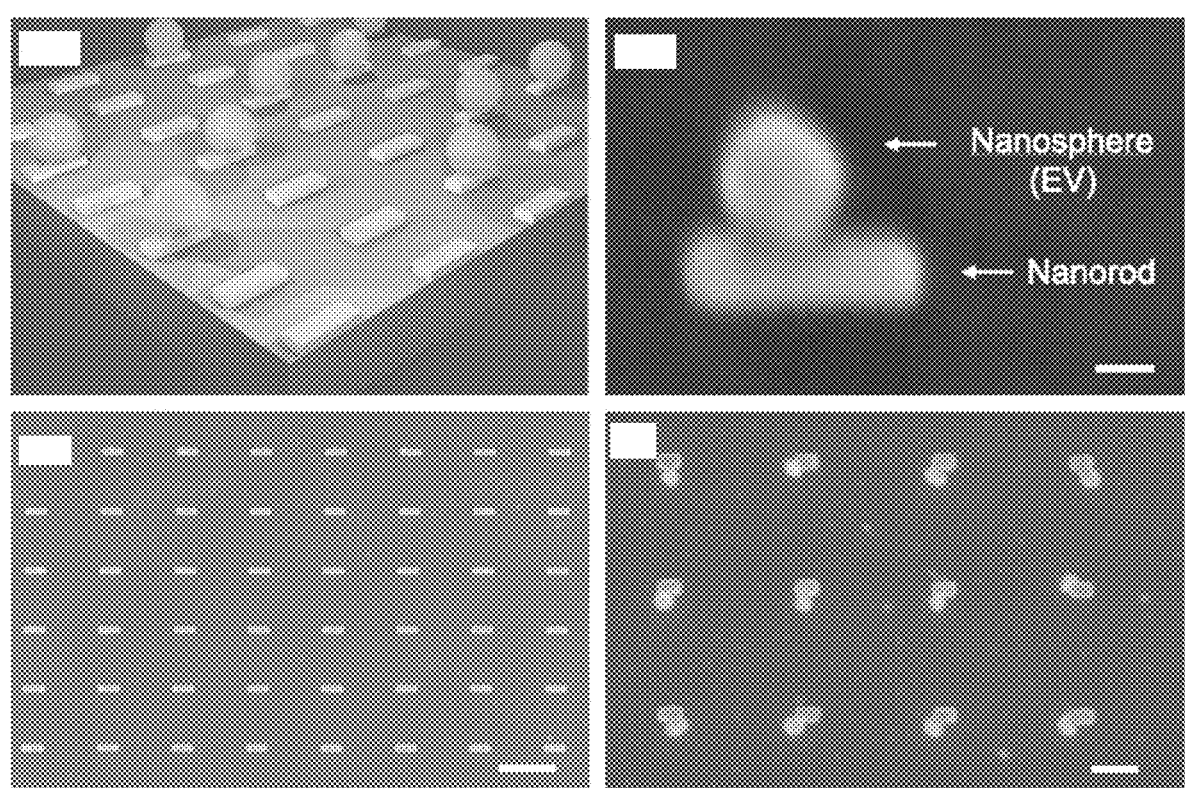
FIG. 11C
FIG. 11D
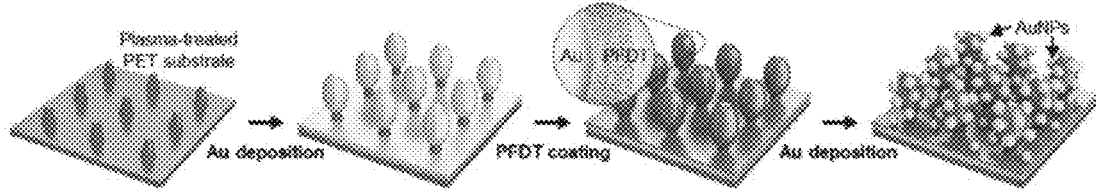
FIG. 11E-a

FIG. 11E-b         FIG. 11E-c         FIG. 11E-d
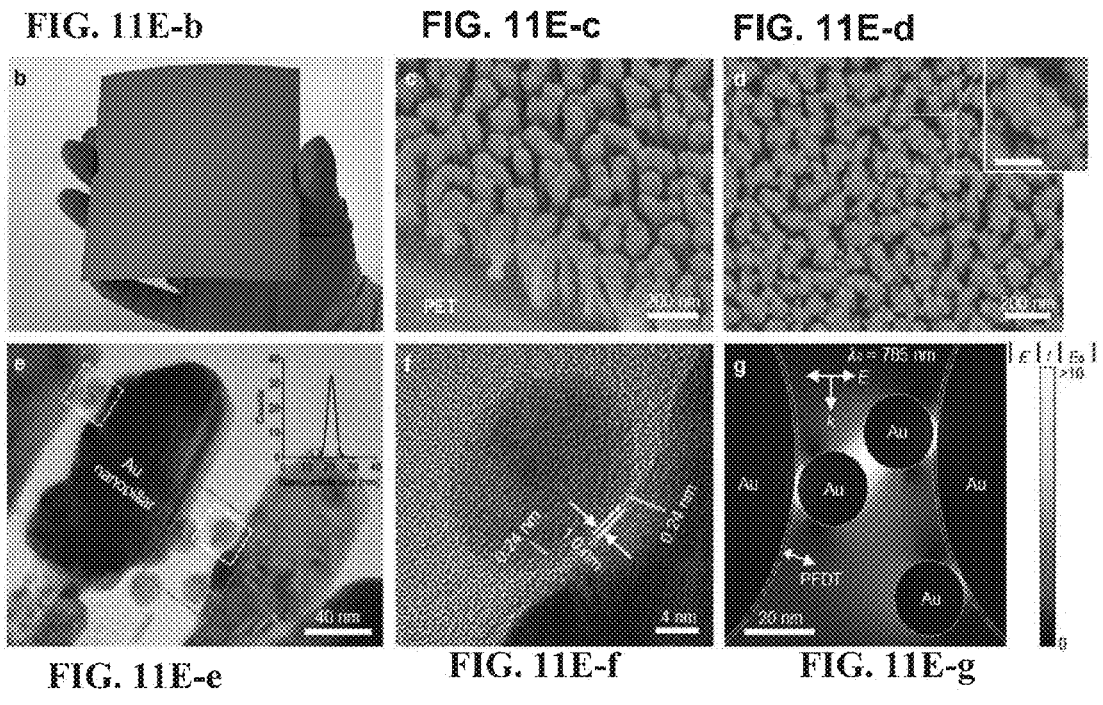
FIG. 11E-e         FIG. 11E-f         FIG. 11E-g
FIG. 12A
FIG. 12B
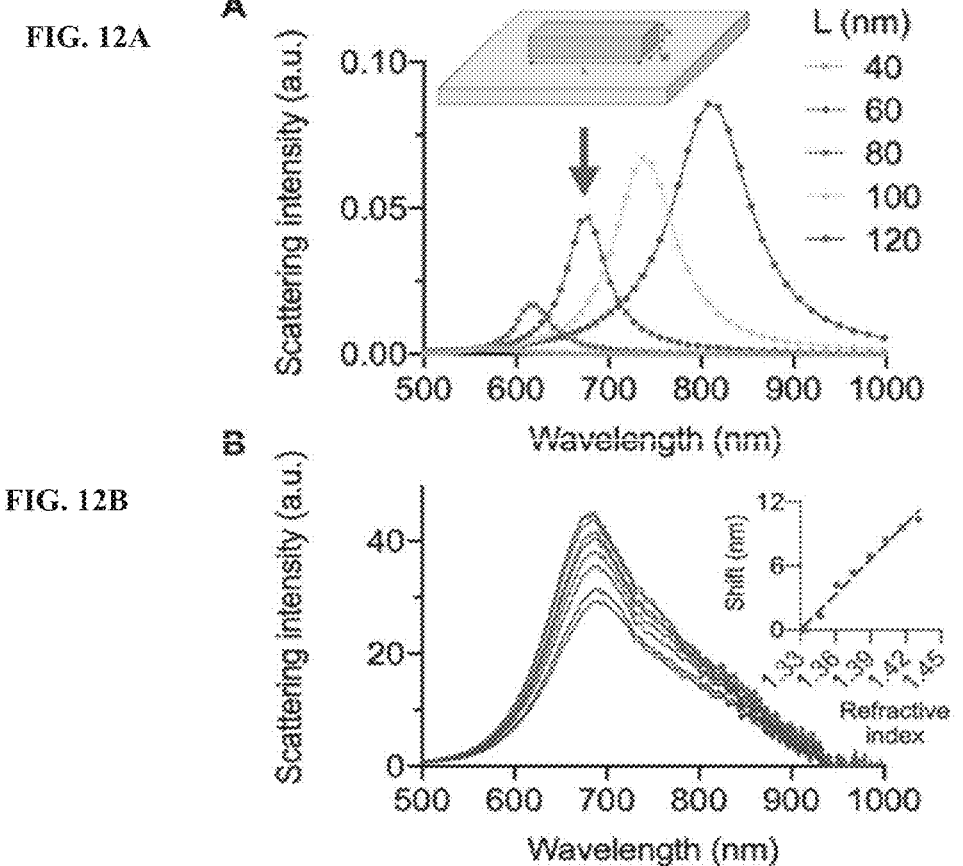

Side view

Top view

Nanodisk

Top view

Nanorod

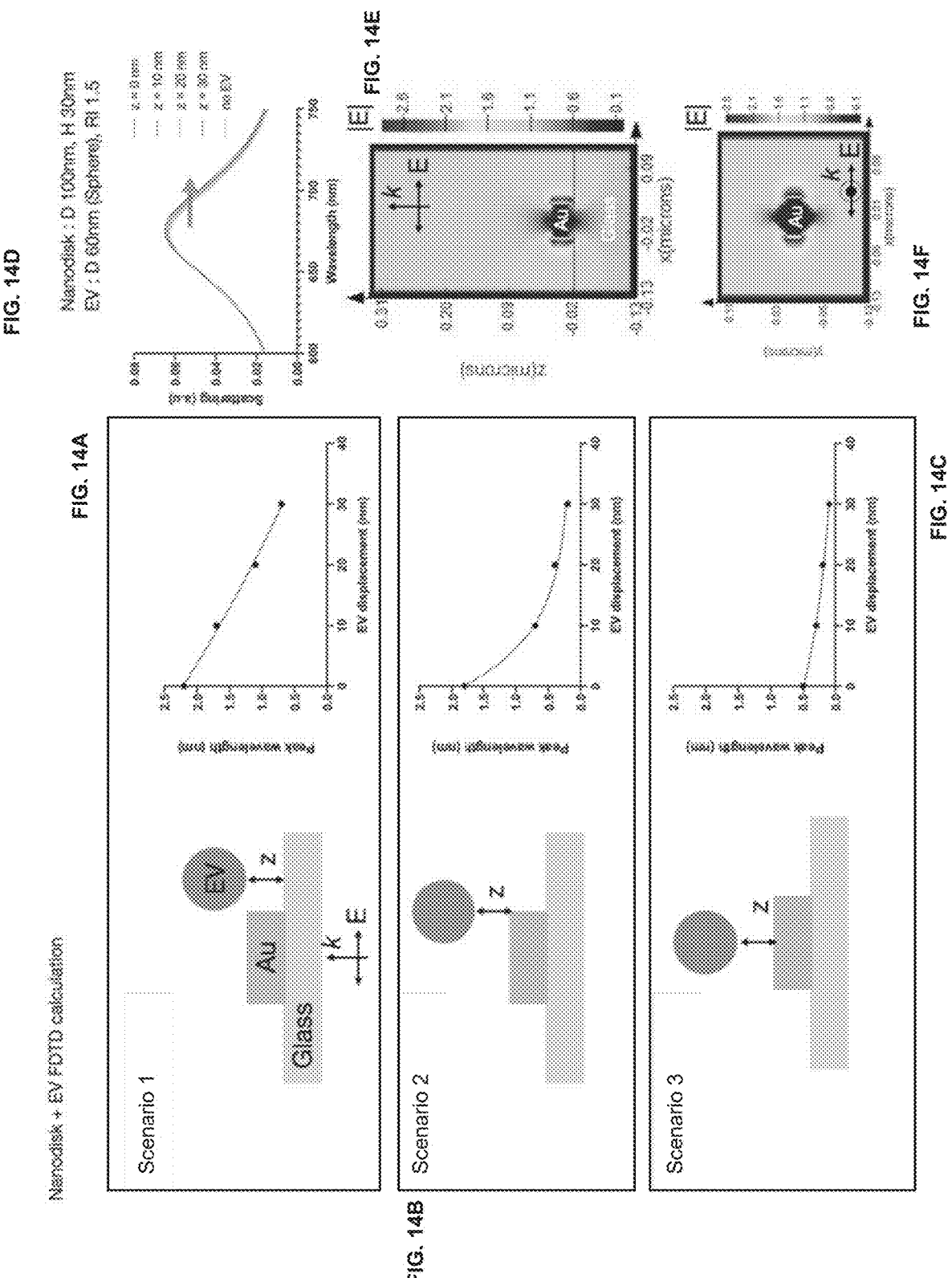

FIG. 18A
Dark
FIG. 18B
TRICT
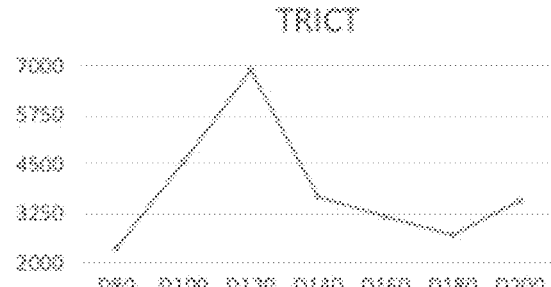
FIG. 18C
Cy5
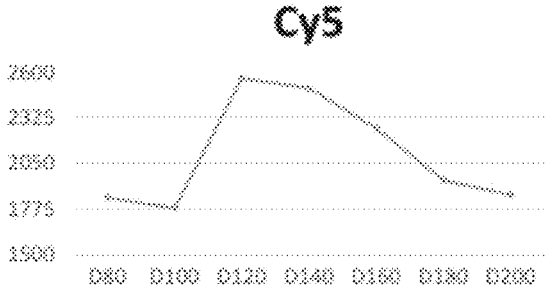
FIG. 18D
Cy5.5
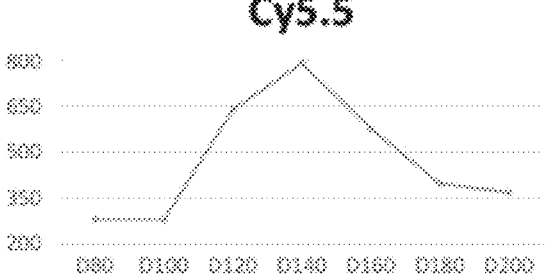
FIG. 19A
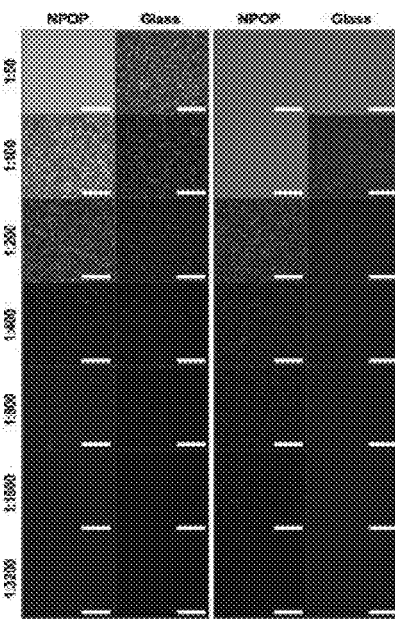
FIG. 19B
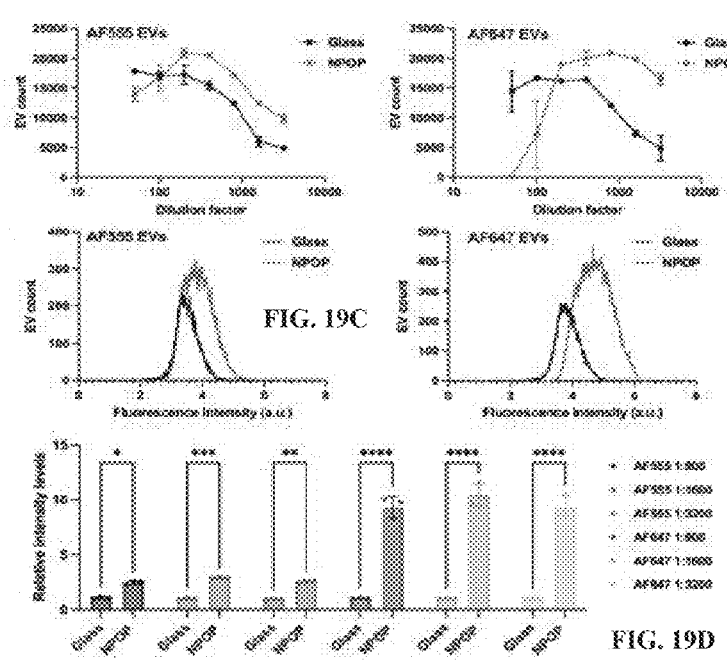
FIG. 19C
FIG. 19D

FIG. 21A
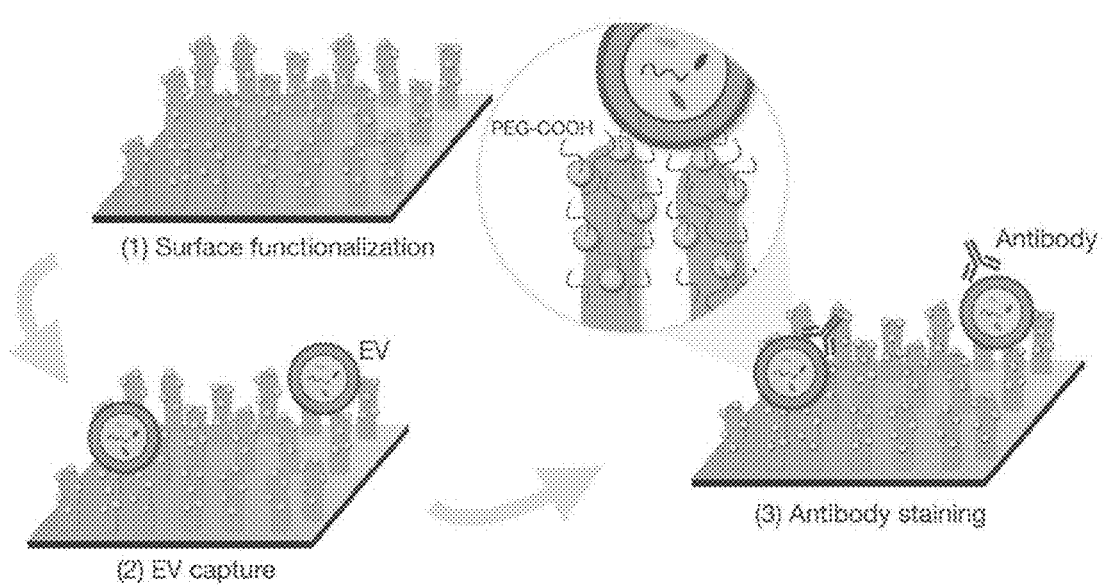
FIG. 21B                  FIG. 21C
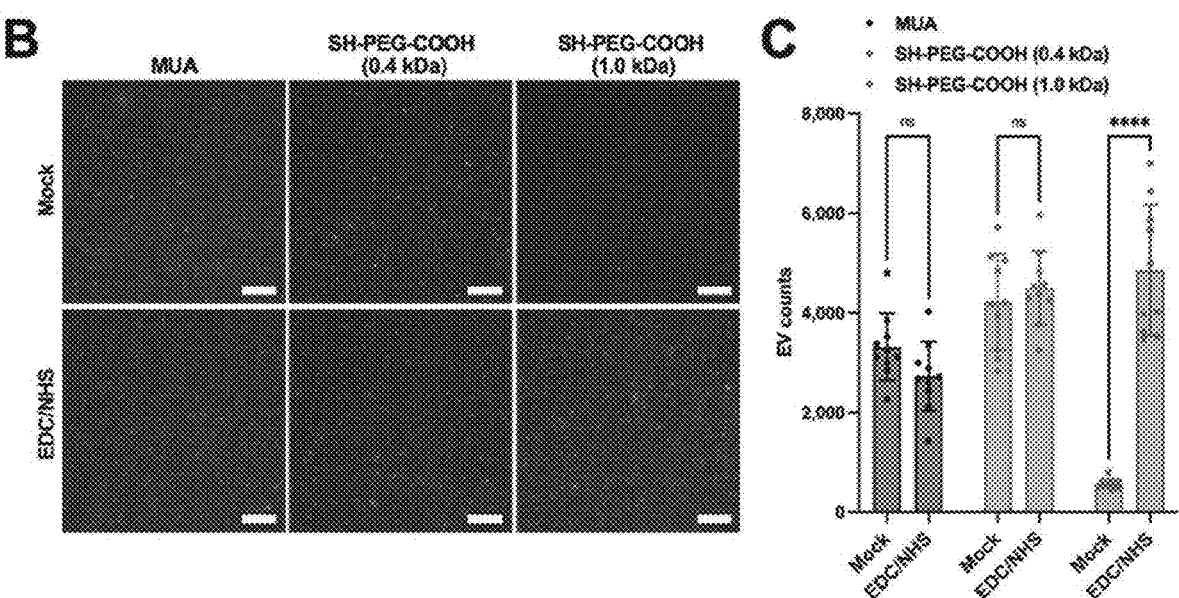

METHODS AND SYSTEMS OF ENHANCING ELECTROMAGNETIC RADIATION SIGNALS FROM EXTRACELLULAR VESICLES

CROSS-REFERENCE TO RELATED APPLICATIONS

This application claims the benefit of U.S. Provisional Patent Application Ser. No. 63/391,999, filed on Jul. 25, 2022. This application is also a continuation-in-part application of and claims the benefit of priority to International Patent Application No. PCT/US2021/027350, filed on Apr. 14, 2021, which claims the benefit of U.S. Provisional Patent Application Ser. No. 63/009,495, filed on Apr. 14, 2020. The entire contents and disclosures of all of these applications are hereby incorporated by reference in the disclosure of the present application.

This invention was made with government support under Grant Nos. R00CA201248 and R21CA217662, awarded by National Cancer Institute at the National Institute of Health. The government has certain rights in the invention.

TECHNICAL FIELD

This invention relates to methods of enhancing electromagnetic radiation, e.g., optical, signals of extracellular vesicles, and more particularly to a small number of extracellular vesicles.

BACKGROUND

Extracellular vesicles (EVs) present new opportunities as circulating biomarkers for cancers, cardiovascular, neurodegenerative, and infectious diseases among others. These cell-derived phospholipid vesicles are abundantly present in various bodily fluids (e.g., blood, cerebrospinal fluid, urine, saliva). More importantly, they carry a variety of biomolecules (lipids, proteins, and genetic materials) originating from their parental cells, which can be harnessed as a minimally invasive means to probe the molecular status of their cellular origins.

In further exploiting EVs' potential and accelerating their clinical adaptation, a critical unmet need is to develop sensitive, robust, and standardized assays that can determine the composition and molecular profiles of EVs in clinical samples. However, their unique sizes (50-1000 nm) impose technical challenges in conventional analytical methods, which often lead to variable findings. Flow cytometry, for example, often underestimate EV counts; small EVs (i.e., exosomes, typically smaller than 200 nm) could be missed due to their weak light scattering, or a group of vesicles could be counted as a single event. Conventional methods, particularly for protein analyses (e.g., Western blotting, enzyme-linked immunosorbent assay/ELISA), consume large amounts of samples and involve time-consuming and extensive processing steps, making them impractical for clinical scenarios. Developing new molecular platforms for EVs is thus a pivotal mandate to translate EVs as clinically relevant biomarkers.

SUMMARY

The present disclosure relates to signal amplification strategies to boost electromagnetic radiation signals, e.g., optical signals, generated from limited amounts of biomolecules present in individual EVs. In particular, the strong optical resonance of metallic nanostructure, e.g., gold or silver nanostructures, can be used to boost an optical signal to significantly amplify optical signals, e.g., fluorescent signals, emitted from EVs. Since the plasmon enhancement is an intrinsic signal amplification method, in certain embodiments, this intrinsic method is combined with other chemical amplification strategies (e.g., branched DNA barcodes) to improve the sensitivity even further. The present disclosure relates to methods and systems for enhancing optical signals of EVs.

The present disclosure also relates to methods of using plasmonic substrates that can be fabricated on a wafer-scale to amplify fluorescent-labeled EVs' signals for multi-channel single EV analysis, without the need for additional chemical or enzymatic signal amplification processes. The multiplexed single EV molecular profiling methods provide a better understanding of the heterogeneity of EVs with higher EV detection sensitivity and accuracy than past methods. These methods also enable the discrimination of individual EVs based on their cellular origins (i.e., EVs from, for example, tumor, breast, brain, or immune systems).

According to a first aspect, the present disclosure provides methods of enhancing an electromagnetic radiation signal, e.g., an optical signal, from a target extracellular vesicle (EV) on a substrate, the method comprising: obtaining a nano-plasmonic array comprising, a substrate, a plurality of nanostructures, and one or more affinity ligands fixed on or adjacent to the nanostructures, wherein the affinity ligands specifically bind to EVs to bind the EVs to the nanostructures or to the substrate adjacent to the nanostructures; flowing a liquid sample over the nano-plasmonic array at a flow rate that enables EVs in the liquid sample, if any, to bind to the affinity ligands thus capturing the EVs on the nano-plasmonic array; labeling target EVs among EVs captured on the nano-plasmonic array with one or more different reporter groups; exposing the labeled target EVs captured on the nano-plasmonic array to a first electromagnetic radiation thereby causing the target EVs and/or reporter groups on the target EVs to emit, scatter, or reflect the first electromagnetic radiation or a second electromagnetic radiation as an electromagnetic radiation signal; and receiving all or a portion of the electromagnetic radiation signal, wherein the nanostructures in the nano-plasmonic array are arranged and dimensioned to amplify the electromagnetic radiation signal, thereby enhancing the electromagnetic radiation signal from a target EV on the substrate.

In some embodiments of these methods, the one or more affinity ligands bind non-specifically to at least one surface marker on the EVs and/or to at least one intravesicular marker inside the EVs, and the reporter groups are bound to capture agents that specifically bind to at least one surface marker on the target EVs and/or to at least one intravesicular marker inside the target EVs, or the one or more affinity ligands specifically bind to at least one surface marker on the target EVs and/or to at least one intravesicular marker inside the target EVs, and the reporter groups are bound to capture agents that bind to at least one surface marker on the target EVs and/or to at least one intravesicular marker inside the target EVs, either specifically or non-specifically.

In certain embodiments, the plurality of nanostructures are arranged to form a periodic array of nanostructures on the substrate, wherein the periodic array of nanostructures is arranged and dimensioned to amplify the electromagnetic radiation signals emitted, scattered, or reflected by EVs bound to the nanostructures and/or EVs bound to the substrate near the nanostructures, or to amplify the electromagnetic radiation signals emitted, scattered, or reflected by reporter groups attached to the EVs.

In various embodiments, the electromagnetic radiation signal can be or include a fluorescent signal, a Raman signal, or dark-field scattering, and the methods can further include obtaining an image of the amplified electromagnetic radiation signal, e.g., optical signal.

In another aspect, this disclosure provides methods of detecting or monitoring cancer, wherein the liquid sample used in the methods described herein is from a subject, wherein the reporter groups are bound to capture agents that specifically bind to tumor-derived target EVs, and wherein the method further comprises analyzing the obtained image to detect whether the liquid sample comprises tumor-derived target EVs, thereby detecting or monitoring cancer in the subject.

In certain embodiments, these methods can further include identifying EVs by size and discarding any EVs or other components larger than one micron; selecting target EVs from the identified EVs based on positivity for target EV markers to generate selected target EVs; specifying selected target EVs as originating from specific organs or tissues by positivity for organ- or tissue-specific markers to generate specific, selected target EVs; and analyzing individual specific, selected target EVs based on tetraspanin biomarkers on the surface of the specific target EVs, based on intravesicular biomarkers within the specific target EVs, or based on both tetraspanin and intravesicular biomarkers.

In the methods described herein, the reporter groups can be, include, or consist of, a first fluorescent label, and the reporter groups can be, include, or consist of antibodies that specifically bind to a biomarker on the surface of the target EVs. For example, in some embodiments, the antibodies can be, include, or consist of at least two different types of antibodies, wherein antibodies of a first type bind to EpCAM and antibodies of a second type bind to HER2. In other embodiments, the antibodies can be, include, or consist of at least four different types of antibodies, wherein antibodies of a first type bind to MUC1, antibodies of a second type bind to EGFR, antibodies of a third type bind to EpCAM, and antibodies of a fourth type bind to HER2.

In some embodiments, the methods further include labeling target EVs that include the first fluorescent label with a second fluorescent label that is different from the first fluorescent label. In some embodiments of the methods described herein, the cancer can be or include breast cancer.

In another aspect, this disclosure provides methods of detecting cancer in a subject, the methods including collecting a biological sample from the subject; isolating EVs from the biological sample; capturing EVs on a nano-plasmonic array, wherein the nano-plasmonic array includes, a substrate, a plurality of nanostructures, and one or more affinity ligands fixed on or adjacent to the nanostructures, wherein the affinity ligands specifically bind to EVs to bind the EVs to the nanostructures or to the substrate adjacent to the nanostructures; immunolabeling target EVs among the captured EVs with multiple different fluorescent reporter groups; conducting multichannel fluorescence imaging to form an image; and analyzing the image to detect cancer in the subject.

In these methods, the plurality of nanostructures can be arranged, in certain embodiments, to form a periodic array of nanostructures on the substrate, wherein the periodic array of nanostructures is arranged and dimensioned to amplify fluorescent signals emitted, scattered, or reflected by EVs bound to the nanostructures and/or EVs bound to the substrate near the nanostructures, or to amplify fluorescent signals emitted, scattered, or reflected by reporter groups attached to the EVs.

In some embodiments, the immunolabeling is carried out with different antibodies that are bound to different reporter groups and that specifically bind to different biomarkers on the surface of the target EVs. For example, herein the antibodies can be, include, or consist of at least two different types of antibodies, wherein antibodies of a first type bind to EpCAM and antibodies of a second type bind to HER2. In other embodiments, the antibodies can be, include, or consist of at least four different types of antibodies, wherein antibodies of a first type bind to MUC1, antibodies of a second type bind to EGFR, antibodies of a third type bind to EpCAM, and antibodies of a fourth type bind to HER2. In some embodiments, the cancer is breast cancer.

In another aspect, the disclosure provides methods of detecting individual target EVs relevant to cancer diagnosis or cancer treatment monitoring, the methods including: providing a biological sample from a subject containing one or more EVs; capturing the one or more EVs on a nano-plasmonic array, wherein the nano-plasmonic array includes a substrate, a plurality of nanostructures, and one or more affinity ligands fixed on or adjacent to the nanostructures, wherein the affinity ligands specifically bind to EVs to bind the EVs to the nanostructures or to the substrate adjacent to the nanostructures; immunolabeling target EVs among the captured EVs with fluorescence-conjugated biomolecules; conducting multi-channel fluorescence imaging to form an image; and analyzing the image to detect cancer in a subject or monitor a cancer treatment in a subject undergoing the cancer treatment.

In these methods, the fluorescence-conjugated biomolecules can be, include, or consist of at least three fluorescent molecules conjugated to at least three cancer-associated biomolecules. For example, in certain embodiments, the fluorescence-conjugated biomolecules can be, include, or consist of fluorescence-conjugated wheat germ agglutinin.

In some embodiments, the nano-plasmonic array is configured to enhance a fluoresce signal from the fluorescence-conjugated biomolecules at least two-fold compared to a fluorescence signal from an image taken using a glass substrate instead of the nano-plasmonic array.

In another aspect, the present disclosure provides methods of cancer diagnosis or treatment monitoring, the method including: providing a biological sample from a subject containing one or more extracellular vesicles (EVs); contacting at least a first portion of the biological sample with a surface conjugated with a first EV-specific antibody and labeling with a first fluorescence-conjugated biomolecule; contacting at least a second portion of the biological sample with a surface conjugated with a second EV-specific antibody and labeling with a second fluorescence-conjugated biomolecule; contacting at least a third portion of the biological sample with a surface conjugated with a second EV-specific antibody and labeling with a third fluorescence-conjugated biomolecule; conducting multi-channel fluorescence imaging to form an image; and analyzing the image to detect cancer in a subject or monitor a cancer treatment in a subject undergoing the cancer treatment.

In these methods, the surface can be, include, or consist of a nano-plasmonic array, wherein the nano-plasmonic array includes or consists or a substrate, a plurality of nanostructures, and one or more affinity ligands fixed on or adjacent to the nanostructures, wherein the affinity ligands specifically bind to EVs to bind the EVs to the nanostructures or to the substrate adjacent to the nanostructures.

In some embodiments, the nano-plasmonic arrays are configured to enhance a fluoresce signal in the image at least two-fold compared to a fluorescence signal from an image taken using a glass substrate instead of the nano-plasmonic array.

In other aspects, the present disclosure provides nano-plasmonic arrays for detecting target extracellular vesicles (EVs), the arrays including or consisting of a substrate; a plurality of nanostructures arranged to form a periodic array of nanostructures on the substrate, wherein the periodic array of nanostructures is arranged and dimensioned to amplify one or more optical signals of electromagnetic radiation emitted, scattered, or reflected by EVs bound to the nanostructures and/or EVs bound to the substrate near the nanostructures, or to amplify one or more optical signals of electromagnetic radiation emitted, scattered, or reflected by reporter groups attached to the EVs; and one or more affinity ligands fixed on or adjacent to the nanostructures, wherein the affinity ligands selectively bind to target EVs to bind the target EVs to the nanostructures or to the substrate adjacent to the nanostructures.

In various embodiments, the optical signal can be one or more of a fluorescent signal, a Raman signal, or dark-field scattering.

In certain embodiments, the nanostructures can be or include or consist of a plurality of nanoholes arranged in an array and formed in the substrate or in a metal film disposed on the substrate. In other embodiments, the nanostructures can be or include or consist of a plurality of nanoholes, nanowells, nanorods, nanodisks, nanopillars, nanogrooves, or any combinations thereof, arranged in an array on a top surface of the substrate. The nanostructures can be, for example, gold nanoparticles (NPs) bound to gold nanopillars (NPs on nanopillars, or "NPOP") structures.

In some embodiments, each of the nanostructures has a maximum size, e.g., diameter, width, or length, of about 30 to 400 nm. For example, the nanostructures can be nanorods or nanosquares and have dimensions of about 50 to about 300 nm in length, about 20 to about 300 nm in width, and about 20 to about 300 nm in height, or the nanostructures can be nanodisks and have dimensions of about 50 to about 200 nm in diameter and about 20 to about 300 nm in height. Each of the nanopillars can have a maximum size of about 30 to about 500 nm.

In certain embodiments, the periodic array of nanostructures has a periodicity of about 400 to 800 nm or 400 to 2000 nm between nanostructures. In certain embodiments, the nanostructures are nanopillars having a dimension of about 20 to about 500 nm in diameter and about 20 to about 300 nm in height with a density of about 300 to about 750 nanopillars per $\mu m^2$ on a substrate (e.g., Si, glass, indium tin oxide/ITO, polyethylene terephthalate (PET) polymer substrate).

In some embodiments, the affinity ligands bind to a capture agent, e.g., an antibody, wherein the capture agent is configured to bind to at least one surface marker on the target EV In certain embodiments, the affinity ligand is configured to bind to at least one surface marker on the target EV and/or to at least one intravesicular marker inside the target EV.

In some embodiments, the nano-plasmonic arrays further include or consist of a metal film disposed on a top surface of the substrate, wherein the metal film comprises a plurality of nanoholes that penetrate the metal film in a periodicity selected to amplify one or more specific wavelengths of electromagnetic radiation, wherein the periodicity of about 400 to 800 nm between nanoholes, wherein the metal film comprises a plurality of affinity ligands fixed on or adjacent to the nanoholes, and wherein the plurality of affinity ligands selectively bind to markers on surfaces of the target EVs.

The metal film can be or include, for example, a noble metal, a transition metal, an alkali metal, or any combination thereof. In various implementations, either or both the nanostructures and the metal film are, or include, or consist of gold, silver, aluminum, or platinum.

In another aspect, the disclosure includes methods for detecting target extracellular vesicles (EVs) in a liquid sample, the methods including or consisting of obtaining a nano-plasmonic array as described or claimed herein; flowing a liquid sample over the nano-plasmonic array at a flow rate that enables the EVs in the liquid sample, if any, to bind to the affinity ligands thus capturing the EVs on the nano-plasmonic array; labeling target EVs captured on the nano-plasmonic array with one or more reporter groups; projecting a first electromagnetic radiation at one or more specific wavelengths onto the labeled target EVs captured on the nano-plasmonic array, wherein the electromagnetic radiation at the one or more specific wavelengths is selected to cause the reporter groups to emit, scatter, or reflect the first electromagnetic radiation or a second electromagnetic radiation; receiving the first or second electromagnetic radiation emitted, scattered, or reflected by the reporter groups, wherein the nano-plasmonic array of nanostructures is arranged and dimensioned to amplify the first or second electromagnetic radiation emitted, scattered, or reflected by the reporter groups; and capturing an image of the amplified first or second electromagnetic radiation emitted, scattered, or reflected by the reporter groups.

In the methods disclosed herein, the number of the target EVs may be less than 1,000.

In certain embodiments, the nanostructures include a plurality of nanoholes that penetrate the substrate or a metal film disposed on the substrate, or the nanostructures include or consist of a plurality of nanorods, nanodisks, nanopillars, nanogrooves, or any combination thereof, arranged on a top surface of the substrate.

In some embodiments the methods as described herein further include or consist of identifying EVs by size and discarding large components, e.g., larger than one micron; selecting target EVs from the identified EVs based on positivity for target EV markers; selecting target EVs as originating from specific organs or tissues by positivity for organ- or tissue-specific markers to generate specific target EVs; and analyzing individual specific target EVs based on extravesicular biomarkers on the surface of the specific target EVs and/or based on intravesicular biomarkers within the specific target EVs.

In yet another aspect, the disclosure provides systems for detecting target extracellular vesicles (EVs) in a liquid sample, the systems including or consisting of a nano-plasmonic array as described and claimed herein; a sample control unit comprising a pump; at least one fluidic channel configured to flow a liquid sample over the nano-plasmonic array at a flow rate controlled by the pump that enables the EVs in the liquid sample, if any, to bind to the affinity ligands thus capturing the EVs on the nano-plasmonic array; and at least one capture agent, e.g., an antibody, bound to a reporter group to label target EVs captured on the nano-plasmonic array with one or more reporter groups; and an imaging unit comprising a light source configured to project electromagnetic radiation onto the labeled target EVs captured on the nano-plasmonic array; and an electromagnetic radiation detector, e.g., a camera or CCD, configured to receive electromagnetic radiation emitted, scattered, or reflected by the target EVs or reporter groups on the labeled target EVs captured on the nano-plasmonic array, and to capture an image of the labeled target EVs, wherein the electromagnetic radiation emitted, scattered, or reflected by scattered light reflected from the reporter groups has one or more wavelengths amplified by the periodic array of nano-structures.

In some embodiments of these systems, the nanostructures include or consist of a plurality of nanoholes arranged in an array and formed in the substrate or in a metal film disposed on the substrate. In other embodiments, the nano-structures include or consist of a plurality of nanorods, nanodisks, or nanogrooves arranged in an array on a top surface of the substrate.

In some embodiments, the affinity ligands bind to a capture agent, wherein the capture agent is configured to bind to at least one surface marker on the target EV In other embodiments, the affinity ligand is configured to bind to at least one surface marker on the target EV and/or to at least one intravesicular marker inside the target EV.

In some embodiments, the methods are used to detect tumor-derived EVs using a QUAD marker signature (Mucin 1, cell surface associated (MUC1), Epidermal Growth Factor Receptor (EGFR), epithelial cellular adhesion molecule (EpCAM), and human epidermal growth factor receptor 2 (HER2)), e.g., EVs derived from breast tumors. These methods can include treatment monitoring during chemotherapy to change a course of therapy during ongoing therapy, e.g., using markers HER2 and EpCAM.

Certain terms employed with this document are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" comprise plural referents unless context clearly indicates otherwise. Similarly, the word "or" is intended to include "and" unless the context clearly indicates otherwise. The abbreviation, "e.g." is used herein to indicate a non-limiting example.

The term "periodicity," as used herein, refers to a recurrence or repetition of a nanostructure at regular intervals by their positioning on the nanostructure. The term "periodic" as used herein therefore refers to the regular predefined pattern of nanostructures with respect to each other, such as a lattice or other repeating unit configuration. A random distribution of nanostructures is a periodic pattern.

"Surface plasmon resonance (SPR)," as used herein, refers to the physical phenomenon in which incident light stimulates collective resonant electron oscillations at planar metal surfaces, and in particular at interfaces between negative and positive permittivity materials stimulated by incident light.

The term "localized surface plasmon resonance (LSPR)" refers to surface plasmon resonance of nanometer-sized structures, such as a metallic nanoparticle. The oscillating electrons produce strong electromagnetic fields in the (non-conducting) ambient medium near the surface of the metal.

As used herein, "surface plasmons," "surface plasmon polaritons," or "plasmons" refer to the collective oscillations of free electrons at plasmonic surfaces, such as metals.

These oscillations result in self-sustaining, surface electromagnetic waves that propagate in a direction parallel to the metal/dielectric (or metal/vacuum) interface. Because the wave is on the boundary of a metal and the external medium (air or water for example), these oscillations are very sensitive to any refractive index change of this boundary, such as, for example, the adsorption of a molecular target, such as an EV, to the metal surface. Additionally, the electromagnetic field strength decays exponentially from the metal surface to the surrounding environment (e.g., vacuum or dielectric). A maximum value of the electromagnetic field strength can be found at the metal/dielectric or metal/vacuum interface.

As used herein, the term "sample" means any biological or other fluids that may contain one or more extracellular vesicles (e.g., exosomes). Such biological fluids include, without limitation, fluids derived from or containing cells, organisms (bacteria, viruses), lysed cells or organisms, cellular extracts, nuclear extracts, components of cells or organisms, extracellular fluid, media in which cells or organisms are cultured in vitro, blood, plasma, serum, gastrointestinal secretions, ascites, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, pleural fluid, nipple aspirates, breast milk, external sections of the skin, respiratory, intestinal, and genitourinary tracts, and prostatic fluid. A sample can be a viral or bacterial sample, a sample obtained from an environmental source, such as a body of polluted water, an air sample, or a soil sample, as well as a food industry sample.

A "biological sample" is derived or obtained from a living organism. The organism can be a whole organism or can be cells or organs grown in culture. In one embodiment, a "biological sample" also refers to a cell or population of cells or a quantity of tissue or fluid from a subject. Most often, a sample has been removed from a subject, but the term "biological sample" can also refer to cells or tissue analyzed in vivo, i.e., without removal from the subject. Often, a "biological sample" will contain cells from a subject, but the term can also refer to non-cellular biological material, such as non-cellular fractions of blood, saliva, or urine. In one embodiment, a biological sample is from a resection, bronchoscopic biopsy, or core needle biopsy of a primary, secondary, or metastatic tumor, e.g., breast, ovarian, pancreatic, biliary tract, colorectal, glioblastoma, lung tumors or a cell block from pleural fluid. In addition, fine needle aspirate biological samples are also useful. In one embodiment, a biological sample includes primary ascites cells.

Biological samples also include explants and primary and/or transformed cell cultures derived from patient tissues. A biological sample can be provided by removing a sample of cells from a subject, but can also be accomplished by using previously isolated cells or cellular extracts (e.g., isolated by another person, at another time, and/or for another purpose). Archival tissues, such as those having treatment or outcome history may also be used. Biological samples include, but are not limited to, tissue biopsies, scrapes (e.g., buccal scrapes), whole blood or other bodily fluids, such as plasma, serum, urine, saliva, cell culture, urine, ascites, pleural fluid, Broncho Alveolar Lavage Fluid (BALF), or cerebrospinal fluid.

The samples analyzed by the compositions and methods described herein may have been processed for purification or enrichment of EVs contained therein.

As used herein, an "extracellular vesicle" ("EV") refers to a naturally occurring or synthetic vesicle that includes a cavity inside. The EVs comprise a lipid bilayer membrane enclosing contents of the internal cavity. An EV can include, but is not limited to, an ectosome, a microvesicle, a microparticle, an exosome, an oncosome, an apoptotic body, a liposome, a vacuole, a lysosome, a transport vesicle, a secretory vesicle, a gas vesicle, a matrix vesicle, or a multivesicular body. An EV has a dimension of up to about 10 microns, but are typically about 1000 nm or less.

Exosomes and microvesicles are types of EVs, and can be shed by eukaryotic cells, or budded off of the plasma membrane, to the exterior of the cell. These membrane-bound vesicles are heterogeneous in size with diameters ranging from about 10 nm to about 5000 nm. The methods and compositions described herein are equally applicable for microvesicles of all sizes.

In some of the literature, the term "exosome" also refers to protein complexes containing exoribonucleases that are involved in mRNA degradation and the processing of small nucleolar RNAs (snoRNAs), small nuclear RNAs (snRNAs) and ribosomal RNAs (rRNA). Such protein complexes do not have membranes and are not "microvesicles" or "exosomes," and thus are not EVs, as those terms are used here in.

As used herein, the term "patient" and "subject" are used interchangeably to refer to a human or animal, such as a vertebrate, e.g., a mammal. Examples of mammals include, without limitation, primates, rodents, domestic animals, or game animals. Primates include chimpanzees, monkeys, and macaques, e.g., Rhesus. Rodents include mice, rats, rabbits, and hamsters. Domestic and game animals include cows, horses, pigs, deer, buffalo, feline species, e.g., domestic cat, canine species, e.g., dog, fox, avian species, e.g., chicken, duck, and ostrich, and fish, e.g., trout, bass, and salmon. Patient or subject includes any subset of the foregoing, e.g., all of the above, but excluding one or more groups or species such as humans, primates, or rodents. In certain embodiments of the aspects described herein, the subject is a mammal, e.g., a primate, e.g., a human. A subject can be male or female. Additionally, a subject can be any stage of development, e.g., embryo, fetus, infant, child, pre-adolescent, adolescent, young adult, mature adult, and elderly adult. The female subject can be pregnant or not.

In one embodiment, the subject can be a patient or a subject in a clinical setting. The subject can be suspected of, or at risk for, having or developing a disease or disorder, or may have already been diagnosed as having a disease or disorder. The subject may be a patient undergoing treatment.

As used herein, a "capture agent" refers to any agent having specific binding for EVs generally (e.g., an exosome) or target EVs. Binding may be to a marker, e.g., biomarker, that is present on all EVs, or to a subset of target EVs. Typically the capture agent specifically binds to a biomarker fully or partially present on the external surface of the EVs (referred herein as an extravesicular marker), although in some embodiments, the capture agent specifically binds to a marker that is present on the interior of the EV (referred herein as an intravesicular marker). The capture agent is immobilized on the surface of a plasmonic nanostructure that is contacted to the sample (e.g., the sensing area). Examples of capture agents include, without limitation, nucleic acids, oligonucleotides, peptides, polypeptides, aptamers, antigens, polyclonal antibodies, monoclonal antibodies, single chain antibodies (scFv), antibody portions, F(ab) fragments, F(ab')$_2$ fragments, Fv fragments, small organic molecules, polymers, compounds from a combinatorial chemical library, inorganic molecule, or any combination thereof.

A "nucleic acid," as described herein, can be RNA or DNA, and can be single or double stranded, and can be, for example, a nucleic acid encoding a protein of interest, a polynucleotide, an oligonucleotide, a nucleic acid analogue, for example peptide-nucleic acid (PNA), pseudo-complementary PNA (pc-PNA), locked nucleic acid (LNA) etc. Nucleic acid sequences include, for example, but are not limited to, nucleic acid sequences that act as transcriptional repressors, antisense molecules, ribozymes, small inhibitory nucleic acid sequences, for example, but not limited to, RNAi, shRNAi, siRNA, micro RNAi (mRNAi), antisense oligonucleotides etc.

As used herein, the term DNA is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules including nucleosides or nucleoside analogs containing chemically or biologically modified bases, modified backbones, etc., whether or not found in naturally occurring nucleic acids, and such molecules can be used for certain applications.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Examples of modifications include glycosylation and palmitoylation. Polypeptides can be purified from natural sources, produced using recombinant DNA technology, synthesized through chemical means such as conventional solid phase peptide synthesis, etc. An "antigen" is defined herein as a substance inducing an immune response. The antigenic determinant group is termed an epitope, and the epitope in the context of a carrier molecule (that can optionally be part of the same molecule, for example, botulism neurotoxin A, a single molecule, has three different epitopes. Usually antigens are foreign to the animal in which they produce immune reactions.

As used herein, "antibodies" can include polyclonal and monoclonal antibodies and antigen-binding derivatives, or portions or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. As used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (see, e.g., Klein, Immunology (John Wiley, New York, N.Y, 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford).

The term "reporter group," as used herein, refers to a composition capable of producing or enhancing a detectable optical signal indicative of the presence of the target in a sample. Examples of reporter groups include fluorescent molecules, such as fluorescein isothiocyanate (FITC), tetramethylrhodamine (TRITC), Alexa Fluor® 488, Cy3, Cy5, Cy5.5, and Cy7; small molecules for Raman signals, such as benzenethiol, 4,4'-bipyridine, and R6G; and nanoparticles made of metal, semiconductor, plastic, polymer, and glass. Another example of reporter groups is a QUAD marker (Mucin 1, cell surface associated (MUC1), Epidermal Growth Factor Receptor (EGFR), epithelial cellular adhesion molecule (EpCAM), and human epidermal growth factor receptor 2 (HER2)), The terms "label," as used herein, refer to a composition capable of producing or enhancing a detectable signal indicative of the presence of the target in a sample. "Labeling" is referred herein as a primary antibody conjugated with a biomarker, or a secondary antibody conjugated with a primary antibody. "Labeling" is referred herein as an EV labeling with a capture agent.

As used herein, the term "marker" or "biomarker" refers to a molecule that is associated with an EV, and can bind to a capture agent for detecting the EV. A marker can be any components of an EV that can be recognized by a capture agent. Examples of markers include, without limitation, proteins, or nucleic acids or a component of the lipid bilayer that makes up the membrane of the EV Useful markers include receptors (e.g., extracellular) and channel components. A marker can be either an extravesicular or an intravesicular marker, as defined herein. A marker can be present on all EVs in a sample, or on a subset of EVs in a sample. A marker that is common to all EVs in a sample is referred to herein as a pan-EV marker.

The term "QUAD biomarkers" as used herein refers to MUC1, EpCAM, HER2, and EGFR.

As used herein, when one element is "fixed" to another, the two elements are directly connected via bonds, e.g., ionic, covalent, polar, or hydrogen bonds. When two elements are "bound" to each other, the two elements are directly or indirectly connected, via bonds, or via other elements, such as linker groups, e.g., PEG, or affinity ligands as described herein.

An "affinity ligand" is defined herein as a molecule that is directly attached or fixed to a molecular spacer or to a substrate or nanostructure, and also can be directly attached to a capture agent or a molecular spacer. In some embodiments, an affinity ligand can be a capture agent. Stated another way, an affinity ligand physically links a molecular spacer (or substrate or nanostructure) and a capture agent (or molecular spacer) together. In one embodiment, the affinity ligand is a first member of a specific binding pair. In such an embodiment, the capture agents may be the second member of the specific binding pair. Examples of such specific binding pairs include, without limitation, antigens, antibodies, haptens, oligonucleotides, polynucleotides, avidin, streptavidin, hormones, receptors, lectins, carbohydrates, IgG, protein A, and nucleic acid binding proteins. An affinity ligand can include, but is not limited to, a nucleic acid, oligonucleotide, peptide, polypeptide, antigen, polyclonal antibody, monoclonal antibody, single chain antibody (scFv), an antibody portion, F(ab) fragment, F(ab')2 fragment, Fv fragment, small organic molecule, polymer, compounds from a combinatorial chemical library, inorganic molecule, or any combination thereof.

Examples of specific binding pairs include antigen-antibody, hapten-antibody or antibody-antibody pairs, complementary oligonucleotides or polynucleotides, avidin-biotin, streptavidin-biotin, hormone-receptor, ligand-receptors, lectin-carbohydrate, IgG-protein A, nucleic acid-nucleic acid binding protein, and nucleic acid-anti-nucleic acid antibody.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity that is at least 10 times greater than the affinity for the third non-target entity. A reagent specific for a given target is one that exhibits specific binding for that target under the conditions of the assay being utilized. In certain embodiments, specific binding is indicated by a dissociation constant on the order of $<10^{-8}$ M, $<10^{-9}$ M, $<^{-10}$ M or below.

Polyethylene glycol (PEG) is referred to herein as a possible component of the nano-plasmonic array and is used as a molecular spacer. A variety of forms and combinations of PEG are envisioned for use as such spacers. Polyethylene glycol (PEG) is a polyether compound with many applications from industrial manufacturing to medicine. The structure of PEG is (note the repeated element in parentheses): $H$—$(O$—$CH_2$—$CH_2)_n$—$OH$. PEG is also known as polyethylene oxide (PEO) or polyoxyethylene (POE), depending on its molecular weight. PEG, PEO, or POE refers to an oligomer or polymer of ethylene oxide. The three names are chemically synonymous, but as used herein, PEG refers to oligomers and polymers with a molecular mass below 20,000 g/mol, PEO refers to polymers with a molecular mass above 20,000 g/mol, and POE refers to a polymer of any molecular mass. PEG and PEO are liquids or low-melting solids, depending on their molecular weights. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. Branched PEGs have three to ten PEG chains emanating from a central core group. Star PEGs have 10 to 100 PEG chains emanating from a central core group. Comb PEGs have multiple PEG chains normally grafted onto a polymer backbone.

A "long-chain polyethylene glycol (PEG)" or "long PEG" is defined herein as a PEG polymer having a molecular weight equal to or higher than 750 Da.

A "short-chain PEG" or "short PEG" is defined herein as a PEG polymer having a molecular weight equal to or less than 500 Da.

As used herein, "expression level" refers to the number of mRNA molecules and/or polypeptide molecules encoded by a gene of interest that are present in a cell or sample.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety.

The details of one or more embodiments of the invention are set forth in the accompanying drawings, description, and the claims. Other features, objects, and advantages of the invention will be apparent from the description and drawings, and from the claims.

DESCRIPTION OF DRAWINGS

This patent or application file contains at least one drawing executed in color. Copies of this patent or patent application publication with color drawing(s) will be provided by the Office upon request and payment of the necessary fee.

FIG. 1A is a diagram of the procedural steps of multiplexed single EV analysis. FIG. 1B is an image of periodic nanoholes in the nano-plasmonic array. FIG. 1C is an image showing the enhanced electromagnetic fields on the nanohole surface of the nano-plasmonic array. FIG. 1D are images of fluorescent nanospheres on glass and the nano-plasmonic substrates. FIG. 1E is a histogram of pixel intensities of a glass substrate and the nano-plasmonic substrate. FIG. 1F is a bar graph showing fluorescence intensity of fluorescent nanostructures on glass and the nano-plasmonic substrate. FIG. 1G is an image showing a magnified view of the nano-plasmonic array.

FIG. 2A is a schematic diagram of an optical system for multiplexed single EV analysis. FIG. 2B is a microscope image of the nano-plasmonic array.

FIG. 3A is a series of images of substrates coated different fluorophore-conjugated biotin-binding proteins. FIG. 3B is a bar graph showing intensity profiles of different fluorophore-conjugated biotin-binding proteins. FIG. 3C is a bar graph showing fluorescence intensity of different fluorophore-conjugated biotin-binding proteins. FIG. 3D is a graph showing the absorption/emission spectra of different fluorophore-conjugated biotin-binding proteins. FIG. 3E is a pair of images of EVs captured on glass and substrates of the nano-plasmonic arrays. FIG. 3F is a graph showing intensities of captured EVs on glass and substrates of the nano-plasmonic arrays. FIG. 3G is a bar graph showing the number of EVs on glass and substrates of the nano-plasmonic arrays. FIG. 3H is a pair of images of EVs captured on glass and substrates of the nano-plasmonic arrays with an adhesive layer. FIG. 3I is a graph showing intensities of captured EVs on glass and substrates of the nano-plasmonic arrays with an adhesive layer. FIG. 3J is a bar graph showing the number of EVs on glass and substrates of the nano-plasmonic arrays with an adhesive layer.

FIG. 4A to FIG. 4C illustrate single EV measurements. FIG. 4A is a series of microscope images of captured EVs with different fluorescent antibodies. FIG. 4B is a series of graphs showing intensities of EVs with different fluorescent antibodies in different positions on the substrate. FIG. 4C is a series of bar graphs showing the number/fraction of EVs with different fluorescent antibodies.

FIG. 5A is a series of microscope images of EVs labeled against tumor marker EGFR. FIG. 5B is a series of microscope images of EVs labeled against tumor marker EGFRvIII. FIG. 5C is a representation of gels showing EGFR expression in different EVs. FIG. 5D is a bar graph showing EGFR fractions in different EVs. FIG. 5E is a bar graph showing EGFRvIII fractions in different EVs.

FIG. 6A to FIG. 6G illustrate measurements of tumor markers in EV-spiked plasma samples. FIG. 6A is a flow chart showing a decision tree to classify EV populations. FIG. 6B and FIG. 6C are series of graphs showing EV populations positive for different markers. FIG. 6D to FIG. 6G are bar graphs showing EV detection and marker profiling.

FIG. 7A is a graph showing a size distribution of EVs isolated from Gli36-WT and Gli36-EGFRvIII. FIG. 7B is a series of images of gels showing expression levels of EVs isolated from Gli36-WT and Gli36-EGFRvIII.

FIG. 8A is a series of microscope images of EVs labeled against different markers. FIG. 8B is a series of bar graphs showing the fractions of EVs labeled against different markers under different EV concentrations.

FIG. 9A is a pair of microscope images showing sensitivity and specificity of EVs labeled against EGFR. FIG. 9B is a pair of microscope images showing sensitivity and specificity of EVs labeled against EGFRvIII.

FIG. 10A is a schematic diagram of a step of imprinting nanorods on a resist layer. FIG. 10B is a schematic showing a step of patterning an imprinting mold. FIG. 10C is a schematic diagram of a step of depositing gold nanorods and lifting off of the mask. FIG. 10D is a schematic diagram that shows the use of the nano-plasmonic array to detect EVs that bind to the gold nanorods.

FIG. 11A to FIG. 11D illustrate an example of a method for detecting target EVs. FIG. 11A is a schematic diagram that illustrates an example of a nano-plasmonic array including nanorods for plasmon-enhanced single EV sensing technology (NEXT), as described herein. FIG. 11B is a representation of a microscope image of an EV bound to a nanorod. FIG. 11C is a representation of a microscope image of a nanorod array. FIG. 11D is a representation of a microscope image of EVs bound to different locations on nanorod.

FIG. 11E-a is a schematic of an example of a fabrication procedure for 3D Au nanoparticles (AuNPs) on Au nanopillars (NPOP) structure, as described herein.

FIG. 11E-b is a photograph of wafer-scale (90 cm² area) chip.

FIGS. 11E-c and 11E-d are scanning electron images of nanopillars formed on a PET substrate, and 3D NPOP structures formed on coated nanopillars (scale bar, 200 nm).

FIG. 11E-e is a transmission electron image of 3D NPOP structures. The inset shows the size distribution of AuNPs on the nanopillars.

FIG. 11E-f is a high resolution transmission electron image showing a zoomed-in image of the white dashed box in (e).

FIG. 11E-g shows a finite element method (FEM) simulation of the 3D NPOP structure shown in the large dashed box in 11E-e.

FIG. 12A is a graph showing scattering intensities of nanorods of different sizes.

FIG. 12B is a graph showing scattering intensities changes in dark field imaging.

FIG. 13A is a representation of side view of EV captured on a nanorod. FIG. 13B is a representation of a top view of a nanodisk. FIG. 13C is an image of top view of a nanodisk. FIG. 13D is a graph showing scattering intensities of nanodisks having different diameters. FIG. 13E is a graph showing peak shifts of nanodisks having different diameters. FIG. 13F is a representation of a top view of a nanorod. FIG. 13G is a graph showing scattering intensities of nanorods having different diameters. FIG. 13H is a graph showing peak shifts of nanorods having different diameters.

FIG. 14A to FIG. 14F illustrate three FDTD simulation scenarios showing spectral shifts of dark-field scattering upon EV binding to nanodisks in different locations and distances to the substrate. FIG. 14A is a representation of Scenario 1 of a first EV binding location and its detected peak wavelength, along with a corresponding graph. FIG. 14B is a representation of Scenario 2 of a second EV binding location and its detected peak wavelength, along with a microscope image showing electromagnetic waves. FIG. 14C is a representation of Scenario 3 of a third EV binding location and its detected peak wavelength, along with a microscope image showing electromagnetic waves. FIG. 14D is a representation of dark-field scattering spectra of nanodisks upon EV binding in varying distances (z) to the surface, showing the different level of spectral shifts depending on the distance between the EV and nanodisk. FIG. 14E is a representation of electromagnetic fields in a cross-section of a nanodisk on a glass substrate, showing the concentrated electromagnetic fields on top of the nanodisk surface. FIG. 14F is a presentation of electromagnetic fields on a nanodisk on a glass substrate in a top view, showing the concentrated electromagnetic fields along the sides of the nanodisk.

FIG. 15A is a representative dark-field scattering image of nanodisks before EV binding. FIG. 15B is a representative dark-field scattering image of nanodisks after EV binding. FIG. 15C is a representative graph showing the changes in the dark-field scattering intensity over time for EVs on the nanodisk shown in FIG. 15A and FIG. 15B. FIG. 15D is a representative graph showing the changes in the dark-field scattering intensity over time for controls on the nanodisk shown in FIG. 15A and FIG. 15B.

FIG. 18A to FIG. 18D illustrate an example plasmon enhancements of dark-field and fluorescence signals in different sizes of nanodisks. FIG. 18A is a plasmon intensity of dark-field corresponding to different diameters of nanodisks. FIG. 18B is a plasmon intensity of TRITC corresponding to different diameters of nanodisks. FIG. 18C is a plasmon intensity of Cy5 corresponding to different diameters of nanodisks. FIG. 18D is a plasmon intensity of Cy5.5 corresponding to different diameters of nanodisks.

FIG. 19A is a series of fluorescence images of AF555-(left) or AF647-labeled (right) EVs on glass or NPOP substrate in different concentrations.

FIG. 19B is a pair of graphs for comparison of EV counting numbers in different dilution factors on glass or NPOP substrates (left graph, AF555-labeled EVs; right graph, AF647-labeled EVs).

FIG. 19C is a pair of histogram plots for comparison of EV intensities (1:1600 dilution) in glass and NPOP substrate (left graph, AF555-labeled EVs; right graph, AF647-labeled EVs).

FIG. 19D is a bar graph that shows quantitative analysis of signal enhancement. The NPOP substrate enhanced the signal intensities by 2 fold (AF555) and 9 fold (AF647) compared with the glass substrate.

FIG. 21A is a schematic of an example of a multi-channel detection strategy for single EV analysis with a gold nano-pillar array (NPOP substrate) as described herein. An NPOP substrate was functionalized by SH-PEG-COOH (1.0 kDA) and EVs were captured by EDC/NHS activation. Next, the captured EVs were fluorescently stained by marker-specific antibodies. The EVs were then labeled with different fluorescence-conjugated wheat germ agglutinin (WGA). Finally, the multi-color labeled EVs were imaged and analyzed.

FIG. 21B is a series of representative images for EV capture by functionalization with mercaptoundecanoic acid (MUA) (1.7 nm length), SH-PEG-COOH (0.3 kDA, 2.8 nm length), and SH-PEG-COOH (1.0 kDa, 7 nm length) with or without EDC/NHS activation (scale bars, 50 μm).

FIG. 21C is a bar graph of EV counting showed SH-PEG-COOH showed the least non-specific EV binding (ns, not significant; ****P<0.0001 compared with the mock treatment, as assessed by two-way ANOVA with Bonferroni's multiple comparisons test). Error bars are shown as mean±SD from the ten different images.

FIG. 24A is a series of representative images of CD63 (vs. IgG) detection on EVs.

FIG. 24B is a pair of graphs showing EV count and marker positive EV count results for CF63 and IgG.

Like reference symbols in the various drawings indicate like elements.

DETAILED DESCRIPTION

Figures 1A, 1B, 1C, 1D, 1E, 1F, 1G:
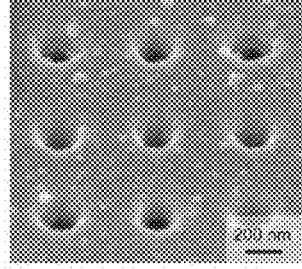
FIG. 1A to FIG. 1G illustrate an example of a nano-plasmonic array for multiplexed single EV analysis.

The present disclosure relates to systems, methods, and devices for detecting target extracellular vesicles (EVs). EVs can be, but are not limited to, ectosomes, microvesicles, microparticles, exosomes, oncosomes, apoptotic bodies, liposomes, vacuoles, lysosomes, transport vesicles, secretory vesicles, gas vesicles, matrix vesicles, or multivesicular bodies. EVs carry multiple surface biomarkers, which can be used as indicators to monitor or diagnose certain diseases, e.g., cancers, cardiovascular, neurodegenerative, and infectious diseases among others. In particular, the new systems and methods can be used for detecting and diagnosing Alzheimer's and other neurodegenerative diseases as well as detecting viruses, bacteria, and/or parasites, e.g., by analyzing immune cells that contain materials from the infective agents.

However, their unique sizes (50-1000 nm) impose technical challenges in conventional analytical methods, which often lead to variable findings. For example, EVs have a dimension of up to about 10 microns, but are typically about 1000 nm or less, about 900 nm or less, about 800 nm or less, about 700 nm or less, about 600 nm or less, about 500 nm or less, about 450 nm or less, about 400 nm or less, about 350 nm or less about 300 nm or less, about 250 nm or less, about 240 nm or less, about 230 nm or less, about 220 nm or less, about 210 nm or less, about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less.

In addition, EVs often provide weak detection signals, especially when the EV sample does not include a sufficient number of EVs or when there is a low abundance of protein and/or intravesicular markers, which can make it challenging to perform sensitive, robust, and standardized assays that can determine the composition and molecular profiles of EVs in clinical samples.

The present disclosure provides a solution to these problems and enables targeting single EVs by amplifying their individual optical signals to achieve an accurate and precise multiplexed analysis of the target EV. Analyzing single EVs can reveal unique molecular profiles of cell-specific EVs, which will further promote clinical use of EVs, e.g., to construct a comprehensive EV "atlas" per different biological parameters (e.g., cellular origin, cell state).

The nano-plasmonic systems of the present disclosure enable multiplexed single EV analyses of target membrane and intravesicular markers with improved sensitivities. Specifically, the optical signal, e.g., fluorescence, is amplified using plasmonic metallic nanostructures to provide sensitive, multi-channel EV biomarker profiling. The enhancement can be achieved, for example, by using a substrate with a periodic array of nanostructures, such as nanoholes, nanorods, nanodisks, nanowells, nanosquares, nanopillars, nanogrooves, or any suitable periodic or non-periodic metallic nanostructures. A copper or aluminum film or substrate can be used for UV illumination, and silver and gold can be used for visible wavelength illumination. In general, the substrate, if used under a metal film, is a non-metal, nonconducting substrate such as glass or plastic, but metal, metal oxides, and semiconductors can also be used as substrates.

For example, a periodic array of Au nanoholes support surface plasmon resonances extended in a long range (about 100 nm) which is suitable for EVs. Furthermore, the resonance wavelength can be readily tuned by adjusting the nanohole periodicity and size. The same can be done with nanostructures in the form of nanorods or nanodisks. In one embodiment, the nano-plasmonic extracellular vesicle analysis with enhanced fluorescence detection (nPLEX-FL) described herein, along with similar methods using other optical signals, provide a simple, robust signal amplification strategy that improves the detection sensitivity and achieves multiplexed EV analysis.

Preparation of Nano-Plasmonic Arrays

The nano-plasmonic arrays used herein include a substrate, a plurality of nanostructures on or in the substrate, and a plurality of affinity ligands fixed on or adjacent to the nanostructures. Different surface chemistries (conjugates to affinity ligands) can be used for the metals used to make the nanostructures and the substrates (e.g., glass) to selectively fix the affinity ligands to the nanostructures, e.g., on the surface of nanorods or nanodisks, within nanogrooves, and on walls within the nanoholes or on the substrate or metal film adjacent to the nanoholes. The plurality of nanostructures are arranged to form a periodic array of nanostructures on the substrate, and the periodic array of nanostructures is arranged and dimensioned to amplify one or more specific wavelengths of electromagnetic radiation.

In some embodiments, the plurality of affinity ligands is fixed on or adjacent to the nanostructures, and the plurality of affinity ligands specifically bind to EVs or target EVs via a capture agent. Different types of affinity ligands can be used in the nano-plasmonic arrays based on a corresponding EV preparation. For example, among high affinity binding pairs, the substrate of the nano-plasmonic arrays can include a biotin-binding protein (e.g., avidin) as the affinity ligands attached on the substrate, then the EVs or target EVs are required to comprise a corresponding biotin as the capture agent to be captured by the nano-plasmonic arrays. In some embodiments, the substrate comprises semiconductors, nonconductors, plastics, or any suitable transparent substrates. Methods for attaching a corresponding capture agent to EVs are described below.

We developed an advanced nano-plasmonic EV sensing platform for single EV analyses using a new nano-plasmonic sensing platform for single EV detection. Termed NEXT (nanostructure-based extracellular vesicle technology), the system includes arrays of metal, e.g., gold, silver, copper, or aluminum, nanostructures, e.g., nanoholes, nanorods, nanodisks, or nanopillars, e.g., in sub-200 nm dimensions, that can be occupied by single EVs. For example, gold nanorods have a high sensitivity down to single molecule detection and precise tunability of resonant wavelengths by adjusting nanorod dimensions. The arrays of nanostructures can be made using standard nanoimprint lithography techniques with good reproducibility through advanced imprinting and deposition processes.

The capture of individual EVs on each nanostructure, e.g., nanorod, induces a spectral shift; those shifts from nanorod arrays will be simultaneously detected by dark-field imaging. Extensive validation studies are performed to benchmark 1) single EV detection sensitivity; 2) specificity for capture a target EV subpopulation; and 3) robustness and reproducibility.

Figures 10A, 10B, 10C, 10D:
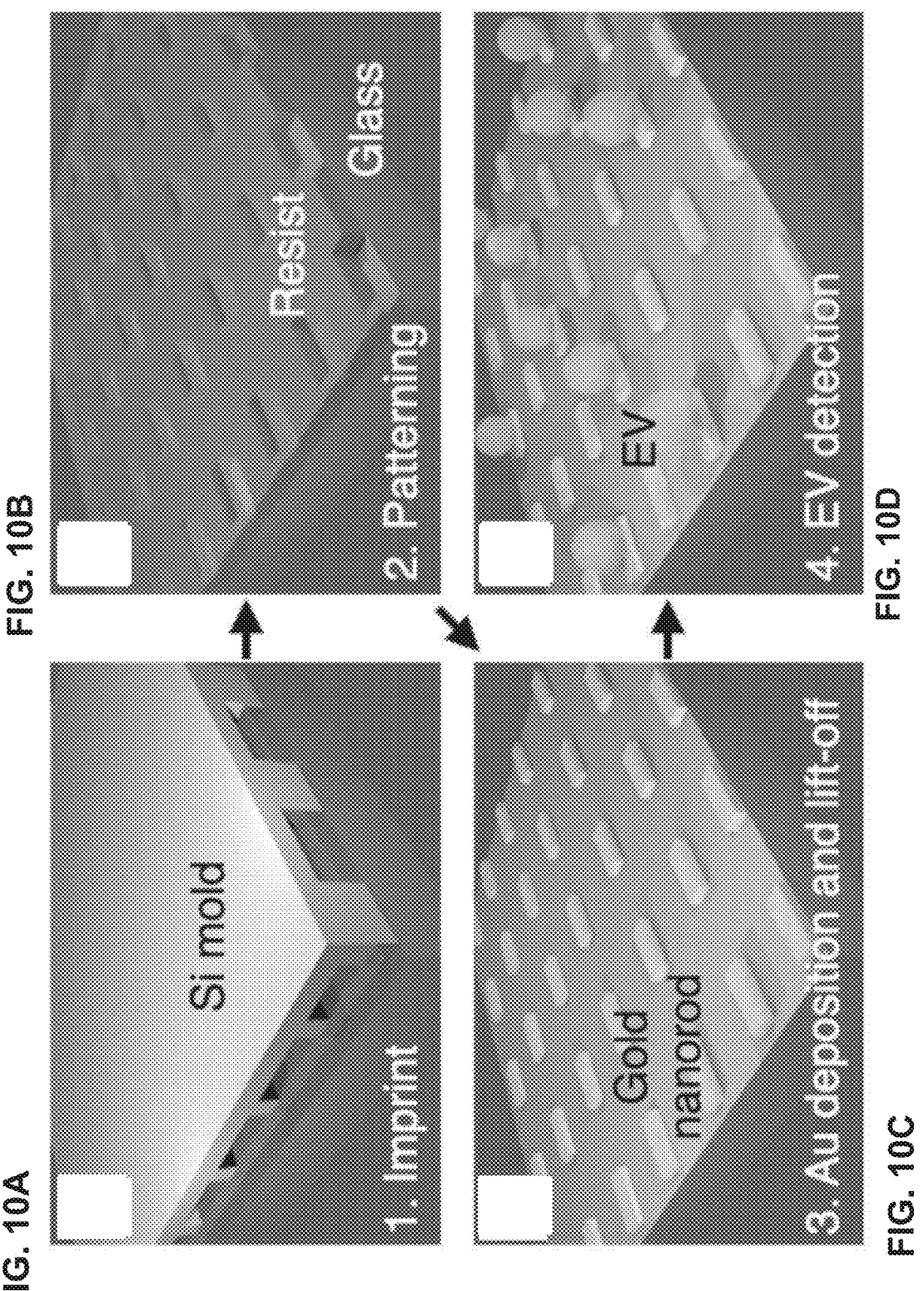
FIG. 10A to FIG. 10D is a series of schematic diagrams that illustrate an example of a method for fabricating a nano-plasmonic array including gold nanorods.

Dense arrays (e.g., $10^5$ array per cm$^2$) of metal, e.g., gold, nanostructures, e.g., nanorods, can be made using a new nanoimprint lithography method that can pattern gold nanorod arrays in a wafer-scale through simple imprinting and gold deposition processes (FIGS. 10A-10D). The technique utilizes a reusable silicon mold with nano-patterns that are transferred to a target substrate coated with a thin resist layer (FIGS. 10A-10B). After imprinting, gold is deposited onto the patterned area; subsequent removal of the resist will leave nanorod arrays on a glass substrate (FIG. 10C). We previously made various metallic nanostructures in high densities using a known fabrication method (ACS Nano 2011, 5, 7555-7564, 2011; Anal. Chem., 84, 6031-6039, 2012). These methods can be used to produce 10 chips per each fabrication cycle in 4 hours or 100 chips in a week (10 cycles×10 chips per cycle) using a typical nanofabrication facility, which is a sufficient chip production rate for subsequent biological experiments. This mass production process is simple, reproducible, and scalable. E-beam lithography can also be used to pattern nanostructure with high precision.

Periodic nanoholes are made by patterning a thin (50 to 200 nm thick) gold film on a substrate. Nanoholes can be directly patterned by focused ion-beam milling or through lithography and metal etching. Deep ultraviolet (DUV) lithography is used to make 200 nm periodic circular patterns on a resist spun-coated on the gold film. Furthermore, the underlying gold film is etched by reactive ion etching or ion milling using the resist as an etch mask. Resist removal reveals gold nanohole patterns made in the gold film.

Array chips are designed through comprehensive three-dimensional computational calculations, and we found in one example that the nanorod dimension of 80 nm (length)× 30 nm (width)×20 nm (height) achieved maximum sensitivity for 100-nm EV (mean diameter) detection, and array sensor dimensions and sensitivities are experimentally tested. The sub-100 nm dimension of gold nanorods also allows single EV capture on each nanorod. Gold nanorod arrays with 3 μm separation between nanorod allow even distribution of EVs on the nanorod arrays; signals from individual EVs are clearly resolved using a 10× or higher objective. The total number of nanorods in a chip is readily scalable with a nanoimprint mold size. For example, one can use a microarray spotter (MicroSys, Digilab Inc.) to functionalize the chip selectively with affinity ligands. With the spotter, 0.1 μL solutions are transferred from a 96-well plate and spotted on designed areas with good reproducibility (<5% variation). Temperature and humidity are controlled inside the spotter chamber for consistent sample spotting and incubation conditions.

A metal, e.g., gold, nanostructure, e.g., nanorod, exhibits a unique dark-field light scattering peak at a resonant wavelength. EV binding to the nanorod surface increases a local refractive index, red-shifting the peak wavelength. The spectral shift (i.e. EV binding) can also be detected by measuring a light intensity change at a fixed wavelength, and there is an excellent correlation between spectral and intensity measurements. The intensity measurement method can be used for high throughput parallel signal reading from entire arrays in a field-of-view. This approach is much faster than sequential spectral measurements used in past systems and methods. The dark-field imaging is also compatible with epifluorescence measurements for molecular EV profiling in the same setup.

EVs, e.g., tumor-derived EVs, can be captured on nanorods and measured by the number of nanorods exhibiting intensity changes induced by EV binding to the nanorod surface. Computational calculation using a finite difference time-domain (FDTD) solution shows that single 100-nm EV binding induces more than a 10 nm shift, a sufficiently large shift readily detected by dark-field intensity measurements. The signal also correlates with the size of captured EVs, facilitating EV size measurements. Once can use size standard nanospheres for calibration and compare the results with those obtained by a nanoparticle tracking analysis (NTA) system. Combined with molecular profiling, the size information can be used to identify EV subtypes (e.g. exosomes vs microvesicles).

By employing dark-field imaging, readout signals from the entire arrays can be measured simultaneously. The intensity measurements provide much higher throughput in readouts of vast arrays than spectral measurements. To avoid signal drift or fluctuation due to changes in light source temperature, one can implement temperature controllers to stabilize the light source temperature and/or increase the number of signal averages to reduce background noises.

FIG. 11A to FIG. 11D illustrate an example of a nano-plasmonic array comprising nanorods for plasmon-enhanced single EV sensing technology (NEXT). FIG. 11A is a schematic drawing of NEXT chip sensor consisting of gold nanorod arrays made in grid. The small surface area of nanorods allows for single EV binding on each nanorod. FIG. 11B is a scanning electron micrograph (SEM) of a nanosphere captured on a gold nanorod (scale bar: 50 nm). FIG. 11C, is a SEM of a nanorod array made by electron-beam lithography, but can also be made with nanoimprint lithography (scale bar: 500 nm). FIG. 11D is a SEM showing binding of single nanospheres, mimicking EVs, on nanorods (scale bar: 200 nm). Captured EVs are labeled by immunofluorescence probes for high throughput multichannel analyses using plasmon enhanced fluorescence detection. The captured EVs are evenly distributed by a distance between nanorods; this will improve the accuracy of analysis.

A fabrication procedure for making nanopillars is shown in FIG. 11Ea-g, which shows new 3D plasmonic nanostructures composed of spherical Au nanoparticles (AuNPs) on 3D Au nanopillars (NPOP) with a 1 nm-thick uniform spacer layer between the AuNPs and the nanopillars. The method is based on enhanced surface diffusion of adsorbed Au atoms (i.e., adatoms) on a low-energy surface; the Au adatoms diffuse into defective sites of the underlying film and form clustered atoms (i.e., AuNPs). This process enables the direct and selective formation of spherical Au nanoparticles through a simple Au deposition process without high-temperature annealing. The AuNPs density can be highly increased by introducing more nucleation sites on the 3D rough Au nanopillar surface.

The 3D NPOP structures provide high-density hotspots and large effective volumes of molecular binding sites for highly sensitive surface-enhanced Raman spectroscopy (SERS) and plasmon-enhanced fluorescence (PEF). We demonstrate highly improved detection sensitivities for both SERS and PEF sensing applications. The fabrication method developed here is cheap, simple, reproducible, and applicable to scaled-up chip production.

FIG. 11E-a shows a schematic of the fabrication procedure for the 3D NPOP substrates. First, a polyethylene terephthalate (PET) substrate was etched with Ar plasma to form polymer nanopillars. A 100 nm-thick Au film was deposited onto the nanopillars by either conventional sputtering or thermal evaporation to form high-density Au-coated nanopillars. As a space layer, a self-assembled monolayer (SAM) of 1H,1H,2H,2H-perfluorodecanethiol (PFDT) was vapor-deposited onto the Au nanopillars. Finally, another layer of Au was deposited onto the PFDT-coated Au nanopillars (see, e.g., Park et al., Advanced Functional Materials, 2019, 29(43):1904257, and US Patent Application Publication No. US 2019/0331605, which are incorporated herein by reference in their entireties, including all figures and reference citations).

FIG. 11E-b shows a photograph of wafer-scale (90 cm$^2$ area) chip fabrication. FIGS. 11E-c and 11E-d are scanning electron images of nanopillars formed on a PET substrate, and 3D NPOP structures formed by deposition of 20 nm of Au onto the PFDT-coated nanopillars (scale bar, 200 nm).

FIG. 11E-e shows a transmission electron image of 3D NPOP structures. The inset shows the size distribution of AuNPs on the nanopillars.

FIG. 11E-f is a high resolution transmission electron image showing a zoomed-in image of the white dashed box in (e). The thickness of the PFDT layer between the AuNP and nanopillar is ~1 nm.

FIG. 11E-g shows a finite element method (FEM) simulation of the 3D NPOP structure shown in a dashed box in 11E-e.

Isolation and Preparation of EVs

Biological samples are obtained, e.g., from a human or other subject, and cells can be cultured in culture media, such as Dulbecco's modified Eagle's medium (DMEM, Cellgro). Media can be supplemented with serum, e.g., 10% Fetal Bovine Serum, antibiotics, e.g., penicillin and/or streptomycin, and kept under 5% CO2 (see, e.g., Min et al., Plasmon-Enhanced Biosensing for Multiplexed Profiling of Extracellular Vesicles, Advanced Biosystems, 2020, 4, 200003. DOI: 10.1002/adbi.202000003, which is incorporated herein by reference in its entirety, including all figures and reference citations).

EVs can be isolated using both standard ultracentrifugation (UC) and size-exclusion chromatography (SEC) methods. Furthermore, EVs are isolated from the medium for the next process. For UC, the filtrates are concentrated, e.g., by 100,000×g for 1 hour. After the supernatant is removed, the EV pellet is washed, e.g., with PBS and centrifuged again, e.g., at 100,000×g for 1 hour. The EV pellet is resuspended in buffer or serum, e.g., in PBS. For SEC, the filtrates are loaded onto filters, e.g., MWCO=10 kDa, and centrifuged, e.g., at 3500×g for 30 minutes at 4° C. After concentration, the volume is adjusted, e.g., to 1 mL with PBS.

EVs can be selected using different biomarkers and respective affinity binding pairs and their manufactures directions.

Ev Labeling and Analysis Protocols

The EV analysis is performed based on the nPLEX-FL protocol described herein, which includes using multiple fluorescent labels, Raman signals, and dark-field scattering signals to detect target EVs for EV analysis. For fluorescence detection, EVs are labeled by fluorescence probes conjugated with affinity ligands. For Raman detection, molecules on the surface membrane or inside of EVs can be directly detected or EVs are labeled by Raman probes conjugated with affinity ligands. For dark-field scattering detection, scattering signals from EVs can be directly detected without any labeling. The nanostructures of the nano-plasmonic arrays are labeled with affinity ligands that specifically bind to EVs or are bound to capture agents that specifically bind to EVs, and then the substrate is exposed to a biological sample for a sufficient time to ensure that the substrate is bound to a sufficient number of EVs.

In one embodiment, biotinylated EVs are captured on neutravidin-coated nanostructures, followed by EV fixation and permeabilization in a fix/perm solution. Surface passivation can be achieved by placing the surface (with or without EVs) in a blocking solution (Superblock PBS, Thermo Fisher) for 20 minutes. This step is important to minimize undesired nonspecific binding. The captured EVs are stained via two-step indirect labeling: first with primary antibodies then with compatible secondary antibodies. Thorough washing is done between steps.

The EVs are labeled with capture agents, such as streptavidin. Finally, the labeled EVs are attached to the nanostructures via the capture agents with a mounting solution and covered with a glass coverslip. Antibodies that can be used in the present disclosure are listed in Table 1 below. Primary antibodies are used to specifically bind to a specific biomarker on the surface of the EVs, and secondary antibodies are used to specifically bind to the primary antibodies. Furthermore, the secondary antibodies are conjugated with a reporter group, e.g., a fluorescent probe, to be used in image processing, or a capture agent such as streptavidin. The assay buffer can be, for example, a BD perm/wash buffer solution (BD Biosciences).

TABLE 1

Antibodies and Dilution Factors

| Antibody | Vendor | Cat No. | Dilution factor |
|---|---|---|---|
| Primary Antibodies | | | |
| CD9 (mouse) | BioLegend | 312102 | 1:200 |
| CD63 (mouse) | Ancell | 215-820 | 1:200 |
| CD81 (mouse) | Santa Cruz | SC-166029 | 1:100 |
| EGFR (rabbit) | CST | 4267S | 1:50 |
| EGFRvIII (rabbit) | CST | 64952S | 1:2000 |
| GAPDH (rabbit) | CST | 2118S | 1:100 |
| CD9 (mouse) for WB | Millipore Sigma | CBL162 | 1:500 |
| CD63 (mouse) for WB | BD Biosciences | 556019 | 1:500 |
| CD81 (mouse) for WB | BD Biosciences | 555675 | 1:500 |
| EGFR (rabbit) for WB | CST | 54359S | 1:1000 |
| GAPDH (rabbit) for WB | CST | 2118S | 1:2000 |
| Secondary Antibodies | | | |
| Alexa 488 Goat anti-mouse IgG Antibody | CST | 4408S | 1:1000 |
| Alexa 555 Goat anti- | CST | 4409S | 1:1000 |

TABLE 1-continued

| Antibody | Vendor | Cat No. | Dilution factor |
|---|---|---|---|
| Antibodies and Dilution Factors | | | |
| mouse IgG Antibody | | | |
| Alexa 647 Goat anti-rabbit IgG Antibody | CST | 4414S | 1:1000 |
| HRP Goat anti-rabbit IgG Antibody for WB | CST | 7074S | 1:3000 |
| HRP Goat anti-mouse IgG Antibody for WB | CST | 7076S | 1:3000 |
| Streptavidin | | | |
| Streptavidin Alexa 488 | BioLegend | 405235 | 1:400 |
| Streptavidin cy3 | BioLegend | 405215 | 1:400 |
| Streptavidin cy5 | BioLegend | 405209 | 1:400 |
| Streptavidin cy5.5 | Rockland | S000-13 | 1:400 |

Any other antibodies can also be used in the present disclosure based on the specific use. Considering different biomarkers of EVs, a corresponding antibody can be selected. EV biomarkers associated with different diseases and purposes are listed in Table 2 below.

TABLE 2

| EV Biomarkers | |
|---|---|
| Disease Model | EV Biomarker |
| General cancer | EpCAM, EGFR, MUC1, HER2 |
| Ovarian cancer | EpCAM, CD24 |
| Glioblastoma | EGFR, EGFRvIII, IDH1 R132H, PDPN |
| Pancreatic cancer | EpCAM, EGFR, MUC1, WNT2 |
| Alzheimer's diseases | amyloid beta, tau |
| Cellular Origin | EV Biomarker |
| Neurons | LICAM, NCAM |
| Astrocytes | GLAST, Glutamine synthetase, GFAP, EAAT2 |
| Microglia | CD11b, TMEM119, MHCII |

In some embodiments of the present disclosure, the image processing of the captured EVs is performed using image analysis software, such as ImageJ® and CellProfiler®. The streptavidin imaging channel is used to identify location of captured EVs and define regions of interests as masks. For each molecular target (e.g., proteins on the membrane or inside of EVs), the corresponding fluorescent images from target molecules are aligned using ImageJ® plugins (Align slices in the stack). At each mask position, average pixel intensities are obtained. The signal is corrected by subtracting background signal surrounding the mask.

In some embodiments, QUAD biomarkers can be used for multiplexed analysis of surface markers on EVs, e.g., for methods for diagnosing cancer, e.g., cancer of epithelial origin, by detecting the presence of tumor cells in a sample, based (at least in some embodiments) on the quantification of levels of four biomarkers, e.g., MUC1, EGFR, EpCAM, and HER2. Of individual biomarkers investigated, MUC-1, HER2, EGFR, and EpCAM provide the highest diagnostic accuracy, but combining these four markers established a very high level of accuracy that is superior to conventional clinical analysis. See, e.g., U.S. Pat. No. 10,712,343, which is incorporated herein by reference in its entirety. However, additional or alternative biomarkers may also be used in the multiplexed analysis.

In some embodiments, the tumor is a pancreas, lung, breast, prostate, kidney, stomach, esophagus, bladder, endometrial, cervix, biliary, thyroid, ovary, brain, head and neck, oral, melanoma, liver, or colon tumor.

Described herein are methods for diagnosing or detecting the presence of a cancer in a subject. The methods include obtaining a sample from a subject, isolating EVs from the sample, and evaluating the presence and/or level of MUC-1, HER2, EGFR, and EpCAM in the EVs, and comparing the presence and/or level with one or more references, e.g., a control reference that represents a normal level of MUC-1, HER2, EGFR, and EpCAM, e.g., a level in an unaffected subject, and/or a disease reference that represents a level of the QUAD biomarkers in a subject having cancer. In some embodiments, the methods include determining a value, e.g., a normalized expression value, for each of the biomarkers (MUC-1, HER2, EGFR, and EpCAM), and calculating a test score from the sum of each of the levels. This score can then be compared to a reference score, wherein the presence of a test score above (e.g., equal to or above, or simply above) the reference score indicates the presence of cancer in the subject. See, e.g., U.S. Pat. No. 10,712,343.

The methods also can be used to monitor a patient, e.g., to determine whether a treatment has been effective, or whether a subject is experiencing a recurrence, or whether treatment resistance is emerging. In these embodiments, the methods include detecting the presence and/or level of biomarkers in EVs obtained from a subject over time, e.g., in a first or baseline sample, and then in one or more subsequent EV samples, e.g., over a period of one or more weeks or months. For some biomarkers, a decrease over time in the presence or levels of the biomarkers, e.g., a decrease in the biomarker value, in the EVs indicates an improvement in the disease, e.g., that a treatment administered in the intervening time is effective to cause a decrease in a number of cancerous cells or tumor burden. While the QUAD biomarkers may be used in this analysis, additional or alternative biomarkers may also be used in the multiplexed analysis of surface markers on EVs.

No change in the presence or levels of the biomarkers, e.g., no change in the QUAD biomarker value of the EVs, indicates no change in disease, e.g., that any intervening treatment was not effective to cause a decrease in a number of cancerous cells or tumor burden (though in particularly aggressive disease the treatment may have been effective to halt progression, which may be a treatment goal).

A decrease over time in the presence or levels of the biomarkers, e.g., in the QUAD biomarker value, for the EVs, followed by a period of no change or an increase in the presence or levels of the biomarkers, e.g., in the quad biomarker value, indicates that any intervening treatment has lost effectiveness, and may indicate the presence of emerging resistance to the treatment.

An increase over time in the presence or levels of the biomarkers, e.g., an increase in the QUAD biomarker value, indicates that the disease is progressing, e.g., there has been an increase in a number of cancerous cells and/or tumor burden. Such an increase may also be indicative of a poor prognosis, e.g., an increased likelihood of mortality.

In some embodiments, the methods include the use of antibodies or antigen fragments thereof, or oligonucleotides, that specifically bind (i.e., do not bind substantially to other molecules) to the biomarkers. The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, nonhuman, (e.g., murine), or single chain antibody. In some embodiments the antibody has effector function and can fix complement. In some embodiments, the antibody has reduced or no ability to bind to an Fe receptor. For example, the antibody can be an isotype or subtype, fragment or other mutant, which does not support binding to an Fe receptor, e.g., it has a mutagenized or deleted Fe receptor binding region.

Methods for making antibodies and fragments thereof are known in the art. See, e.g., U.S. Pat. No. 10,712,343 and the citations therein.

Methods of Use

The new methods and nano-plasmonic arrays can be used to analyze single EVs in multiple scenarios. For example, tumor-derived EVs contain protein and RNA markers reflective of primary tumor cells, and the new nano-plasmonic array sensors can rapidly and sensitively detect tumor EVs directly from clinical samples. Thus, EV analyses offer compelling clinical potential for diagnosing cancers and monitoring longitudinal tumor response to therapy.

Highly sensitive single EV detection platforms as described herein will significantly improve our understanding of EV biology, allow for rapid and reliable screening of EVs from clinical specimens, and enable analysis of subtle phenotypic changes during treatment. Importantly, this would help the field understand how well EVs align with their primary tumor counterparts and whether EV counts and/or molecular profiles offer additional insight into cancer progress or treatment response. In the long-term, achieving successful high-throughput EV profiling in blood will pave the way for other clinically grounded screening studies (e.g. EVs in other body fluids and cancer types). This will render a more accessible tool to significantly accelerate the clinical adoption of EV analyses as routine screening tests for cancer care in clinical settings. The single EV detection platforms as described herein enable to identify individual EVs derived from tumors or specific organs and detect specific target molecules on the membrane or inside of EVs from the target subpopulation, otherwise diluted or undetected by EVs from non-target origins. The molecular profiling of EVs from target-specific tumors or organs can indicate the molecular status of originating cells.

Figure 20:
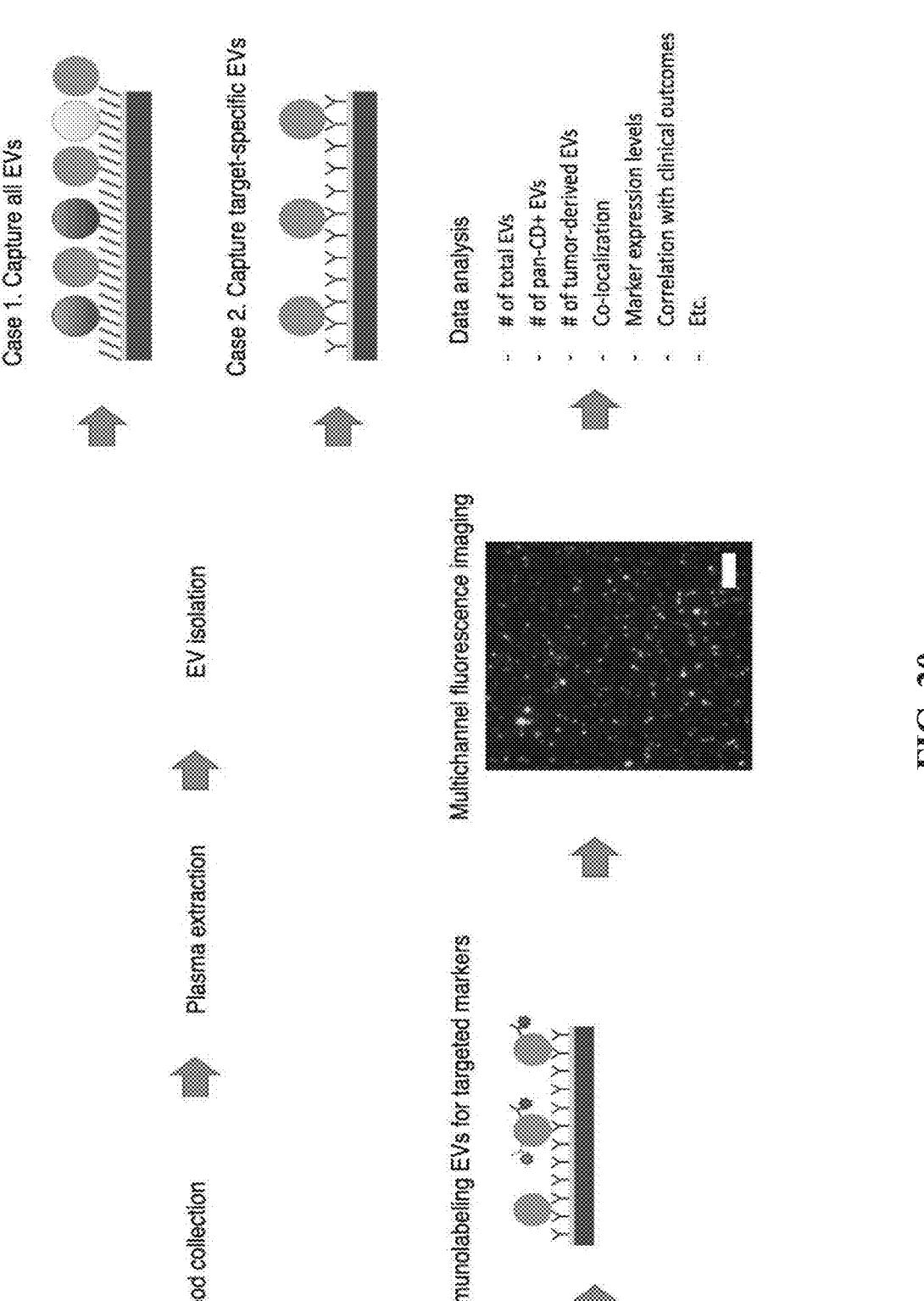
FIG. 20 is a schematic showing an example of a workflow of a plasmon-enhanced EV assay as described herein.

FIG. 20 illustrates depicts the overall workflow of the plasmon-enhanced EV assay. First, EVs are isolated from human specimens (e.g., blood or other biofluids) or cell culture supernatant.

The isolated EVs are captured on a plasmonic substrate with nanostructures, e.g., gold nanostructures (e.g., nanopillars, nanodisks, nanorods, nanoholes, nanoslits, nanoparticles, random structures), either by covalent bonding/binding or by affinity ligands. For the former, the surface of plasmonic substrates (made of gold, silver, copper, aluminum, platinum. or their combination) is functionalized with a linker (e.g., PEG or carbon chains with functional groups) or biomolecule adhesion layer to capture all EVs on the surface via non-specific interactions. For the latter, marker-positive, target EV subpopulations are captured on the surface via affinity ligands/capture agents (e.g., antibodies, aptamers, peptides, nucleic acids). The first case is the capture of all EVs. The second case is the capture of target EVs.

The captured EVs are then immune-labeled with fluorophores for marker analysis. The markers include, but are not limited to, surface proteins, intravesicular proteins, lipids, and nucleic acids. Ligands used to capture EVs on the substrate can be also used for marker labeling. For example, QUAD markers (MUC1, HER2, EGFR, and EpCAM) can be used. In the first case, only target EVs among all EVs are labeled using target EV-specific capture agents bound to reporter groups. The capture agents must specifically bind to markers found only on target EVs, and not on all EVs. In the second case, all EVs that are bound to the nanostructures and/or the substrate are target EVs, and so all can be labeled with reporter groups, and thus the reporter groups can be bound to capture agents that bind to any EVs (since only target EVs are present on the substrate). Of course, target EV-specific reporter groups can be used in both cases. The end goal is to label with reporter groups only the target EVs.

The labeled target EVs are imaged, e.g., by a fluorescence microscope. As shown in FIG. 20, images from multiple fluorescence channels can be obtained for multiplexed analysis of EV markers at the single EV level. The images are then analyzed to detect the total number of EVs and their concentrations, marker-positive EVs (EVs positive for CD63/CD81/CD9 (Pan-CD) or tumor-derived EVs), co-localization between channels, marker expression levels, correlation with clinical outcomes, etc.

FIG. 21A is a schematic that depicts EV capture on gold nanopillar arrays. The gold nanopillars can be decorated with gold nanoparticles to increase the plasmon enhancements. The gold nanopillar diameter can be 20-500 nm and the height can be 20-5000 nm. The diameter of decorating nanoparticles can be 10-100 nm. The schematic shows the case of non-specific EV capture via PEG-COOH after the activation of carboxylated groups by EDC/NHS. Alternatively, antibodies can be immobilized on the nanopillar surface to capture marker-specific EVs. The captured EVs are labeled by fluorophore-conjugated antibodies.

Numerical Simulations

Furthermore, numerical simulation can be applied to calculate resonance peak wavelengths, determine the choice of labels for maximum optical signal amplification, and optimize nanostructure dimensions and materials. Electrodynamic computation can be performed using the finite-difference time-domain (FDTD) method. For electric field distribution, x-polarized plane wave is illuminated along z direction. 2-nm mesh size is used for the volume of $0.3 \times 0.3 \times 0.2 \ \mu m^3$ locating at the center of nanohole. Periodic boundary conditions are imposed along the x and y direction and perfect match layers are used for the z direction. A z-polarized dipole source is used for radiative decay rate simulation. The position of the dipole is set to x=100 nm, y=0 nm and z=6 nm to locate it at the edge of nanohole and 6 nm above the Au surface of the nano-plasmonic array.

Furthermore, statistical analyses and data plotting can be performed in GraphPad Prism 7. Group differences are tested using the unpaired t-test. All tests are two-sided, and a P-value of <0.05 is considered statistically significant.

General Methodology

FIGS. 1A to 1G illustrate an example of a nano-plasmonic array for multiplexed single EV analysis. FIG. 1A illustrates the procedural steps of the multiplexed single EV analysis starting from capturing EVs, e.g., target EVs, labeling the captured target EVs, taking images of the labelled target EVs, and analyzing the images of target EVs. EVs are captured on the nanohole surface and immune-stained by fluorescent detection probes, and then labeled target EVs are imaged in different fluorescence channels, and their intensities are analyzed. For example, EVs are captured on the Au nanohole surface via affinity ligands (e.g., capturing biotinylated EVs on avidin-coated Au nanohole surface). The target EVs, which can be some or all of the captured EVs are then immune-stained by fluorescently labeled antibodies in different color channels (typically 3 to 4 colors). Depending on the absorption and emission spectra of fluorophores, the fluorescence signals are amplified by surface plasmon resonances (SPR) excited by the underlying Au nanohole structures.

FIG. 1B illustrates a scanning electron micrograph of periodic nanoholes in the nano-plasmonic array. The diameter of a nanohole is about 200 nm and the periodicity is 500 nm. The scale bar in FIG. 1B is 1 µm. The nanostructure in FIG. 1B is optimized as a SPR substrate, and the substrate is a 100-nm thick Au film.

FIG. 1C illustrates a finite-difference time-domain simulation showing the enhanced electromagnetic fields confined on the nanohole surface of the nano-plasmonic array. The strong fields are responsible for plasmon-enhanced fluorescence signals. The periodic nanohole granting on the chip surface concentrates electromagnetic fields with the maximum field intensity up to 300-fold. The resonance fields extend to 110 nm in the z-direction, which mostly covers small EVs (e.g., exosomes with an average diameter of 100 nm). In addition to the localized near field, the fluorescence radiation can be further enhanced by the interaction of the Au nanostructure with proximal fluorophores in the resonance range.

FIG. 1D illustrates images of fluorescent nanospheres (using Cy5, 200 nm) on glass and the present nano-plasmonic substrates. The scale bar in FIG. 1D is 10 µm. The plasmon-enhanced fluorescence by Au nanohole structures of the nPLEX chip using fluorescent nanospheres (Cy5, 200 nm) is tested in comparison with a glass substrate. Furthermore, FIG. 1E illustrates example histograms of pixel intensities of a glass substrate and the present nano-plasmonic substrate. It shows that the fluorescence intensities of individual nanospheres are significantly higher on the nPLEX-FL substrate (two-tailed t-test, p<0.0001). FIG. 1F illustrates a mean fluorescence intensity of fluorescent nanospheres on glass and the nano-plasmonic substrates. The mean fluorescence intensity is increased by a factor of 18, and the signal-to-noise ratio (given by signal divided by 3-times standard deviation of blank) is increased by a factor of 20, from 17.7 (glass) to 358 (nPLEX-FL). There is no significant difference in the coefficient of variation, given by the ratio of the standard deviation to the mean, for fluorescence intensities between the glass (36.2%) and nPLEX-FL substrates (33.6%), indicating the signal amplification does not increase the intensity variation.

FIG. 1G illustrates a finite-difference time-domain simulation that shows the enhanced electromagnetic fields around a nanohole. The scanning electron microscopy shows EVs captured by functionalized Au nanohole chip. The dotted circles represent the enhanced electromagnetic field distribution around the nanoholes.

Dual-Mode Imaging Device

Figures 2A, 2B:
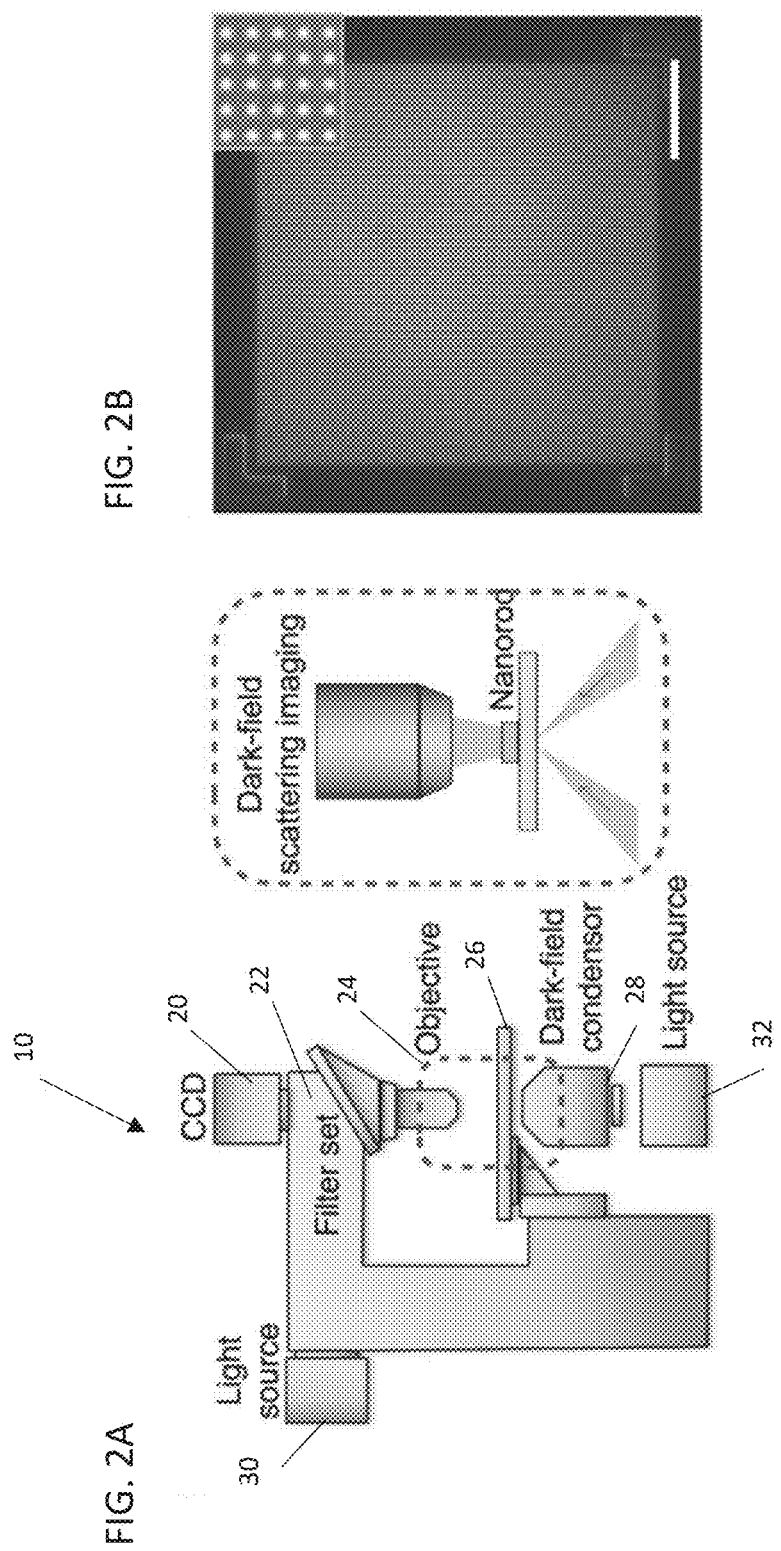
FIG. 2A and FIG. 2B illustrate an example of an optical system for the nano-plasmonic array for multiplexed single EV analysis.

FIG. 2A illustrates an example of an optical system for the nano-plasmonic array for multiplexed single EV analysis (NEXT readout system), that integrates dark-field imaging with multi-channel fluorescence imaging. FIG. 2A illustrates an example upright microscope setup 10 for dark-field (transmission) and epifluorescence dual-mode imaging. The charge-coupled device (CCD) 20 of the optical setup can be used to capture electromagnetic radiation emitted, scattered, or reflected by reporter groups (e.g., fluorescent antibodies) on the labeled target EVs captured on the nano-plasmonic array. In some embodiments, the upright microscope setup 10 comprises a filter set 22 to process/filter electromagnetic radiation, a microscope stage 26 on which a substrate with a nano-plasmonic array is placed under an objective 24, a camera, e.g., CCD, 20 to capture the radiation processed by the filter set 22. The system also includes a dark field condenser 28, arranged below the stage 26, a primary light source 30 (e.g., an LED light source) arranged to illuminate the microscope stage 26 from above, and a secondary light source 32, arranged to illuminate the microscope stage 26 from below through a dark-field condenser 28. In some embodiments, the dark-field scattering imaging is used to illuminate the nano-plasmonic array from below to capture emitted, scattered, or reflected electromagnetic radiation from the nano-plasmonic array through the objective 24.

In some examples, the second light source 32 and the dark-field condenser 28 of the dark-field scattering imaging system can be disposed above the objective 24 to illuminate the microscope stage 26 from above.

In this system, the location of captured EVs or nano-sized particles can be detected by dark-field imaging and their marker positivity can be detected by fluorescence imaging. In this case, dark-field scattering signals can be also amplified by an underlying plasmonic substrate.

FIG. 2B illustrates an example of a dark-field scatter image of the nanostructure arrays. An inset shows a zoomed image of the nanostructure arrays. In some embodiments, the nanostructure arrays may be nanorod arrays, and each nanorod is separated by 2 µm.

EXAMPLES

The disclosure is further described in the following examples, which do not limit the scope of the invention described in the claims.

Example 1—Characterizing a Nano-Plasmonic Array System

We investigated plasmonic enhancements in EVs. We captured biotinylated EVs on glass and nPLEX-FL substrates, and subsequently labeled the captured EVs with streptavidin-conjugated dyes (Cy5, FIG. 3E and AF488).

nPLEX-FL chips were prepared using the lithography methods described above. The chip was incubated overnight at room temperature with thiolated biotin polyethylene glycol (PEG) ($10 \times 10^{-3}$ m in PBS, PG2-BNTH-1k, Nanocs). After washing with PBS, an equimolar mixture of streptavidin molecules conjugated with either Alexa Fluor 488, Cy3, Cy5, or Cy5.5 (Biolegend) was incubated for 10 min. The concentration of each fluorescence dye was diluted to be 2.5 ag mL-1, except Alexa Fluor 488-conjugated streptavidin (25 µg mL-1 in PBS) due to the weak fluorescence signal compared to other channels.

Figures 3A, 3B, 3C, 3D, 3E, 3F, 3G, 3H, 3I, 3J:
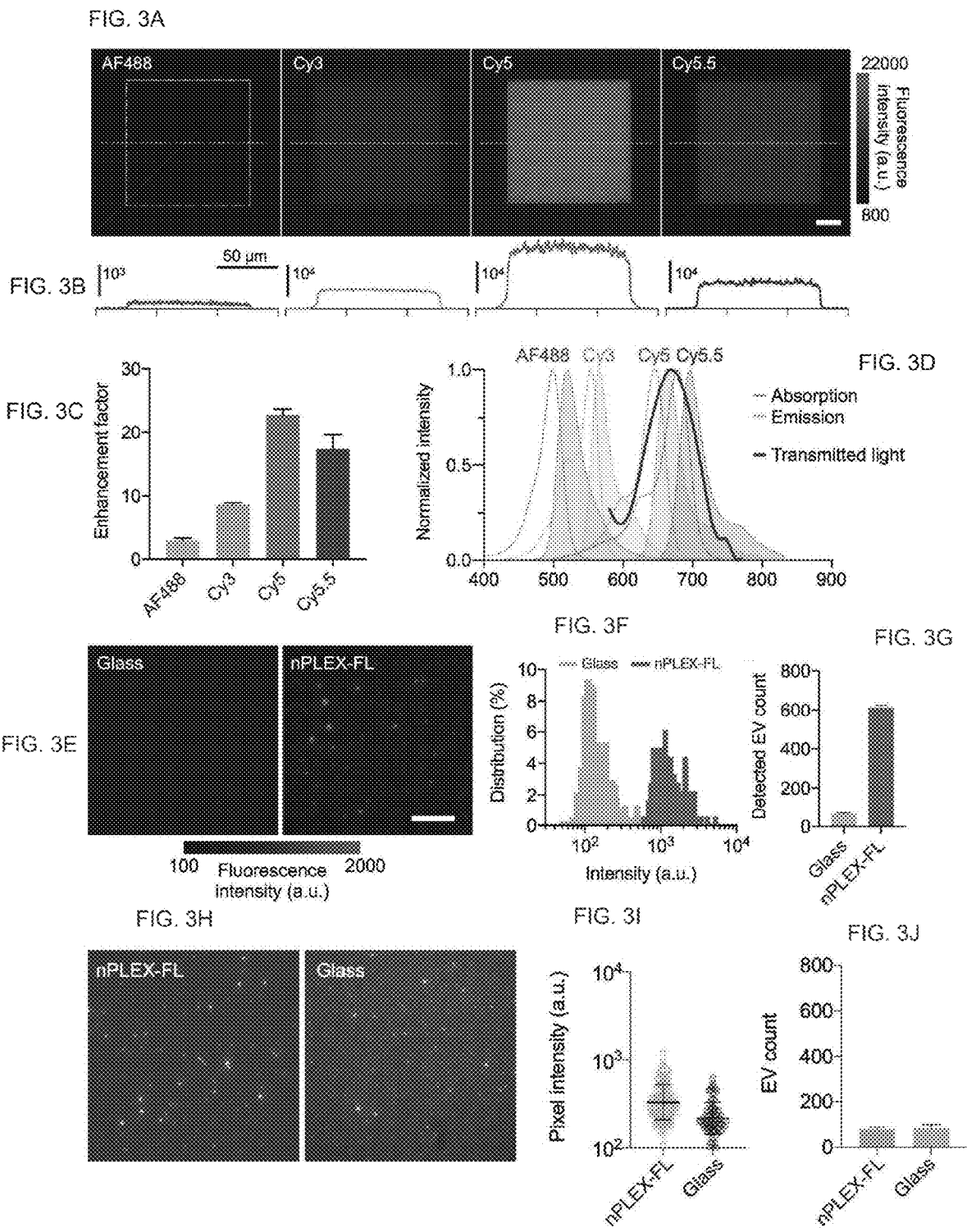
FIG. 3A to FIG. 3J are images and graphs of fluorescence used to characterize a system for detecting target EVs.

We used a polyphenolic proteins-based bioadhesive layer to capture the same amounts of EVs on different substrates (glass and Au) and investigated fluorescence intensities and detectable EV counts. The averaged signal enhancement factors in terms of fluorescence intensity after background correction were measured to be 1.54 for AF488 and 8.60 for Cy5 (FIG. 3F). The overall signal enhancement in the captured EVs was less prominent than the streptavidin monolayer coating (c.f. FIGS. 3C and 3F), likely because of the thickness difference between EVs and streptavidin monolayer; the electromagnetic fields are stronger near the surface. Nevertheless, we could detect an order-of-magnitude larger number of Cy5-labeled EVs on the nPLEX-FL chip compared to a glass substrate, indicating higher sensitivity attained by the plasmon-enhanced signal amplification (FIG. 3G).

We also observed comparable mean pixel intensities and EV counts for the AF488-labeled EVs on both nanohole chip and glass (see FIG. 3H). This indicates that the plasmon enhancement on Cy5 dyes unveils EVs with weak fluorescence signals otherwise undetected without signal enhancement (glass substrates) or with weak enhancement (AF488). Hence, we assign low abundant or key EV markers in the Cy5 channel in the subsequent validation study for the maximum signal enhancement.

In particular, FIG. 3A is a series of fluorescence images of the nano-plasmonic arrays/chips coated with four colors of fluorophore-conjugated streptavidin (AF488, Cy3, Cy5, and Cy5.5). The scale bar in FIG. 3A is 20 μm. Nanohole arrays were made in a 100×100 μm² sized square area highlighted by white dashed boxes, e.g., the white dashed box shown in the fluorescence image using AF488.

FIG. 3B illustrates cross-sectional intensity profiles along the grey horizontal dashed lines in FIG. 3A. The plasmon enhancement in different fluorescence channels is tested using a molecular monolayer. The Au nanohole surface is functionalized using thiolated biotin polyethylene glycol derivatives (thiol-PEG-biotin), and fluorophore-conjugated streptavidin molecules are immobilized on the biotinylated Au surface. To prevent fluorescence quenching by underlying Au substrates, the Au surface is functionalized with thiol-PEG-biotin (1 kDa, 6-8 nm) and neutravidin (60 kDa, 4-5 nm), which results in an adhesion layer of 10-13 nm in thickness. FIG. 3A and FIG. 3B show the strong signal enhancements in the 100×100 μm² sized square area of nanohole gratings (highlighted by a white dashed box) compared to the flat Au area (outside of the square, FIG. 3B).

FIG. 3C illustrates an example enhancement factor (EF) of fluorescence intensity in different fluorescence channels. The signal enhancement is most dominated in the Cy5 channel, and the EF of fluorescence intensity in the nanohole area in comparison to flat Au areas is 23 fold.

FIG. 3D illustrates an example plasmon-supported light transmission spectrum through nanohole arrays overlaid with the absorption/emission spectra of fluorophores. The Cy5.5 and Cy3 intensities are also increased by 17 and 9 folds, respectively, when the AF488 signal is only increased by 3-fold. These EFs in the different channels can be explained by spectral overlaps between plasmon-supported light transmission through nanoholes and absorption/emission spectral of fluorophores. The light transmission peak is measured at 667 nm, which is most overlapped with Cy5 absorption (649 nm) and emission (666 nm) peaks followed by Cy5.5 and Cy3.

FIGS. 3E to 3I illustrate example plasmonic enhancements on EVs. FIG. 3E indicates that biotinylated EVs are captured on glass and substrates of the nano-plasmonic arrays, and subsequently labeled the captured EVs with streptavidin-conjugated dyes. The captured EVs are labeled with Cy5-conjugated streptavidin, and then imaged. The scale bar in FIG. 3E is 10 μm. FIG. 3H indicates biotinylated EVs captured on the device surface coated with an L-3,4-dihydroxyphenylalanine (L-DOPA)-based bioadhesive layer, and the captured EVs were labeled with AF488-conjugated streptavidin, and then imaged. FIG. 3I illustrates a comparison of the mean fluorescence intensities and FIG. 3J illustrates the number of captured EVs in FIG. 3H in the region of interest (ROI) between the nanohole chip and glass substrate. An L-DOPA-based bioadhesive layer is used to capture EVs in the same densities on different substrates (glass and Au) and investigated fluorescence intensities and detectable EV counts.

Furthermore, FIG. 3F illustrates example histograms of pixel intensities of captured EVs of FIG. 3E. The averaged signal enhancement factors in terms of fluorescence intensity after background correction were measured to be 1.54 for AF488 and 8.60 for Cy5. The overall enhancement is less significant than the streptavidin monolayer coating in FIG. 3C likely due to localized electromagnetic fields, which are strongest near the surface shown in FIG. 3C.

FIG. 3G illustrates the number of detected EVs of FIG. 3E between the nanohole chip and glass substrate. The fluorescence intensity is normalized by background signals defined by the sum of the mean fluorescence intensity in the absence of EV and three times the standard deviation. An order-of-magnitude larger number of Cy5 labeled EVs on the nPLEX-FL chip is detected to be compared to a glass substrate, indicating higher sensitivity attained by the plasmon-enhanced signal amplification. In contrast, a comparable mean pixel intensities and EV counts for the AF488-labeled EVs is observed on both nanohole chip and glass. The observed difference is that the plasmon-induced signal amplification of Cy5 unveils the smaller EVs with weak signals, which are undetected on the glass substrates. Hence, for its maximal spectral overlap with the plasmon resonance, Cy5 dye is chosen to label low abundant intravesicular markers.

Example 2—Single EV Measurements

We applied the nPLEX-FL technology to demonstrate its feasibility on the multiplexed single EV analysis. We used glioblastoma cell lines for testing: Gli36-WT and Gli36-EGFRvIII (overexpressing human EGFRvIII). EGFR and EGFRvIII are biomarkers of interest for glioblastoma as amplification of EGFR and its variant (EGFRvIII) occur frequently in glioblastoma. The presence of protein markers including 1) ubiquitous EV tetraspanin combination named CD-pan (CD9, CD63, and CD81); 2) GAPDH; 3) EGFR; and 4) EGFRvIII was examined by nPLEX-FL and bench-marked against western blotting analysis as a standard method (see FIGS. 6A and 6B).

EVs were isolated from conditioned cell culture media. Nanoparticle tracking analysis showed that the isolated EVs used in this study have a size distribution ranging 50-200 nm with an average diameter of 100 nm, also confirmed by transmission electron micrographs. The isolated EVs were biotinylated, diluted in pure buffer (1-10×10⁸ EVs mL-1 phosphate-buffered saline (PBS)), and captured on the neutravidin-coated gold nanohole surface. The captured EVs were immune-labeled against membrane (i.e., CD63, EGFR) and/or intravesicular markers (i.e., GAPDH) and imaged under a fluorescence microscope. Because most EVs are smaller than the diffraction limit, the average blob size of the detected vesicles in fluorescence images was about 500 nm (8 pixels with a pixel size of 63 nm). Single EVs generated detectable fluorescence signals, confirmed by scanning electron micrograph. Some doublet EV showed a higher intensity in the streptavidin channel. Particles imaged larger than 1 μm (or 16 pixels) were considered large aggregates and excluded in our analysis.

We chose well-established EV markers for a proof-of-principle demonstration of EV profiling and subpopulation sorting based on marker signals. In consideration of fluorescence signal enhancement, we assigned 1) green dye (AF488) to high abundance/easy-to-detect markers and 2) far-red dye (Cy5) to low abundance/hard-to-detect markers. FIG. 4A shows representative nPLEX-FL images of biotinylated EVs labeled against CD-pan (AF488), streptavidin (Cy3), and GAPDH (Cy5). We chose GAPDH as a representative intravesicular marker, which is commonly used as a control for many other quantitative methods (e.g., western blotting, qPCR). We varied EV concentrations and counted the number of captured EVs. Line scan (FIG. 4B) showed high signal-to-noise ratios and signal heterogeneity for the chosen markers on individual vesicles. We then analyzed the raw intensity data for marker profiling of EVs. For a given marker, we identified two subpopulations-marker-positive and marker-negative, which can be separated by the intensity cutoff (mean+2× standard deviation of negative controls). Roughly 40% of the captured streptavidin-positive vesicles were CD-pan positive, and of the CD-pan-positive EVs, a fraction expressed GAPDH (25%) (FIG. 3C). The false-positive rate in a control sample (no EV) was negligible for both streptavidin staining (<1%) and antibody staining (<0.2%). Based on the negative control data, we set a threshold of 1% for positivity.

In particular, FIG. 4A illustrates that EVs from the Gli36-WT cell line are biotinylated and captured on the nanohole surface. Individual EV are detected through staining with fluorescent Cy3-streptavidin (top left). For molecular profiling, EVs are labeled with fluorescent antibodies against transmembrane EV markers (CD63) and intravesicular markers (GAPDH). Multiple EV markers are chosen to detect and classify single EVs based on marker expression levels. AF488 dye to high abundance/easy-to-detect markers and Cy5 to low abundance/hard-to-detect markers are assigned. FIG. 4A shows representative nPLEX-FL images of Gli36-WT derived EVs labeled against CD63 (AF488) and GAPDH (Cy5). GAPDH is chosen as a representative intravesicular marker, which is commonly used as a control for many other quantitative methods (e.g., Western blotting, qPCR).

FIG. 4B illustrates line scans showing high signal-to-noise for the chosen markers in this example. Gray shading highlights EV positions. Line scan shows high signal-to-noise and heterogeneity for the chosen markers on individual vesicles.

FIG. 4C illustrates EV subtyping. The raw intensity data shown in FIG. 4B is then analyzed for the marker expression and EV subtyping. For a given marker, we identified two subpopulations: marker-positive and marker-negative, which can be separated by the intensity cutoff of 100. Roughly half the captured vesicles had CD63 (46%), and of the CD63+ EVs, a fraction expressed GAPDH (58%). It is confirmed that strong overlapping (>95%) of GAPDH+ EVs with CD63+ EVs. A higher fraction of Cy5-GAPDH+ EVs on the nanohole chip is observed than other substrates, which could be attributed to the plasmon-derived signal amplification in the Cy5 red channel.

Example 3—Demonstration of Tumor Diagnostic Potential

FIG. 5A to FIG. 5E illustrate an example measurement of tumor markers of captured EVs to demonstrate tumor diagnostic potential of the new systems and methods. EVs from three different cell lines (Gil36-WT, Gli36-EGFRvIII, MCF7) were biotinylated and captured on a nanohole array surface, and EVs were labeled with fluorescent antibodies against the CD-pan marker panel (CD9, CD63, and CD81) as well as tumor markers which comprise EGFR in FIG. 5A and EGFRvIII in FIG. 5B. Spots with dotted circles indicate tumor marker-positive EVs in FIGS. 5A and 5B.

Figures 5A, 5B, 5C, 5D, 5E:
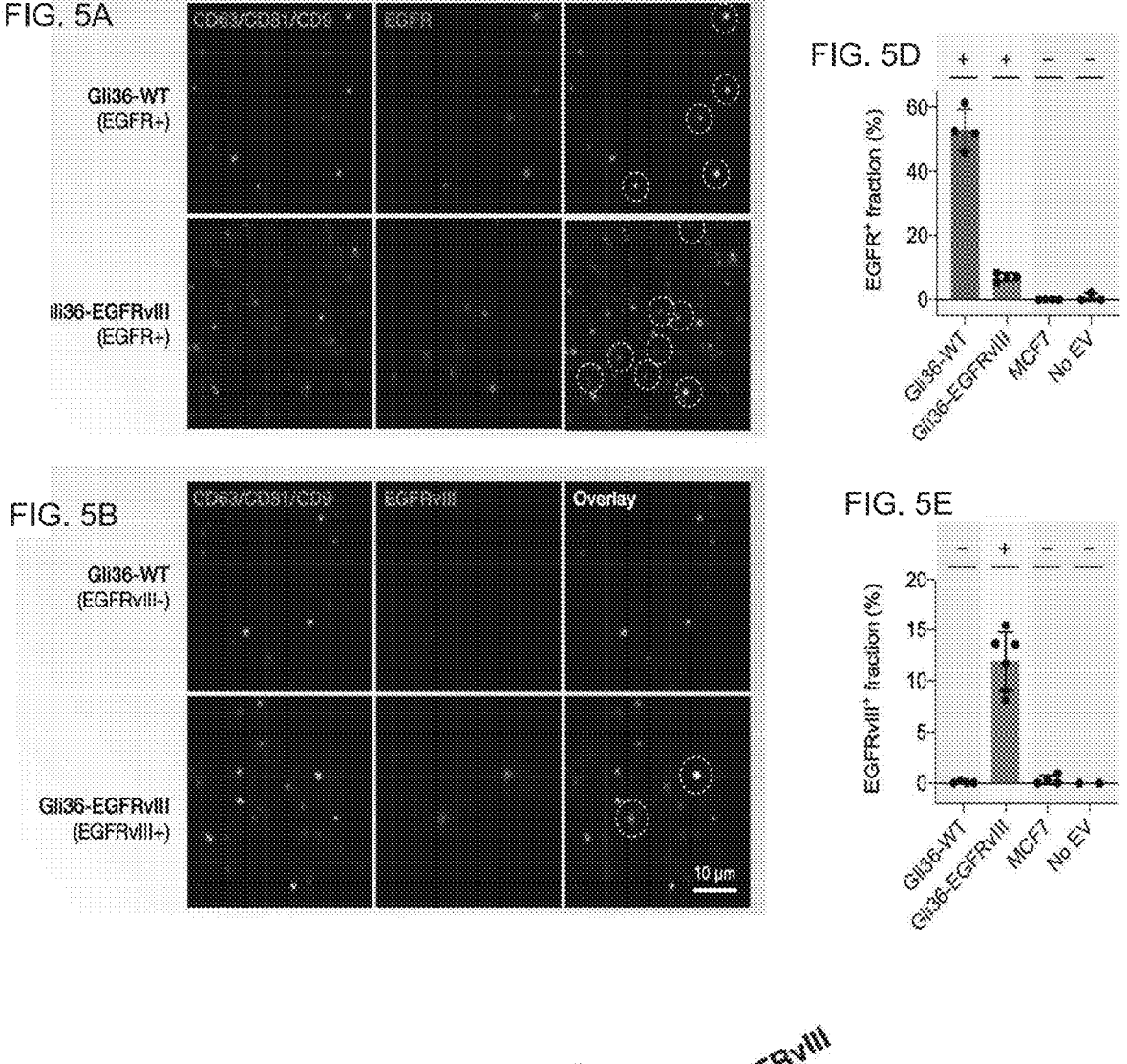
FIG. 5A to FIG. 5E illustrate measurements of tumor markers of captured EVs.

FIG. 5C illustrates a Western blot analysis of EGFR expression in Gli36-WT, Gli36-EGFRvIII, and MCF-7 cell lines. MCF-7 cells served as a negative control for EGFR expression. Blotting antibodies against GAPDH were used for loading control.

The bar graphs in FIGS. 5D and 5E illustrate EV subtyping. Fraction (%)=$EV_{CD-pan+Target}$+/$EV_{CD-pan+}$. As shown in FIG. 5D, a significant fraction of Gli36-WT EV were positive for EGFR (54%) whereas a small fraction of Gli36-EGFRvIII are positive for EGFR (7%). As shown in FIG. 5E, somewhat over 10% of Gli36-EGFRvIII vesicles were positive for EGFRvIII, while Gli36-WT and MCF7 showed the EGFRvIII-positive fractions (<1%) below the threshold for statistical significance. A negative control was prepared with the same procedure with no EV incubation.

To further test the diagnostic potential for clinical applications, we spiked $\approx 10^{10}$ EVs from Gli36-WT and Gli36-EGFRvIII cell lines into 1 mL human plasma samples. EVs were isolated from the spiked plasma samples using a size exclusion column (Izon column), biotinylated, and then loaded onto the chip (1-5 μL). The captured EVs were labeled against CD-pan (AF488), streptavidin (Cy3), and EGFR or EGFRvIII (Cy5). We implemented a decision tree algorithm with a nested gating strategy to classify EV populations based on EGFR and EGFRvIII signals (FIG. 6A). Briefly, particles labeled with Cy3-conjugated streptavidin were first detected and prescreened by size exclusion (<1 μm) to exclude large aggregates from the analysis. Among particles positive for streptavidin, we defined EVs positive for CD-pan markers (CD9, CD63, and CD81). Then, the prescreened EVs were sub-gated with target glioblastoma markers of EGFR or EGFRvIII. We conducted the power analysis for a Mann-Whitney test using two independent groups (EV positive and negative) to calculate the necessary EV sample size (n>100) given the statistical power of 0.9 and the effect size of 0.43. Given the EV surface coverage of 0.1-0.5 EV $\mu m^{-2}$, the minimum area required is roughly 200-1000 m². Yet, we used fluorescence images (n=4) in a full field-of-view (FOV) (120 μm×100 μm) and sampled thousands of vesicles per measurement to ensure statistical significance and robust analysis.

FIGS. 6B and 6C show biomarker distribution analyses on a single-EV level. We plotted bivariate histograms from three-channel fluorescence images with a FOV of 120 μm×100 μm. On average, we detect about 4200 particles positive for streptavidin in single images (minimum=3604, maximum=5057 EVs, FIG. 6D). We observed 10-15% positivity of streptavidin-positive particles for CD-pan markers (FIG. 6E). The lower fraction of CD-pan+streptavidin+ particles in the plasma samples compared to that in the pure-buffer (PBS), could be attributed to the presence of lipoproteins and plasma protein aggregates in human plasma. For marker profiling, the detected EVs positive for CD-pan were screened for target markers of EGFR and EGFRvIII. For plasma samples spiked with EVs from Gli36-WT and Gli36-EGFRvIII cell lines, about 10-20% of detected EVs were positive for EGFR in both samples (FIG. 6F). However, roughly 10% of EVs were positive for EGFRvIII only in the plasma samples with Gli36-EGFRvIII EVs, while the other sample with Gli36-WT EVs showed less than 1% positive EV fraction, which is below the threshold (FIG. 6G). Comparable biomarker positivity for EGFR and EGFRvIII was observed between the plasma samples and the pure-buffer samples.

These results show that glioblastoma EVs can be used to detect EGFRvIII mutation proteins.

Example 4—Characterization of EVs Isolated from Tumor Cell Lines

The nPLEX-FL technology was extended to demonstrate its feasibility on the multiplexed single EV analysis. Glioblastoma (GBM) cell lines were used for testing: Gli36-WT and Gli36-EGFRvIII, a clone of Gli36 EV that is positive for EGFRvIII mutation. EVs were collected from conditioned cell culture media and membrane filtered, biotinylated, immobilized on the nanohole array chip surface, and immune-labeled against membrane (i.e., CD63, EGFR) and/or intravesicular markers (i.e., GAPDH). The isolated EVs used in this study have a size distribution ranging 50-200 nm with an average diameter of 100 nm and the high purity determined by western blotting for ubiquitous EV protein markers (CD9, CD63, and CD81, FIG. 7B). The avidin-functionalized Au chip showed high specificity for bioti-nylated EV capture, which was confirmed by electron microscopy.

Figure 7B:
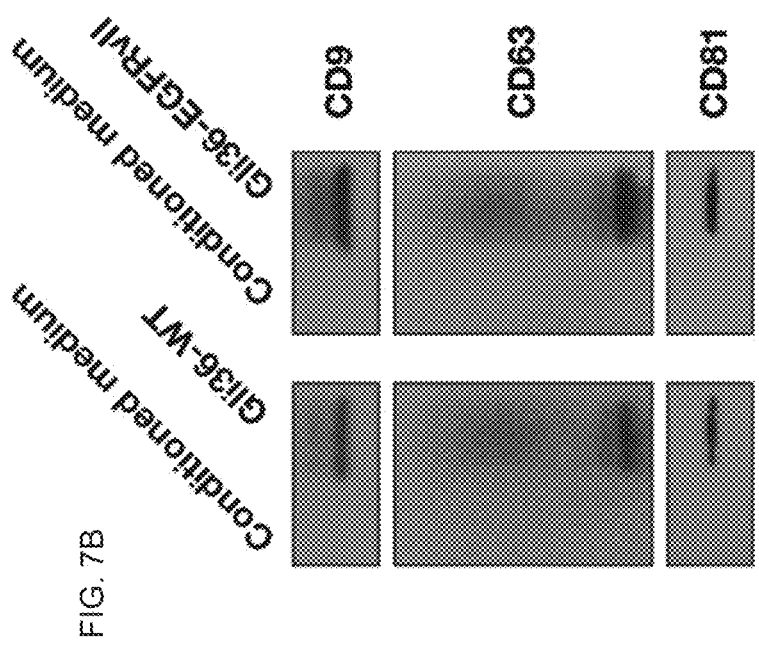
FIG. 7A and FIG. 7B illustrate an example characterization of EVs isolated from Gli36-WT and Gli36-EGFRvIII.
Figure 7A:
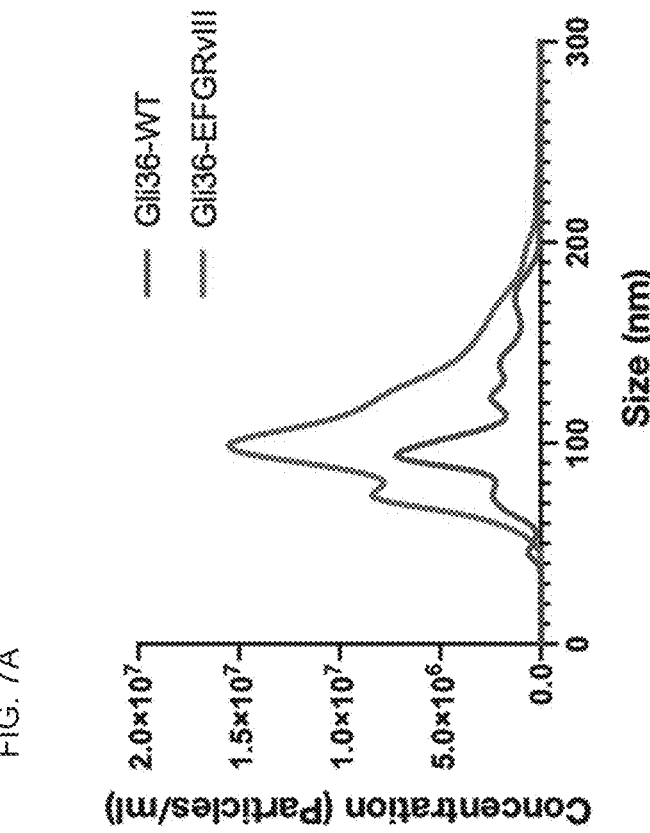

In particular, FIG. 7A illustrates a size distribution graph of Gli36-WT and Gli36-EGFRvIII EVs obtained by nan-oparticle tracking analysis (NTA). FIG. 7B illustrates a Western blot measurements of Gli36-WT and Gli36-EG-FRvIII EVs to determine pan-CD marker expression levels (CD9/CD63/CD81) in bulk.

Example 5—Characterization of EVs Varied in Concentrations

Figures 8A, 8B:
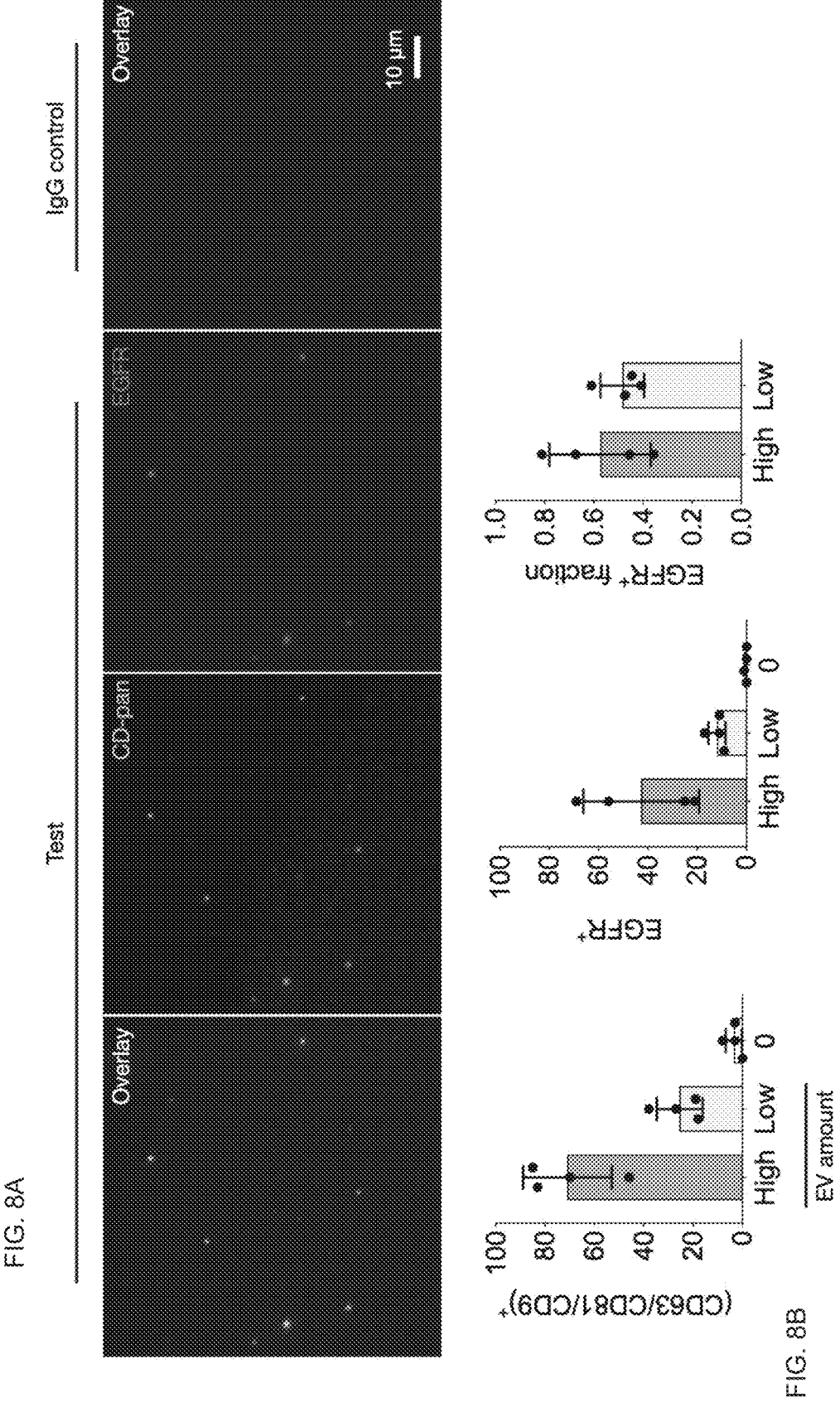
FIG. 8A and FIG. 8B illustrate an example characterization of EVs varied in concentrations.

FIG. 8A illustrates EVs from the OVCA429 cell line biotinylated and captured on the nano-plasmonic array device. EVs were collected from conditioned cell culture media and membrane filtered, biotinylated, and immobilized on the nanohole array chip surface. Captured EVs were labeled against the pan-CD marker which is a combination of CD9, CD63, and CD81 (AF488), and EGFR (Cy5). EVs were artificially color-coded for visual aid. The scale bar in FIG. 8A is 10 μm. The three bar graphs in FIG. 8B illustrate various EV concentrations (4-fold difference) and the number of captured EV. Regardless of the EV concentrations, roughly half the CD-pan+ EVs expressed EGFR. Individual vesicles we identified by staining EV with Cy3-streptavidin.

Example 6—Negative Controls to Demonstrate Test Sensitivity

Figure 9B:
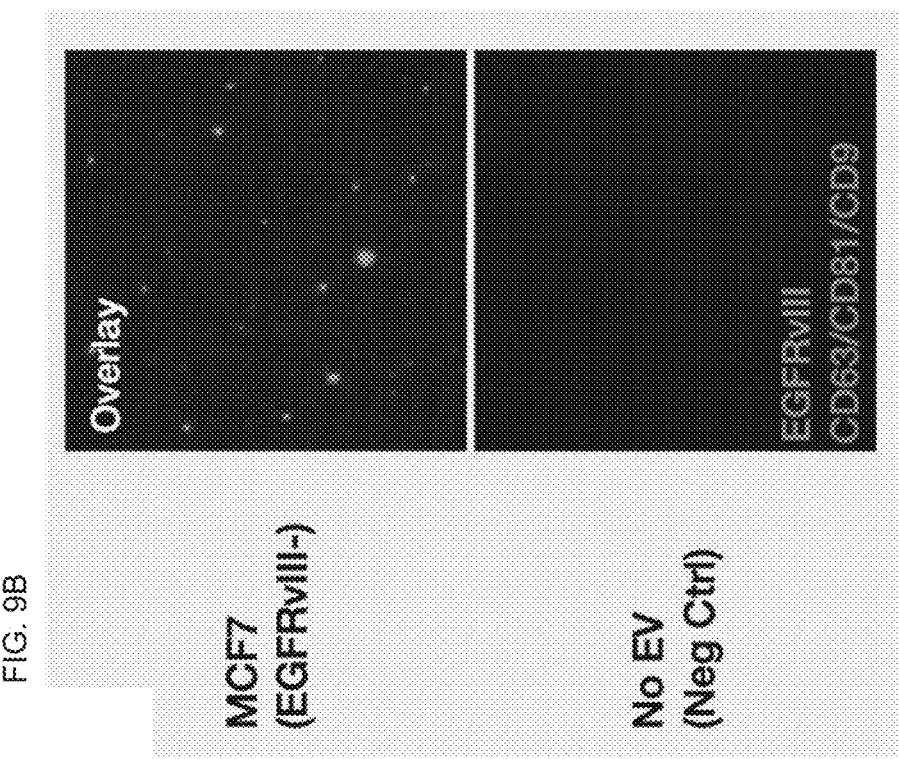
FIG. 9A and FIG. 9B illustrate negative controls to demonstrate test sensitivity and specificity of the captured EVs.
Figure 9A:
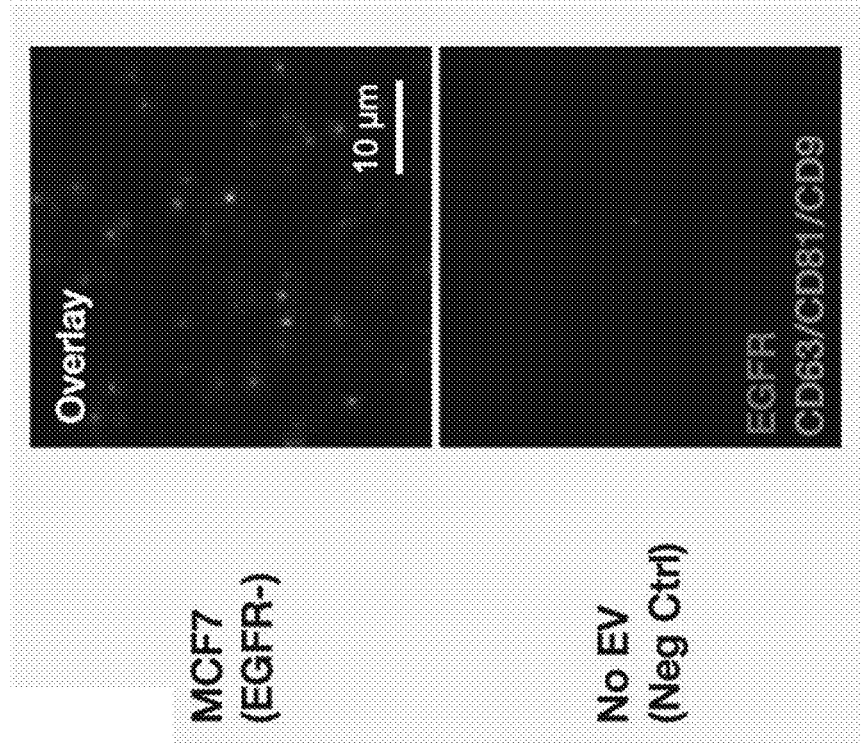

FIG. 9A to FIG. 9B illustrate negative controls to dem-onstrate test sensitivity and specificity of the captured EVs. EVs from the MCF7 cell line were collected from condi-tioned cell culture media and membrane filtered, bioti-nylated, and immobilized on the nanohole array chip sur-face. EVs were labeled with the CDpan marker which is a combination of CD63/CD81/CD9 (AF488) and EGFR (shown in FIG. 9A) or EGFRvIII (Cy5) (shown in FIG. 9B).

The negative control (e.g., no EVs) was prepared with the same procedure with no EV incubation. FIG. 9A to FIG. 9B indicate a statistical significance of the present nano-plas-monic array sensor system for detecting target EVs.

Example 7—Optical Characterization of Nanorod Arrays

FIG. 12A to FIG. 12B illustrate an example optical characterization of nanorod sensor arrays. The graph of FIG. 12A illustrates the results of finite-difference time-domain (FDTD) simulations showing optical resonance peaks for different sizes of nanorods having lengths of 40, 60, 80, 100, and 120 nm. The optical tuning is important to maximize fluorescence signal enhancement by the nanorod's surface plasmon resonance. The nano-plasmonic array can have a specific size/dimension for each of the nanorods based on a size of the target EVs and/or other requirements (e.g., to detect a specific wavelength of SPR) in analysis steps.

The graph in FIG. 12B shows the experimental results of spectral shifts and intensity changes of dark-field scattering as the surface refractive index increases from 1.33 to 1.45. Water and ethanol mixtures in different mix rations were prepared and applied to the nanorod arrays to vary the refractive indices from 1.33 to 1.45. The amount of spectral shifts were measured and plotted against the surface refrac-tive index. The peak wavelength with the surface refractive index of 1.33 was used as a reference to calculate spectral shifts. EV binding to the nanorods increases the surface refractive index, shifting the resonance peak. The EV bind-ing event can be detected by measuring either spectral shifts or scattering light intensity changes.

Example 8—Optical Resonances of Nanorods vs Nanodisks

Figures 13A, 13B, 13C, 13D, 13E, 13F, 13G, 13H:
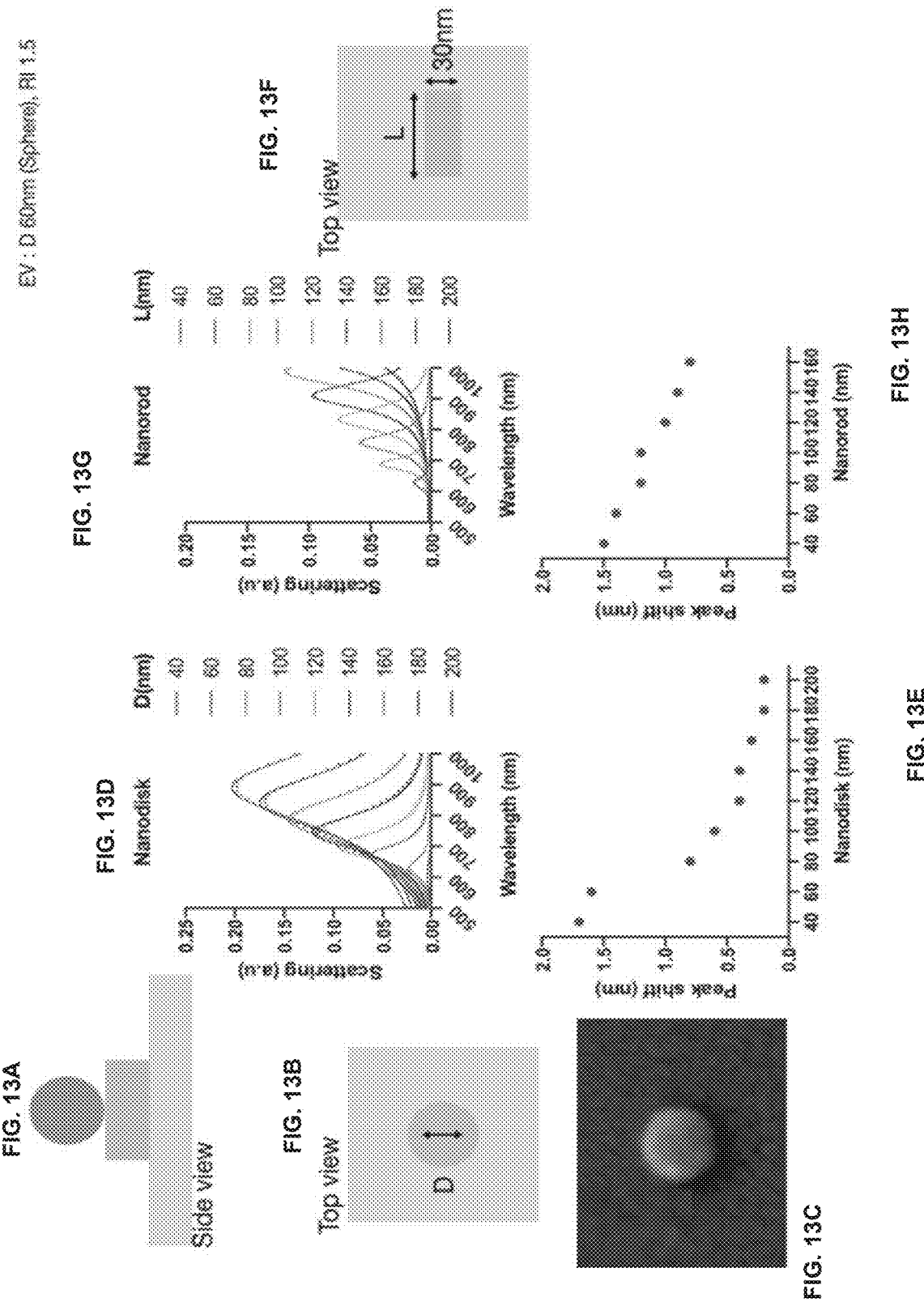
FIG. 13A to FIG. 13H illustrate finite-difference time-domain (FDTD) simulations showing optical resonances of nanorod and nanodisk arrays in different sizes.

FIG. 13A is a representation of a side view of an EV captured on a nanorod. FIG. 13B is a representation of top view of a nanodisk in an array. FIG. 13C is a scanning electron microscope image of a top view of an EV on a nanostructure.

FIG. 13D is a graph showing scattering intensities (a.u) of nanodisks having different diameters of 40, 60, 80, 100, 120, 140, 160, 180, or 200 nm, calculated by FDTD simulations. As shown, the scattering intensity increase with the diameter of the nanodisk, and the wavelength of peak scattering intensity also increases with nanodisk diameter.

FIG. 13E is a graph showing peak shifts (nm) of nan-odisks having different diameters from 40 to 200 nm. As shown, the peak shift is highest for a nanodisk having a diameter of 40 nm, drops sharply from 60 to 80 nm diameters, and then continues to decrease as diameter increases until leveling off at about 180 nm.

FIG. 13F is a representation of a top view of a nanorod having length L and a width of 30 nm. FIG. 13G is a graph showing scattering intensities (a.u) of nanorods having different lengths of 40, 60, 80, 100, 120, 140, 160, 180, and 200 nm. As shown, the peak scattering intensity increases with wavelength and with length of the nanorods.

FIG. 13H is a graph showing peak shifts (nm) of nanorods having different lengths from 40 to 120 nm. As shown, the peak shift decreases with nanorod length The nano-plasmonic array can be designed to have nano-structures with specific sizes/dimensions of nanorods or nanodisks based on a size of the target EVs as well as other requirements (e.g., to detect a specific wavelength of SPR) for detecting target EVs. Any shapes similar to nanorods or nanodisks can be also used as plasmonic nanostructures to amplify fluorescent and dark-field signals.

Example 9—Finite-Difference Time-Domain (FDTD) Simulations

FIG. 14A to FIG. 14C illustrate FDTD simulations show-ing spectral shifts of dark-field scattering upon EV binding to nanodisks in different locations and distances to the substrate.

FIG. 14A is a representation of Scenario 1 of a first EV binding location and its detected peak wavelength, along with a corresponding graph. FIG. 14B is a representation of Scenario 2 of a second EV binding location and its detected peak wavelength, along with a microscope image showing electromagnetic waves. FIG. 14C is a representation of Scenario 3 of a third EV binding location and its detected peak wavelength, along with a microscope image showing electromagnetic waves concentrated on the nanodisk surface. The results show single EV binding to the nanodisk surface in various binding scenarios can be detected by measuring spectral shifts of dark-field scattering peak wavelength.

Example 10—Real Time EV Binding Experiment

Real time binding of the EVs to nanodisks was analyzed using the systems and methods described herein.

Figures 15A, 15B, 15C, 15D:
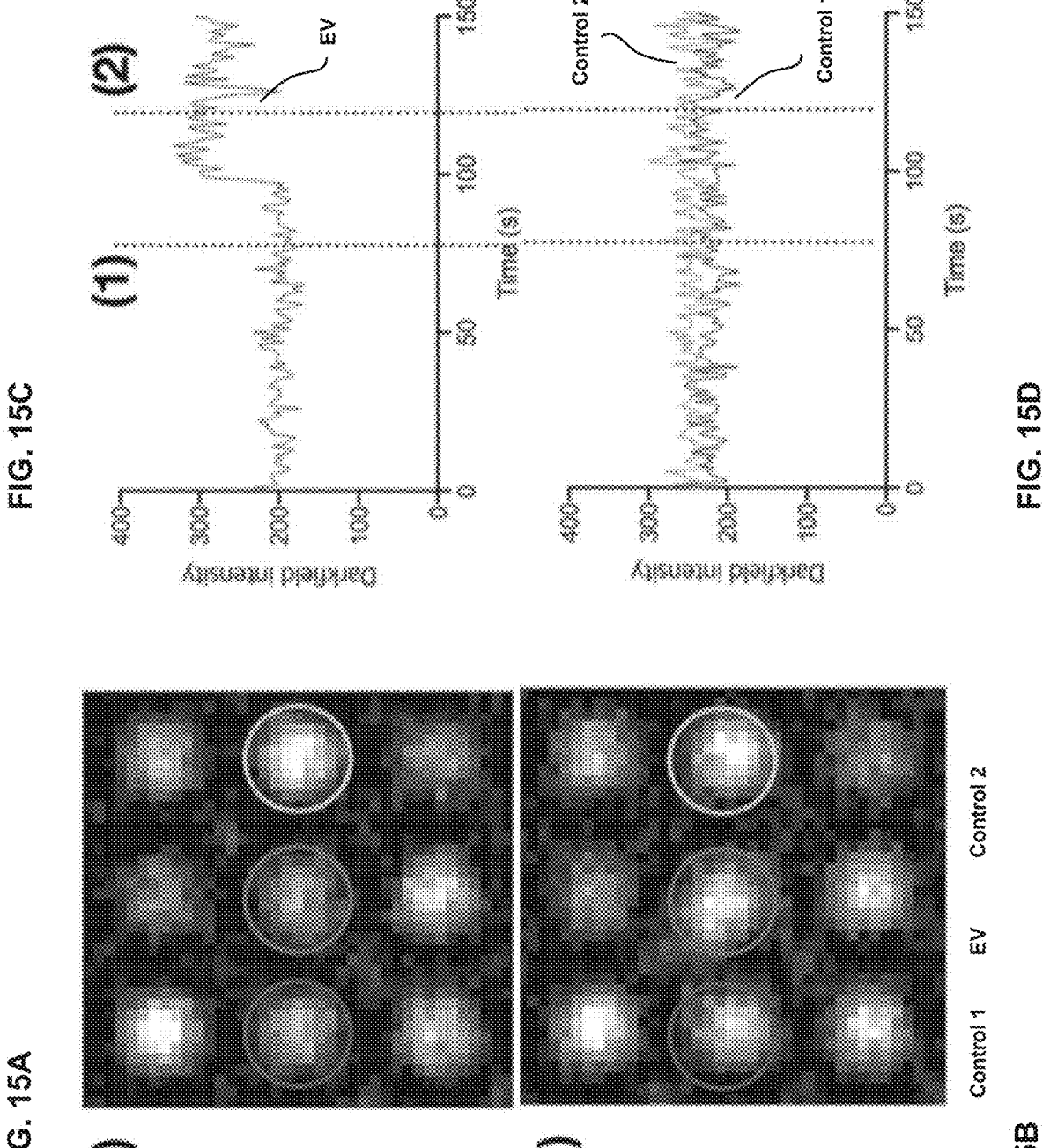
FIG. 15A to FIG. 15D illustrate an example of EV binding detection by measuring dark-field scattering intensity changes.

FIG. 15A to FIG. 15D illustrate an example of EV binding detection by measuring dark-field scattering intensity changes in real time. Timeline (1), as shown in FIG. 15A, is before EV binding to the nanodisk in the center of the array (middle circle). Timeline (2), as shown in FIG. 15B, is after EV binding to the nanodisk in the center of the array (middle circle).

The graph of FIG. 15C shows real time measurements showing an abrupt intensity change at time point (2) upon EV binding to the center nanodisk. In particular, FIG. 15C shows that the intensity is increased at 100 seconds when an EV binds to the nanodisk, as the signal difference shown in FIG. 15A and FIG. 15B (middle circle).

The graph of FIG. 15D shows real time measurements showing no abrupt intensity changes of two controls that show no binding to any of the nanodisks in the array. In particular, FIG. 15D shows the changes in the dark-field scattering intensity over time for the control nanodisks (Control 1 and Control 2 in FIG. 15A and FIG. 15B), which have no affinity ligands. There is no EV binding and thus no intensity change is measured. The vertical dashed lines (1) and (2) in FIG. 15C and FIG. 15D indicate the time points when FIG. 15A and FIG. 15B are taken.

Example 11—Spectral Shifts of Dark-Field Scattering of Nanodisks

Figures 16A, 16B, 16C:
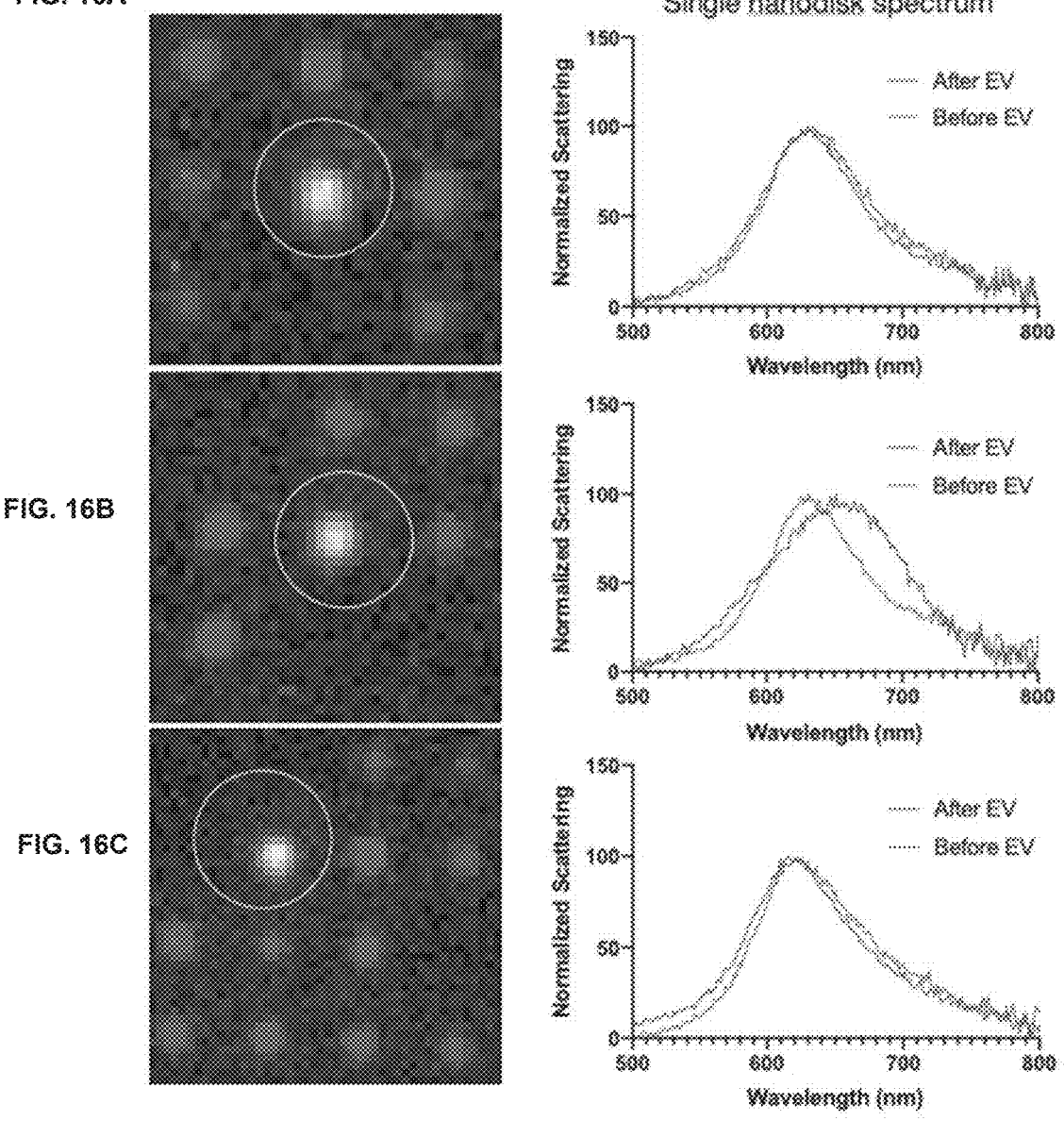
FIG. 16A to FIG. 16C illustrate an example of EV binding detection by measuring spectral shifts of dark-field scattering of nanodisks and corresponding graphs of the single nanodisk spectrum of the wavelength vs normalized scaling.

The methods and nanodisk arrays described above were used to analyze spectral shifts of dark-field scattering caused by the nanodisks. FIG. 16A to FIG. 16C illustrate the results of how the EV binding can be detected by measuring spectral shifts of dark-field scattering by the nanodisks. EV binding is confirmed by overlays with EV fluorescence images. EVs were labeled by specific fluorescence probes to locate the nanodisks that have captured EVs.

FIG. 16A to FIG. 16C show overlaid images of fluorescence channels for EVs and dark-field scattering of nanodisks, which show EVs are captured on the nanodisks (circles in the images). Dark-field scattering spectra before and after EV binding on those nanodisks are shown on the right, demonstrating that EV binding to the nanodisk surface induces spectral shifts.

The image in FIG. 16A shows a central nanodisk that shows a fluorescent signal indicating EV binding. The accompanying graph of a single nanodisk spectrum shows a slight spectral shift, where no shift means a perfect overlay, in normalized scattering before or after EV binding.

The image of FIG. 16B shows a central nanodisk with a change in fluorescence indicating EV binding. The accompanying graph of a single nanodisk spectrum shows a pronounced rightward (increase in peak wavelength) shift in normalized scattering after EV binding.

The image in FIG. 16C shows a nanodisk that shows a fluorescent signal indicating EV binding. The accompanying graph of a single nanodisk spectrum shows no significant shift in normalized scattering before or after EV binding, where no shift means a perfect overlay.

Example 12—Plasmon Enhancements of Dark-Field and Fluorescence Signals with Nanodisks of Different Diameters As shown in FIG. 17 and FIGS. 18A-D, the nanoplasmonic arrays can be designed to have nanodisks having specific diameters based on a corresponding dark-field/fluorescent labels for detecting target EVs. A monolayer of fluorescence molecules is formed on the top of the nanodisk arrays, and the fluorescence signals on the nanodisk and substrate were measured.

Figure 17:
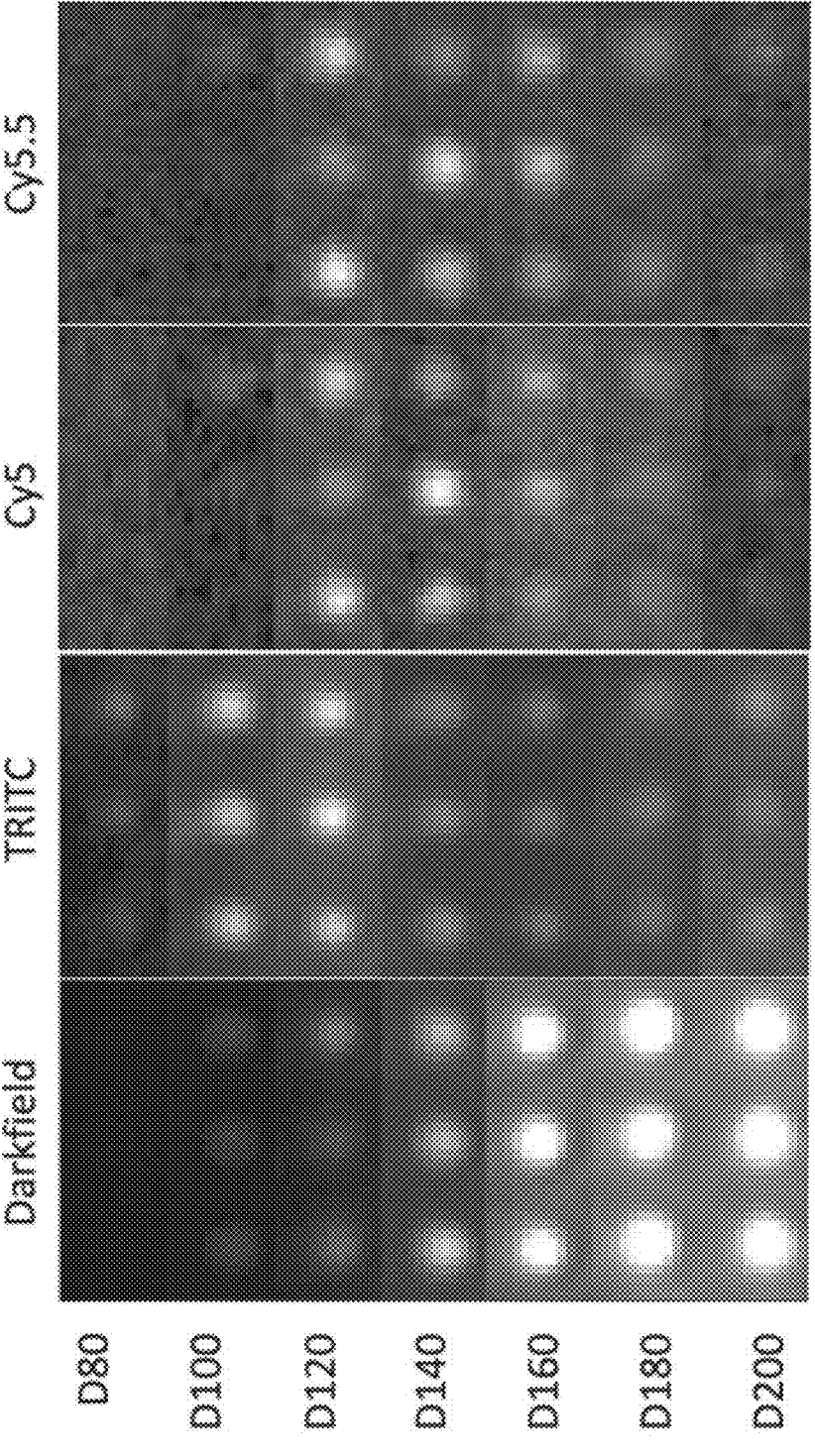
FIG. 17 illustrates plasmon enhancements of dark-field imaging and three different fluorescent signals (TRITC, Cy5, and Cy5.5) for different diameters of nanodisks from 80 to 200 nm.

FIG. 17 illustrates plasmon enhancements of dark-field and three different fluorescent signals (TRITC, Cy5, and Cy5.5) for nanodisks having different diameters of 80, 100, 120, 140, 160, 180, and 200 nm.

FIGS. 18A to 18D are graphs that illustrate plasmon enhancements of dark-field and fluorescence signals for different sizes of nanodisks. FIG. 18A is a graph of plasmon intensity for dark-field measurements corresponding to different diameters of nanodisks of 80, 100, 120, 140, 160, 180, and 200 nm, and as shown the level increases with diameter up to about 180 nm and then slightly declines at 200 nm.

FIG. 18B is a graph of plasmon intensity of TRITC corresponding to different diameters of nanodisks of 80, 100, 120, 140, 160, 180, and 200 nm, and as shown the level increases sharply with diameter up to 120 nm and then declines sharply to 140 nm, declines slightly to 180 nm, and then increases again to 200 nm.

FIG. 18C is a graph of plasmon intensity of Cy5 corresponding to different diameters of nanodisks of 80, 100, 120, 140, 160, 180, and 200, and as shown the level decreases slightly from 80 to 100 nm, then increases sharply with diameter up to 120 nm and then declines to 200 nm.

FIG. 18D is a graph of plasmon intensity of Cy5.5 corresponding to different diameters of nanodisks of 80, 100, 120, 140, 160, 180, and 200 nm, and as shown the level remains the same from 80 to 100 nm, increases sharply with diameter from 100 up to 140 nm, then declines sharply to 180 nm, and then declines slightly to 200 nm.

TRICT and Cy5 show the maximum intensity when they are coated on 120 nm (diameter) nanodisks while Cy5.5 showed the maximum intensity on the 140 nm diameter nanodisk.

Example 13—Isolation and Preparation of EVs

EVs were isolated from a cell culture of Gli36-WT (ATCC), Gli36-EGFRvIII (generated from Gli36-WT through lentivirus transduction), and MCF-7 cells (ATCC) grown in DMEM (Cellgro), OVCA429 cells (ATCC) cultured in RPMI-1640 medium (Cellgro). Media were supplemented with 10% fetal bovine serum (FBS, Thermo Fisher), 100 U/mL penicillin, and 100 µg/mL streptomycin (Cellgro) at 37° C. in 5% $CO_2$. Furthermore, cell lines were tested and were free of mycoplasma contamination (MycoAlert™ mycoplasma detection kit, Lonza).

For EV isolation and biotinylation, EVs were incubated in DMEM with 1% exosome-depleted FBS (Thermo Fisher) for 48 hours before EV collection. The conditioned medium was collected and centrifuged, e.g., at 300×g for 5 minutes, and then supernatant was filtered through, e.g., through a 0.2 µm membrane filter (Millipore Sigma).

EVs were isolated using both standard ultracentrifugation (UC) and size-exclusion chromatography (SEC) methods:

(i) for UC, the filtrates were concentrated by centrifugation at 100,000×g for 1 hour. After the supernatant was removed, the EV pellet was washed with a buffer or saline solution, such as PBS, and centrifuged at 100,000×g for 1 hour. The EV pellet was resuspended in PBS, and (ii) for SEC, the filtrates were loaded onto a centrifugation filter (Centricon® Plus-70 Centrifugal Filter (MWCO=10 kDa, Millipore Sigma), and centrifuged at 3,500×g for 30 minutes at a low temperature, such as 4° C.

After concentration, the volume was adjusted to 1 mL with PBS. SEC was performed with modifications. Briefly, 10 mL syringe (BD Biosciences) with a nylon net with 20 μm pore size (Millipore Sigma) at the bottom was prepared and packed with 10 mL of Sepharose CL-4B (GE healthcare). The concentrates were loaded on top and 6 fractions of 1 mL were collected under constant gravitational flow by adding PBS on top of the column. The fractions 4 and 5 were used for EV isolation. These were loaded onto Amicon Ultra-2 Centrifugal Filter (MWCO=10 kDa, Millipore Sigma) and centrifuged at 3,500×g for 30 minutes at 4° C. The isolated EVs were stored at −80° C. until further measurements.

The isolated EVs were resuspended in buffer or saline solution, e.g., PBS and incubated with the capture agent, such as EZ-Link Sulfo-NHS-LC-Biotin (Thermo Fisher) for a sufficient time, e.g., 30 minutes, at room temperature. For example, a 20-fold molar excess of sulfo-NHS-biotin to EV protein was used in a 0.5 mL volume. Approximately 4 to 6 biotins are incorporated per molecule. Excess biotin was then removed utilizing the Exosome Spin Columns, MW3000 (Thermo Fisher) per the kit instructions. The prepared EVs were filtered using a 0.22 μm centrifugal filter (Ultrafree®, Millipore).

Example 14—Plasmon-Enhanced EV Detection on NPOP Substrate

This example compares an NPOP (nanoparticles on nanopillars) substrate and a glass substrate for EV detection. We fluorescently labeled EVs with AF555 or AF647 dyes and the same aliquots were applied to the substrates. Because substrates are made of different materials, we coated the substrate surface with a cell-adhesion layer (Cell-tak) to ensure the same surface chemistry.

TFP Dye was prepared as follows. First we prepared 27.5 mM of Azido-dPEG®$_{12}$-TFP ester (Quanta Biodesign) with Anhydrous DMSO (Sigma). Then we prepared 25 mM of AFdye DBCO with Anhydrous DMSO (Sigma), and then mixed equal volume of Azido-dPEG®$_{12}$-TFP ester and AFdye DBCO at RT for 2 hours with a HulaMixer® (ThermoFisher Scientific).

EVs were labeled as follows. First, we mixed 0.2 μL of TFP-AF555 or AF647 dye, 3 μg of 300 ng SKBR3 EVs in PBS, and 2 μg of 100 mM sodium bicarbonate and incubated for 1 hour at RT in a dark condition. We then loaded the labeled-EVs onto a Zeba™ Micro Spin Desalting Columns (ThermoFisher Scientific) to remove unbounded TFP dye, centrifuged at 1,500×g for 2 minutes, and collected the filtrates. We then reloaded the filtrates onto the Zeba™ Micro Spin Desalting Columns and centrifuged at 1,500×g for 2 minutes and collected the filtrate.

The substrates and EV samples were prepared as follows. We first washed the substrates, and glass was incubated in absolute ethanol for 5 minutes and washed with water. The NPOP were washed with water, and we removed the water with nitrogen gas. We attached the PDMS (4 mm wells, 2 mm thickness) onto the substrate to make EV attachment.

We prepared the Cell-Tak® cell and tissue adhesive solution (Corning) to attach the EV on the substrate without surface chemistry. We then mixed 30 μg of Cell-Tak, 10 mM sodium bicarbonate, and 17 mN sodium hydroxide and added the resulting mixture into the wells and incubated for 30 minutes for surface absorption. We then washed the substrate with water 3 times, added fluorescently labeled EVs with dilution in PBS and incubate for 30 minutes, at dilutions of 1:50, 1:100, 1:200, 1:400, 1:800, 1:1600, 1:3200, and washed the unbounded EVs with PBS for 3 times. We then removed the PDMS wells and added Prolong Gold™ antifade mounting solution (ThermoFisher scientific) onto the substrate and mounted the coverslip.

Images were taken and analyzed as follows. We obtained 3 images of EVs signals by an upright fluorescent microscopy (Zeiss) with 5 second exposure time for each channel (AF555 and AF647) with 40× objective lens. We converted raw czi files to Tiff image files and loaded images to ImageJ® Fiji and subtract the background signal. We analyzed the EV number and intensities for each channel using the ComDet Plugin with fixed parameters (approximate particle size: 4.00 pixels, intensity threshold (in SD): 3.00 around). We described the differences of EV counts, EV intensities, and mean of intensities of AF555 or AF647 labeled EVs in different dilution factors using Prism software (GraphPad).

The results are shown in FIGS. 19A-19D, which show that a higher number of EVs can be detected when EVs are captured on the NPOP substrate than on a glass substrate. This is due to signal enhancement by the plasmonic substrate that amplifies EVs' fluorescence signals. Overall signals were amplified and higher numbers of EVs were detected for both AF555 and AF647 channels. The enhancement can occur for dyes with excitation wavelengths longer than 530 nm.

FIG. 19A shows fluorescence images of AF555- or AF647-labeled EVs on a glass substrate or on a NPOP substrate. The same amount of labeled EVs in different dilution factors was mounted onto the adhesive molecule-treated substrates. Scale bars, 50 μm.

FIG. 19B shows a pair of graphs for comparison of EV counting numbers in different dilution factors on glass (black line) or NPOP substrates (lighter line). The NPOP substrate showed a higher number of EVs detected in both AF555- or AF647-labeled EVs. Left panel, AF555-labeled EVs; right panel, AF647-labeled EVs. Error bars represent the mean±SD.

FIG. 19C is a pair of histogram plots for comparison of EV intensities (1:1600 dilution) in glass (black graph) and NPOP substrate (light line). The intensities of detected EVs were higher in NPOP substrate. Left panel, AF555-labeled EVs; right panel, AF647-labeled EVs.

FIG. 19D is a bar graph for quantitative analysis of signal enhancement. The NPOP substrate enhanced the signal intensities by 2 fold (AF555) and 9 fold (AF647) compared with the glass substrate (*P<0.05; P<0.01; *P<0.001; ****P<0.0001), as assessed by two-way ANOVA with Bonferroni's multiple comparisons test. Error bars are shown as mean±SD from the three different images.

Example 15—Comparison of Different Linkers to Capture EVs on the NPOP

We tested different thiol linkers on the NPOP substrates. The linker has two functions. First, once their carboxylated groups are activated by EDC/NHS, the linkers provide binding sites for EVs through covalent bonding between the activated functional groups on the linker and EVs. Second, the linker plays a role as a passivation layer (mock) to minimize non-specific molecular binding. In this test, we showed that thiol-PEG-COOH (1 kDa) shows a greater difference between desired (EDC/NHS) and undesired (mock) EV capture than other tested linkers.

We labeled EVs by mixing 0.2 µg of TFP-AF555 dye, 3 µg of 300 ng of EVs in PBS, and 2 µg of 100 mM sodium bicarbonate and incubated for 1 hour at RT under dark conditions. We loaded the labeled-EVs onto the Zeba™ Micro Spin Desalting Columns (ThermoFisher Scientific) to remove unbounded TFP dye and centrifuged at 1,500×g for 2 minutes and collected the filtrates. We reloaded the filtrates onto the Zeba™ Micro Spin Desalting Columns and centrifuged at 1,500×g for 2 minutes and collected the filtrate.

We prepared the NPOP substrates and captured EVs by washing the substrate with water. We then removed the water with nitrogen gas and placed the substrates in a humid chamber. We functionalized the NPOP substrate with COOH molecules of different lengths. For mercaptoundecanoic acid (MUA), we mixed 10 mM of 11-mercaptoundecanoic acid (Sigma) and 1-Octanethiol (Sigma) in absolute ethanol, added the mixture onto the NPOP substrate, and incubated for 2 hours at RT. We then washed with ethanol and water. For SH-PEG-COOH (0.4 kDa), we prepared the 0.25 mM of SH-PEG-COOH (0.4 kDa, Nanocs) in water, added the mixture onto the NPOP substrate, incubated for 4 hours at RT, and washed with water. For SH-PEG-COOH (1.0 kDa), we prepared the 0.25 mM of SH-PEG-COOH (1.0 kDa, Nanocs) in water, added the mixture onto the NPOP substrate, incubated for 4 hours at RT, and washed with water.

We then treated the NPOP substrate with: 0.1 M MES (pH 6.0) for Mock treatment and the mixture of 50 mM EDC (ThermoFisher Scientific) and 125 mM of sulfo-NHS (ThermoFisher Scientific) in 0.1 M MES (pH 6.0) for 7 minutes to capture the EVs by covalent bonding. We then washed the NPOP substrate with MES and PBS, incubated the AF555 labeled-EVs for 30 minutes at RT under dark conditions, washed the unbounded EVs with PBS 3 times, and added Prolong Gold™ antifade mounting solution (ThermoFisher scientific) onto the substrate and mount the coverslip.

Images were taken and analyzed as follows. We obtained 10 images of EVs signals using an upright fluorescent microscopy (Zeiss) with 5 second exposure time for AF555 channel with 40× objective lens. We converted raw czi files to Tiff image files, loaded the images to ImageJ® Fiji and subtracted the background signal, and analyzed the EV number and intensities for each channel using the Com-Det™ Plugin with fixed parameters (approximate particle size: 4.00 pixels; intensity threshold (in SD): 3.00 around). We described the differences of EV counts for AF555 labeled EVs in different length using Prism software (Graph-Pad).

The results are shown in FIGS. 21B and 21C. FIG. 21B is a series of representative images for EV capture by functionalization with MUA (1.7 nm length), SH-PEG-COOH (0.3 kDA, 2.8 nm length), and SH-PEG-COOH (1.0 kDa, 7 nm length) with or without EDC/NHS activation. Scale bars, 50 µm.

FIG. 21C is a bar graph of EV counting showed SH-PEG-COOH showed the least non-specific EV binding (ns, not significant; ****$P<0.0001$ compare with the mock treatment, as assessed by two-way ANOVA with Bonferroni's multiple comparisons test). Error bars are shown as mean±SD from the ten different images.

Figure 21D:
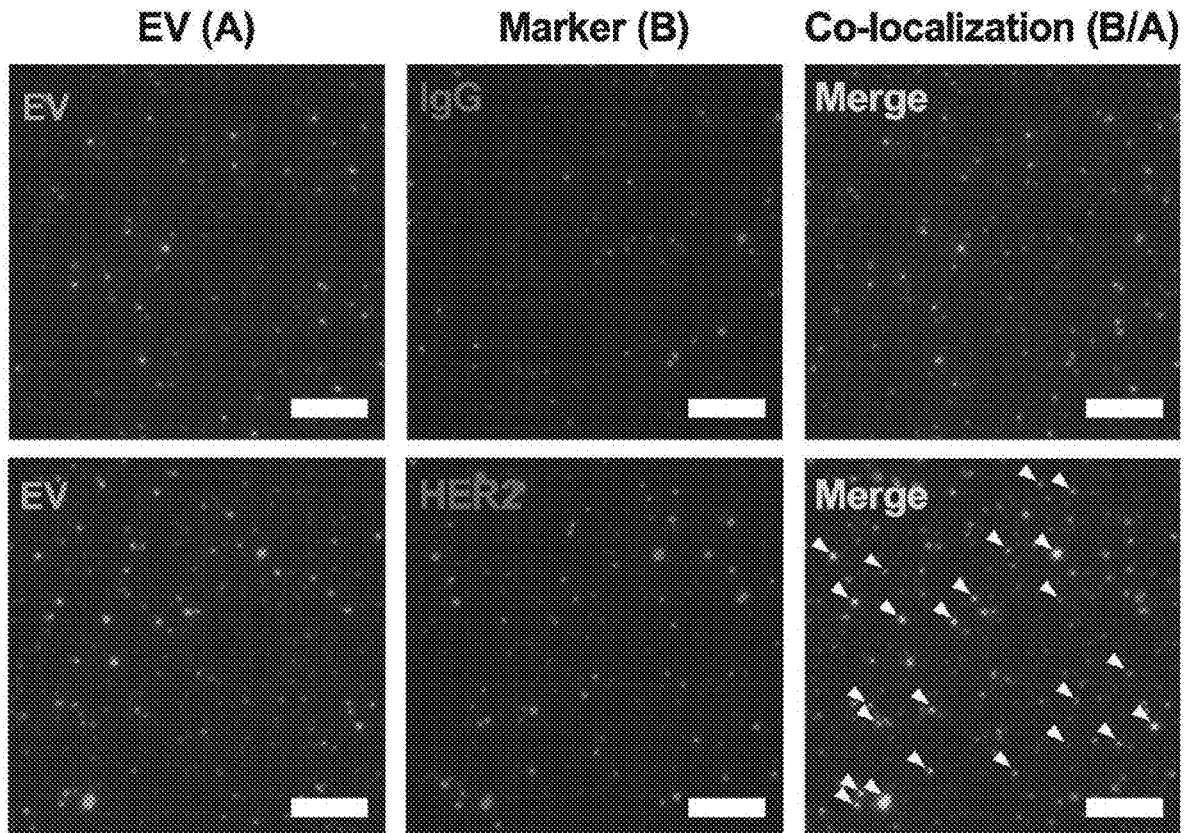
FIG. 21D is a series of representative images for different color-labeled EVs (green) and markers (IgG or HER2)(red). The percentages of co-localization (Marker/EV merged images) were analyzed for evaluating the differential marker expression. The co-localized signals (B/A) were indicated by white arrowheads. Scale bars, 10 μm.

FIG. 21D is a series of representative images for different color-labeled EV (green) and marker (IgG or HER2, red).

The percentages of co-localization (Marker/EV) were analyzed for evaluating the differential marker expression. The co-localized signals were indicated by white arrow heads. Scale bars, 10 µm.

Example 16—Multi-Channel Detection for Molecular Profiling of Tumor Cell-Derived EVs Using QUAD Markers by Single EV Analysis on NPOP Substrates This example explores molecular profiling of tumor-derived EVs from four different breast cancer cell lines. These cell lines represent four major subtypes of breast cancer based on their HER2, ER, and PR expression levels. We tested these cell line-derived EVs for our QUAD markers (MUC1, HER2, EGFR, and EpCAM) and compared their levels in EVs and their parental cells. The results show each cell line and their EVs show different positive levels for these QUAD markers, but the overall molecular profiling patterns are similar between EVs and their originating cells, supporting the use of EVs as surrogate markers of tumors.

We prepared the NPOPs and captured EVs as follows. We washed the substrate with water, and removed the water with nitrogen gas and placed the NPOP into a humid chamber. We functionalized the NPOP substrate with 0.25 mM of SH-PEG-COOH (1.0 kDa, Nanocs) and 0.75 mM of SH-mPEG (0.35 kDa, Nanocs) in water for 4 hours at RT. We then washed the NPOP substrate with water and treated it with the mixture of 50 mM EDC (ThermoFisher Scientific) and 125 mM of sulfo-NHS (ThermoFisher Scientific) in 0.1 M MES (pH 6.0) for 7 minutes to capture the EVs by covalent bonding. We then incubated the EVs for 30 minutes at RT in under dark conditions to generate SKBR3 EV, MCF7 EV, BT474 EV, and MDA-MB-231 EV, which were washed with PBS 3 times.

We immunostained for QUAD markers and labeled EVs as follows. We fixed and permeabilized the EVs with 4% paraformaldehyde (Electron Microscopy Sciences) and 1× Perm/Wash Buffer (BD) for 10 minutes at RT, washed with PBS for 3 times, and blocked the EVs and NPOP substrates with 100% SuperBlock™ (PBS) Blocking Buffer (ThermoFisher Scientific) for 30 minutes at RT. We then added primary antibodies against MUC1, HER2, EGFR, EpCAM in 10% SuperBlock™ (PBS) Blocking Buffer in PBS and incubate for 30 minutes at RT (at the following concentrations: 0.08 µg/mL Mouse IgG1 isotype control (Invitrogen, 14-4714-85); 0.4 µg/mL Mouse IgG1 isotype control (Invitrogen, 14-4714-85); 2.0 µg/mL Mouse IgG1 isotype control (Invitrogen, 14-4714-85); and 0.08 µg/mL Mouse IgG2b isotype control (Biolegend, 400301); 0.4 µg/mL Mouse IgG1 MUC1 (Invitrogen, MA1-06503); 2.0 µg/mL Mouse IgG1 HER2 (Biolegend, 324402); 0.08 µg/mL Mouse IgG2b EGFR (Abcam, ab30); and 0.08 µg/mL Mouse IgG1 EpCAM (Abcam, ab85987). We then washed the NPOP substrate with PBST 3 times.

We then added Goat anti-Mouse IgG (H+L) Cross-Adsorbed Secondary Antibody, Alexa Fluor™ 647 (ThermoFisher Scientific) in 10% SuperBlock™ (PBS) Blocking Buffer in PBS and incubated for 20 minutes at RT, washed the NPOP substrate with PBST 3 times, added 0.25 µg/mL of Wheat Germ Agglutinin, Alexa Fluor™ 555 Conjugate (ThermoFisher Scientific) for 20 minutes at RT in a dark condition, washed the NPOP substrate with PBST 3 times, and added Prolong Gold™ antifade mounting solution (ThermoFisher scientific) onto the substrate and mount the coverslip.

Images were taken and analyzed as follows. We obtained 4 images of EVs signals (AF555) and antibody signal (AF647) using an upright fluorescent microscopy (Zeiss) with 5 sec exposure time with 40× objective lens. We converted raw czi files to Tiff image files, loaded images using ImageJ™ Fiji, and subtracted the background signal. We then analyzed the number of EV and antibody signal and their co-localization using the ComDet™ Plugin with fixed parameters (approximate particle size: 4.00 pixels; intensity threshold (in SD): 3.00 around). We described the co-localization percentage (Co-localized EV/Total EV), Heatmap, and co-relation plot using Prism™ software (Graph-Pad).

For flow Cytometry, we harvested the cultured cells by trypsinization, washed the cells 3 times by centrifugation and resuspended the pellet with PBS. We added 4% paraformaldehyde (Electron Microscopy Sciences) and 1×Perm/Wash Buffer (BD) and incubated for 10 minutes at RT. We then washed the cells 3 times by centrifugation and resuspended the pellet with PBS. We then added primary antibodies against MUC1, HER2, EGFR, and EpCAM in 10% SuperBlock™ (PBS) Blocking Buffer in PBS and incubated for 1 hour at RT at the following concentrations (1 μg/mL Mouse IgG1 isotype control (Invitrogen, 14-4714-85); 1 μg/mL Mouse IgG2b isotype control (Biolegend, 400301); 1 μg/mL Mouse IgG1 MUC1 (Invitrogen, MA1-06503); 1 μg/mL Mouse IgG1 HER2 (Biolegend, 324402); 1 μg/mL Mouse IgG2b EGFR (Abcam, ab30); and 1 μg/mL Mouse IgG1 EpCAM (Abcam, ab85987)). We then washed the cells 3 times by centrifugation and resuspended the pellet with PBS. We added Goat anti-Mouse IgG (H+L) Cross-Adsorbed Secondary Antibody, Alexa Fluor™ 488 (ThermoFisher Scientific) in 10% SuperBlock™ (PBS) Blocking Buffer in PBS and incubated for 30 minutes at RT. We then washed the cells 3 times by centrifugation and resuspended the pellet with PBS. We loaded the cells in the 96-well plate and read the signal intensities with Cytoflex® Flow Cytometer (Beckman Coulter).

We analyzed the differential expression of markers within the cell lines using median values of signals using Flowjo® software. The results are shown in FIGS. 22A-22E, which are images that demonstrate molecular profiling of tumor cell-derived EVs for the QUAD markers by single EV analysis on NPOP substrate.

Figures 22A, 22B, 22C, 22D, 22E:
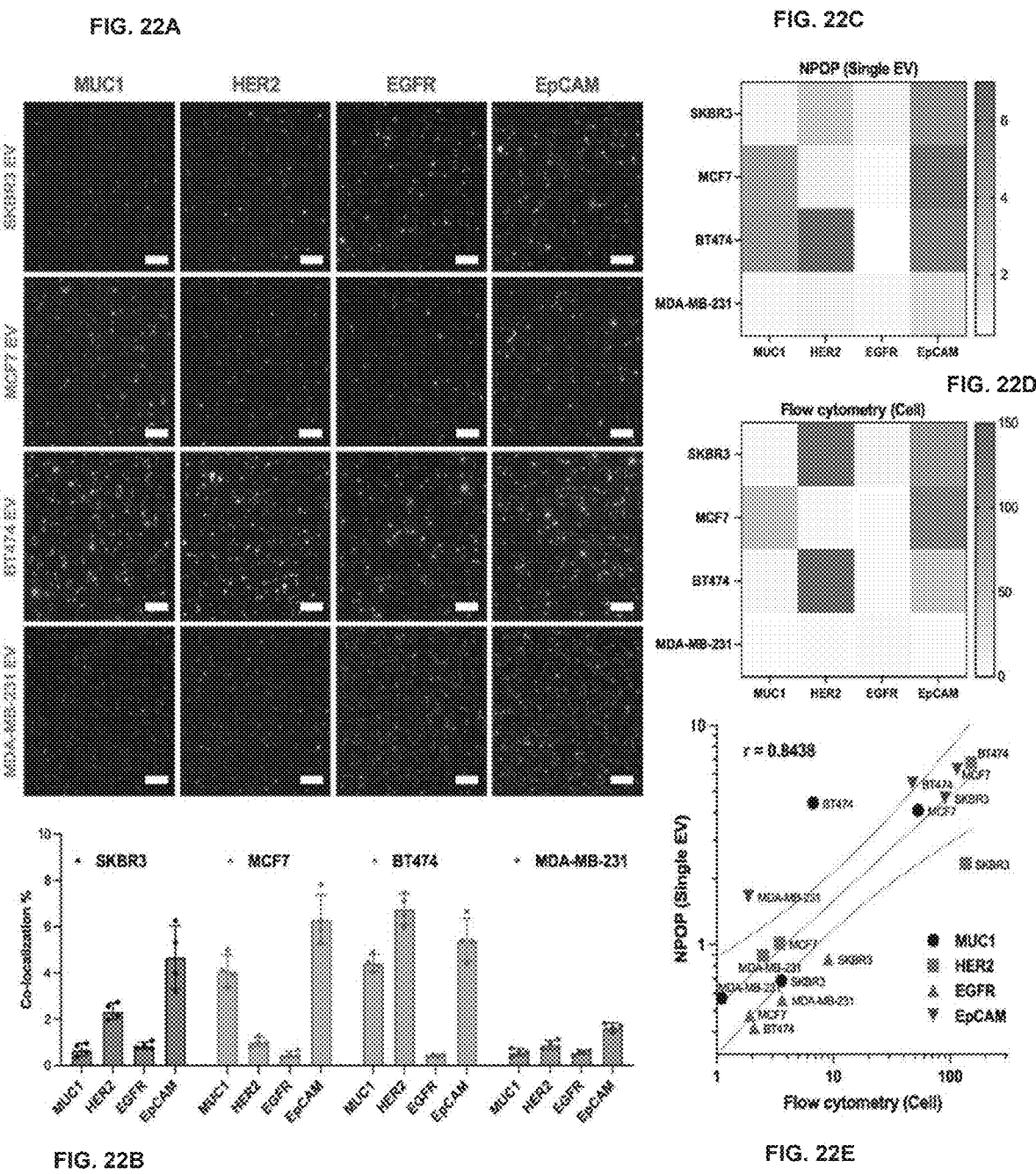
FIG. 22A is a series of representative images of multi-channel single EV analysis for QUAD marker (MUC1, HER2, EGFR, and EpCAM) profiling in EVs derived from four different breast cancer cell lines (SKBR3, ERPR−/HER2+; MCF7, ERPR+/HER2−; BT474, ERPR+/HER2+; MDA-MB-231, ERPR−/HER2−; scale bars, 10 μm).
FIG. 22B is a bar graph for the percentages of co-localization for the EVs and QUAD markers. Error bars are shown as mean±SD from the four different images.
FIGS. 22C-D are heatmaps that show the differential abundances of QUAD markers in four different tumor cell line-derived EVs, as assessed by single EV analysis (22C) and originated cell lines, as assessed by flow cytometry (22D).
FIG. 22E is a graph that shows a Pearson correlation coefficient revealing that the multi-channel single EV analysis showed similar molecular patterns to the flow cytometry (r=0.8438, P<0.0001). The percentage of co-localization from the multi-channel single EV analysis and flow cytometry were indicated in y- and x-axis, respectively. The solid orange line indicates the best linear fit. The two dashed lines indicate the 95% confidence interval.

FIG. 22A is a series of representative images of multi-channel single EV analysis for QUAD marker (MUC1, HER2, EGFR, and EpCAM) profiling in EVs derived from four different breast cancer cell lines. SKBR3, ERPR−/HER2+; MCF7, ERPR+/HER2−; BT474, ERPR+/HER2+; MDA-MB-231, ERPR−/HER2−. Scale bars, 10 μm.

FIG. 22B is a bar graph for the percentages of co-localization for the EVs and QUAD markers. Error bars are shown as mean±SD from the four different images.

FIGS. 22C-22D are a pair of heatmaps showing the differential abundances of QUAD markers in four different tumor cell line-derived EVs, as assessed by single EV analysis (21C) and originated cell lines, as assessed by flow cytometry (21D).

FIG. 22E is a dot plot for Pearson correlation coefficient revealed that the multi-channel single EV analysis showed similar molecular patterns to the flow cytometry (r=0.8438, P<0.0001). The percentage of co-localization from the multi-channel single EV analysis and flow cytometry were indicated in y- and x-axis, respectively. The solid light line indicates the best linear fit.

Example 17—Plasmon Enhancements on a Cy7 Channel

Imaging EVs in the Cy7 channel was challenging due to weak fluorescence signals generated from the dye and channel. However, by using the plasmon enhancement, we could significantly amplify EV fluorescence signals when EVs are captured on the NPOP substrate compared to other plain substrates (glass or gold). This led to higher EV detection sensitivity.

The methods used in this Example are the same as described in Example 14, except for the use of TFP-Cy7 rather than TFP-AF dyes. The results are shown in the different graphs of FIGS. 23A-23C.

Figure 23A:
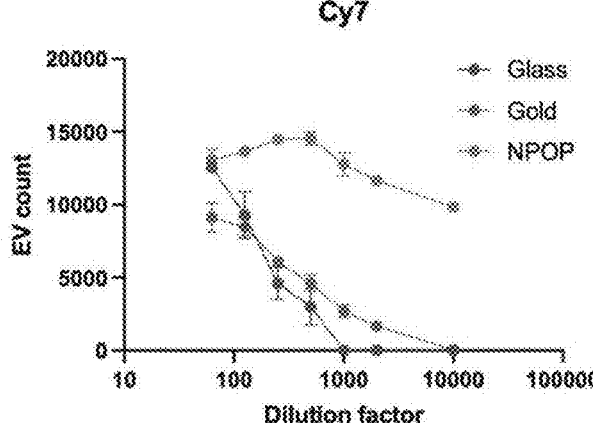
FIGS. 23A-23C are a series of graphs that show the plasmon enhancement on the NPOP substrates for Cy7 fluorophores. Imaging EVs in the Cy7 channel has been challenging due to weak fluorescence signals generated from the dye and channel. However, by using the plasmon enhancement, we could significantly amplify EV fluorescence signals when EVs are captured on the NPOP substrate compared to other plain substrates (glass or gold). This led to higher EV detection sensitivity.

FIG. 23A is a graph that shows EV count vs. dilution factor, and the EV count was clearly highest over a variety of dilution factors (top line) compared to a gold substrate and a glass substrate (dark line dropping rapidly from the left at a dilution factor of about 90 to a dilution faction of 1000, where the EV count was zero).

Figure 23B:
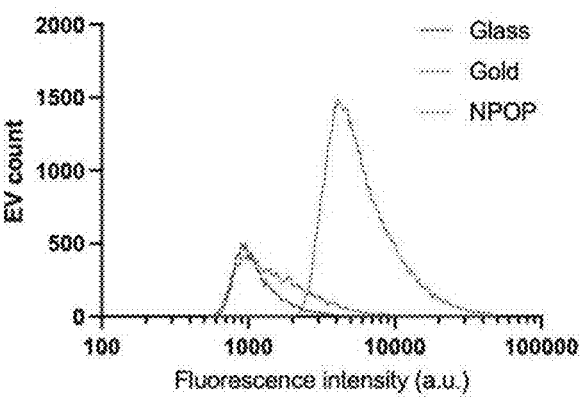

FIG. 23B is a histogram plot of the transformation of Cy7, and again, the large curve on the right, which represents the NPOP substrate showed a significantly higher EV count than glass or gold.

Figure 23C:
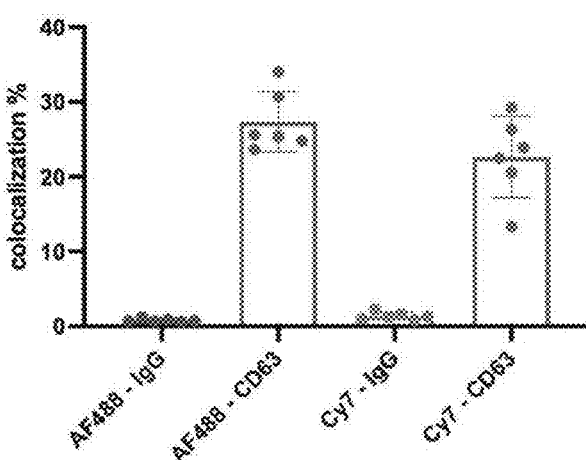

FIG. 23C is a bar graph showing that AF488-CD63 and Cy7-CD63 had the highest percentage of colonization compared to AF488-IgG or Vy7-IgG.

Example 18—CD63 Detection on EVs

In this example, EVs were labeled by TFP-AF555 dyes and captured on the NPOP substrate. Then, captured EVs were labeled by CD63 primary antibodies followed by secondary antibodies conjugated with AF647. Isotype IgG control was used as a negative control.

For EV labeling, we mixed 0.4 μg of TFP-AF555 dye, 6 μg of $2 \times 10^8$ MCF7 EVs in PBS, and 4 μg of 100 mM sodium bicarbonate and incubated for 1 hour at RT under dark conditions. We then loaded the labeled-EVs onto the Zeba™ Micro Spin Desalting Columns (ThermoFisher Scientific) to remove unbounded TFP dye, centrifuged at 1,500×g for 2 minutes and collected filtrates. We then reloaded the filtrates onto the Zeba™ Micro Spin Desalting Columns, centrifuged at 1,500×g for 2 minutes, and collected the filtrate. We then diluted the EVs with PBS in a concentration of $1 \times 10^8$, $2.5 \times 10^7$, $6.25 \times 10^6$, $1.56 \times 10^6$ EV/mL.

For NPOP preparation and EV capture we washed the substrate with water, removed the water with nitrogen gas and placed this into a humid chamber. We functionalized the NPOP substrate with 0.25 mM of SH-PEG-COOH (1.0 kDa, Nanocs) and 0.75 mM of SH-mPEG (0.35 kDa, Nanocs) in water for 4 hours at RT, and then washed with water. We treated the NPOP substrates with the mixture of 50 mM EDC (ThermoFisher Scientific) and 125 mM of sulfo-NHS (ThermoFisher Scientific) in 0.1 M MES (pH 6.0) for 7 minutes to capture the EVs by covalent bonding. We incubated the serially diluted EVs for 30 minutes at RT under dark conditions at the following concentrations ($1 \times 10^8$ EV/mL, $2.5 \times 10^7$ EV/mL, $6.25 \times 10^6$ EV/mL, and $1.56 \times 10^6$ EV/mL), and washed with PBS 3 times.

We immunostained for QUAD markers and labeled EVs as follows. We fixed and permeabilized the EVs with 4% paraformaldehyde (Electron Microscopy Sciences) and 1×Perm/Wash Buffer (BD) for 10 minutes at RT, washed with PBS 3 times, and blocked the EVs and NPOP substrates with 100% SuperBlock™ (PBS) Blocking Buffer (ThermoFisher Scientific) for 30 minutes at RT. We then added primary antibodies against mouse IgG and CD63 in 10% SuperBlock™ (PBS) Blocking Buffer in PBS and incubated for 30 minutes at RT (5 µg/mL Mouse IgG1 isotype control (Invitrogen, 14-4714-85); 10 µg/mL Mouse IgG1 CD63 (Ancell, 215-820), washed the NPOP substrate with PBST 3 times, added Goat anti-Mouse IgG (H+L) Cross-Adsorbed Secondary Antibody, Alexa Fluor™ 647 (ThermoFisher Scientific) in 10% SuperBlock™ (PBS) Blocking Buffer in PBS, and incubated for 20 minutes at RT. We then washed the NPOP substrate with PBST 3 times, and added Prolong Gold™ antifade mounting solution (ThermoFisher scientific) onto the substrate and mount the coverslip.

Figures 24A, 24B:
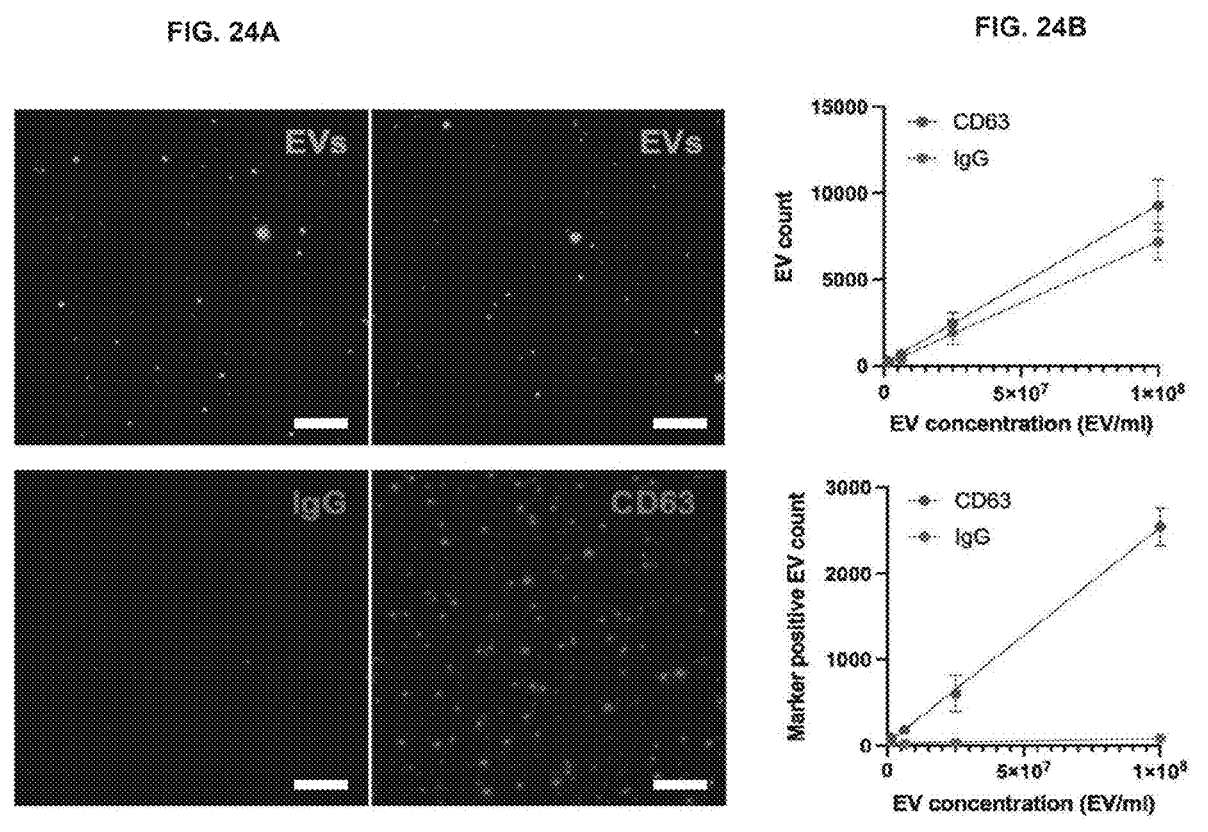

Images were taken and analyzed as follows. We obtained 4 images of EVs signals (AF555) and antibody signal (AF647) by an upright fluorescent microscopy (Zeiss) with 5 sec exposure time with 40× objective lens. We converted the raw czi files to Tiff image files, and loaded images to ImageJ™ Fiji, and subtracted the background signal. We then analyzed the number of EV and antibody signal and their co-localization using the ComDet™ Plugin with fixed parameters (approximate particle size: 4.00 pixels; intensity threshold (in SD): 3.00 around). We show the plots for EV and marker positive EV counts in serially diluted EV generated by Prism software (GraphPad) in FIGS. 24A and 24B, which show similar numbers of EVs captured on the two samples, decreasing with titrating EV concentrations. However, CD63+EV counts are significantly higher than the IgG isotype, and the CD63-positive EV counts are proportional to the EV concentrations applied on the surface.

Other Embodiments

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation and/or integration of various system modules and components in the implementations described above should not be understood as requiring such separation and/or integration in all implementations, and it should be understood that the described program components and systems can generally be integrated together in a single software product or package into multiple software products.

Accordingly, the above description of different embodiments and implementations does not define or constrain this disclosure. Other changes, substitutions, and alterations are also possible without departing from the spirit and scope of this disclosure.

What is claimed is:

1. A method of fluorescence imaging of individual target extracellular vesicles (EVs) on a substrate, the method comprising:

obtaining a nano-plasmonic array comprising,
a substrate,
a plurality of nanostructures arranged in an array on a surface of the substrate, wherein the nanostructures comprise nanorods, nanodisks, nanopillars, nanogrooves, or any combination thereof, and
one or more affinity ligands fixed on or adjacent to the nanostructures, wherein the affinity ligands specifically bind to EVs to bind the EVs to the nanostructures or to the substrate adjacent to the nanostructures;

flowing a liquid sample over the nano-plasmonic array at a flow rate that enables EVs in the liquid sample, if any, to bind to the affinity ligands thus capturing the EVs on the nano-plasmonic array;

labeling target EVs among EVs captured on the nano-plasmonic array with one or more different fluorescent reporter groups;

exposing the labeled target EVs captured on the nano-plasmonic array to a first electromagnetic radiation thereby causing the target EVs, or fluorescent reporter groups on the target EVs, or both target EVs and fluorescent reporter groups on the target EVs, to emit, scatter, or reflect one or more fluorescent signals;

receiving all or a portion of the one or more fluorescent signals, wherein the nanostructures in the nano-plasmonic array are arranged and dimensioned to amplify the fluorescent signals, thereby amplifying the fluorescent signals from individual target EVs on the substrate; and obtaining an image of one or more individual target EVs by receiving the amplified fluorescent signal.

2. The method of claim 1, (i) wherein the one or more affinity ligands bind non-specifically to at least one surface marker on the EVs, or to at least one intravesicular marker inside the EVs, or to at least one surface marker on the EVs and to at least one intravesicular marker inside the EVs; and the fluorescent reporter groups are bound to capture agents that specifically bind to at least one surface marker on the target EVs, or to at least one intravesicular marker inside the target EVs, or to at least one surface marker on the target EVs and to at least one intravesicular marker inside the target EVs, or (ii) wherein the one or more affinity ligands specifically bind to at least one surface marker on the target EVs, or to at least one intravesicular marker inside the target EVs, or to at least one surface marker on the target EVs and to at least one intravesicular marker inside the target EVs, and the fluorescent reporter groups are bound to capture agents that bind to at least one surface marker on the target EVs, or to at least one intravesicular marker inside the target EVs, or to at least one surface marker on the target EVs and to at least one intravesicular marker inside the target EVs, either specifically or non-specifically.

3. The method of claim 1, wherein the plurality of nanostructures are arranged to form a periodic array of nanostructures on the substrate, wherein the periodic array of nanostructures is arranged and dimensioned to amplify the fluorescent signals emitted, scattered, or reflected by EVs bound to the nanostructures, or EVs bound to the substrate near the nanostructures, or EVs bound to the nanostructures and EVs bound to the substrate near the nanostructures, or to amplify the fluorescent signals emitted, scattered, or reflected by the fluorescent reporter groups attached to the EVs.

4. The method of claim 1, wherein the liquid sample is from a subject, wherein the fluorescent reporter groups are bound to capture agents that specifically bind to tumor-derived target EVs, and wherein the method further comprises analyzing the obtained image to detect whether the liquid sample comprises tumor-derived target EVs, thereby detecting or monitoring cancer in the subject.

5. The method of claim 4, further comprising
identifying EVs by size and discarding any EVs or other components larger than one micron;
selecting target EVs from the identified EVs based on positivity for target EV markers to generate selected target EVs;
specifying selected target EVs as originating from specific organs or tissues by positivity for organ- or tissue-specific markers to generate specific, selected target EVs; and
analyzing individual specific, selected target EVs based on tetraspanin biomarkers on the surface of the specific target EVs, based on intravesicular biomarkers within the specific target EVs, or based on both tetraspanin and intravesicular biomarkers.

6. The method of claim 4, wherein the fluorescent reporter groups comprise a first fluorescent label.

7. The method of claim 4, wherein the reporter groups comprise antibodies that specifically bind to a biomarker on the surface of the target EVs.

8. The method of claim 7, wherein the antibodies comprise at least two different types of antibodies, wherein antibodies of a first type bind to EpCAM and antibodies of a second type bind to HER2.

9. The method of claim 7, wherein the antibodies comprise at least four different types of antibodies, wherein antibodies of a first type bind to MUC1, antibodies of a second type bind to EGFR, antibodies of a third type bind to EpCAM, and antibodies of a fourth type bind to HER2.

10. The method of claim 6, further comprising labeling target EVs that include the fluorescent reporter groups comprising the first fluorescent label with a second fluorescent label that is different from the first fluorescent label.

11. The method of claim 4, wherein the cancer is breast cancer.

12. The method of claim 1, wherein the nanostructures comprise metal nanoparticles bound to metal nanopillars.

13. The method of claim 12, wherein the metal nanoparticles comprise gold, silver, aluminum, or platinum and the metal nanopillars comprise gold, silver, aluminum, or platinum.

14. The method of claim 13, wherein the metal nanoparticles are gold and the metal nanopillars are gold.

15. The method of claim 1,
wherein the fluorescent reporter groups comprise multiple different fluorescent reporter groups; and
wherein obtaining an image of one or more individual target EV comprises conducting multichannel fluorescence imaging to form the image.

16. The method of claim 1, wherein the method enables the discrimination of individual EVs based on their cellular origins.

17. The method of claim 16, wherein the method enables the discrimination of individual target EVs originating from tumors in breast, brain, or immune system tissues.

* * * * *